United States Patent
Lassen et al.

(10) Patent No.: US 8,143,482 B2
(45) Date of Patent: Mar. 27, 2012

(54) POLYPEPTIDES HAVING ENDOGLUCANASE ACTIVITY AND POLYNUCLEOTIDES ENCODING SAME

(75) Inventors: Søren Flensted Lassen, Farum (DK); Paul Harris, Carnation, WA (US); Elena Vlasenko, Davis, CA (US); Kristian Bertel Romer Morkeberg Krogh, Bagsvaerd (DK)

(73) Assignees: Novozymes, Inc., Davis, CA (US); Novozymes Als, Bagsvaerd (DK)

( * ) Notice: Subject to any disclaimer, the term of this patent is extended or adjusted under 35 U.S.C. 154(b) by 357 days.

(21) Appl. No.: 12/293,735

(22) PCT Filed: Mar. 9, 2007

(86) PCT No.: PCT/US2007/063710
§ 371 (c)(1), (2), (4) Date: Mar. 10, 2009

(87) PCT Pub. No.: WO2007/109441
PCT Pub. Date: Sep. 27, 2007

(65) Prior Publication Data
US 2011/0047652 A1    Feb. 24, 2011

Related U.S. Application Data

(60) Provisional application No. 60/784,088, filed on Mar. 20, 2006.

(51) Int. Cl.
| | |
|---|---|
| C12N 15/31 | (2006.01) |
| C12N 15/52 | (2006.01) |
| C12N 15/10 | (2006.01) |
| C12N 15/82 | (2006.01) |
| A01H 5/00 | (2006.01) |

(52) U.S. Cl. ..... 800/288; 800/278; 800/284; 435/320.1; 435/468; 536/23.2; 536/23.7

(58) Field of Classification Search ............ None
See application file for complete search history.

(56) References Cited

U.S. PATENT DOCUMENTS
2003/0157595 A1 * 8/2003 Emalfarb et al. ........... 435/69.1
2005/0233423 A1 * 10/2005 Berka et al. ................ 435/101

FOREIGN PATENT DOCUMENTS
| | | |
|---|---|---|
| WO | WO 03/000941 | 1/2003 |
| WO | WO 03/062409 | 7/2003 |
| WO | WO 2005/059084 | 6/2005 |
| WO | 2008095033 A2 | 8/2008 |

OTHER PUBLICATIONS

Dalbøge et al., A novel method for efficient expression cloning of fungal enzyme genes, Mol. Gen. Genet., vol. 243, 1994, pp. 253-260.
Henriksson et al., A critical review of cellobiose dehydrogenases, Journal of Biotechnology, vol. 78, 2000, pp. 93-113.
Maheshwari et al., Thermophilic Fungi: Their Physiology and Enzymes, Microbiology and Molecular Biology Reviews, Sep. 2000, pp. 461-488.
Rosgaard et al., Efficiency of New Fungal Cellulase Systems in Boosting Enzymatic Degradation of Barley Straw Lignocellulose, Biotechnology Prog, vol 22, 2005, pp. 493-498.
Sen et al., Characteristics of the cellulase produced by *Myceliophthora thermophila* D-14, Can. J. Microbial. 1982, vol. 28, pp. 271-277.
Bhat et al., *Sporotrichum thermophila* Growth, Cellulose Degradation, and Cellulase Activity, Applied and Environmental Microbiology, 1987, pp. 2175-2182.
Jørgensen et al., Purification and characterization of five cellulases and one xylanase from *Penicillium brasilianum* IBT 20888, Enzyme and Microbial Technology, vol. 32, 2003, pp. 851-861.
Klyosov et al., A Thermostavle Endo-1, 4-Beta-Glucanase from *Myceliophthora Thermophila*, Biotechnology Letters, vol. 10, 1988, pp. 351-354.
Thygesen et al., Production of cellulose and hemicellulose-degrading enzymes by filamentous fungi cultivated on wet-oxidised wheat straw, Enzyme and Microbial Technology, vol. 32, 2003, pp. 606-615.
Breuil et al.,1986, Biotechnol Letters 8, 673-676.
Kvesitadze et al., 1995, Appl Biochem Biotechnol 50, 137-143.
Uniprot, Accession No. Q2HF16, 2006.
Uniprot, Accession No. Q7SDR1, 2003.
Database Acces No. ASR9421.
Jorgensen et al, 2006, Enzy Microbiol Technol 38 (3-4), 381-390.
Krough et al, 2009, Enzy Microbiol Technol 44 (6-7), 359-367.
Neirman et al, 2005, Uniprot Access No. Q4WM09.
Neirman et al, 2005, Nature 438 (7071), 1151-115.
Takada et al, 2002, J Biosci Bioengg 94 (5), 482-485.

* cited by examiner

*Primary Examiner* — Brent T Page
(74) *Attorney, Agent, or Firm* — Robert L. Starnes; Eric J. Fechter

(57) ABSTRACT

The present invention relates to isolated polypeptides having endoglucanase activity and isolated polynucleotides encoding the polypeptides. The invention also relates to nucleic acid constructs, vectors, and host cells comprising the polynucleotides as well as methods for producing and using the polypeptides.

26 Claims, 20 Drawing Sheets

```
CGACTTGAAACGCCCCAAAATGAAGTCCTCCATCCTCGCCAGCGTCTTCGCCACGGGCGCCGTGGCTGGCGCCGTGGCCGTCAAAGTGGTCCGTGGCTCAAAGTGGTCCGTGGC
              M  K  S  S  I  L  A  S  V  F  A  T  G  A  V  A  Q  S  G  P  W  Q  Q  C  G  G
ATCGGATGGCAAGGATCGACCGACTGTGTCTCGGGCTACCACTGCGTCTACCAGAACGATTGGTACAGCCAGTGCCTGGCCGCGGCGTCGACA
 I  G  W  Q  G  S  T  D  C  V  S  G  Y  H  C  V  Y  Q  N  D  W  Y  S  Q  C  V  P  G  A  A  S  T
ACGCTGCAGACAATCGACAACCAGTCGGGCGCCCCGGTCCACCAGCACCGCCAGCACTTCATCTTCCCGTCAGCACTTCATCTTCCCGTCAGCACTTCATCTTCCCGTCAGC
 T  L  Q  T  S  R  P  T  A  T  S  R  P  T  A  P  P  S  T  T  S  P  S  K  G  K  L  K  W  L
GGCAGCAACGAGTCGGGCGCGGAGTTCGGAGGCGAAGGCAATTACCCCGGCCTCTGGGGCAAGCACTTCATCTTCCCGTCGACTTCGGCGATTCAGACG
 G  S  N  E  S  G  A  E  F  G  E  G  N  Y  P  G  L  W  G  K  H  F  I  F  P  S  A  I  Q  T
CTCATCAATGATGGATACAACATCTTCCGGATGACTTCTGAACGCGTCTGTGCCCAACCAGTTGACGTGTCCTTCGACCAGGGTTACCTC
 L  I  N  D  G  Y  N  I  F  R  I  D  F  S  M  E  R  L  V  P  N  Q  L  T  S  S  F  D  Q  G  Y  L
CGCAACCTGACCGAGGTGGTCAACTTCGTCAACGGCGCAAGTTCCGGACCGTTCCGACACTCGTCATCTTCGACACCAACGAGTACAACATC
 R  N  L  T  E  V  V  N  F  V  T  N  A  G  K  Y  A  V  L  D  P  H  N  Y  G  R  Y  G  N  I  I
ACGGACACGAACGCGTTCCGGACCTTCTGGACCAACCTGGCCAAGCAGTTCGCTCAACTCGTCATCTTCGACACCAACGAGTACAACATC
 T  D  T  N  A  F  R  T  F  W  T  N  L  A  K  Q  F  A  S  N  S  L  V  I  F  D  T  N  E  Y  N
ACGATGGACCAGACCCTGGTCCTCAACCTCAACGGGGCCATCGACGGCATCCGCGCGGCAGGCACCGCGCAGTACATCTTCGTGGAGGGC
 T  M  D  Q  T  L  V  L  N  L  N  Q  A  A  I  D  G  I  R  A  A  G  A  T  S  Q  Y  I  F  V  E  G
AACGCGTGGAGCGGGGCCTGGAGCTGGAACACCCACGCCAGCAGCGCGTCAGCGCCATCGGGAGCGCGTCGTCGGAGCCACCCAGTGGCTCCGCGCC
 N  A  W  S  G  A  W  S  W  N  T  T  N  T  N  M  A  A  L  T  D  P  Q  N  K  I  V  Y  E  M  H  Q
TACCTCGACTCGAGCGGCACAGCGAGTGCGTCGAGTACCATCGGAGCGCAGCGGGTCGTCGGCGCCACGCAGTGGCTCCGCGCC
 Y  L  D  S  S  G  T  H  A  E  C  V  S  S  T  I  G  A  Q  R  V  V  G  A  T  Q  W  L  R  A
AACGGCAAGCTCGGGGTCCTCGGCGTCCTGGGCGTCCTCGGCGCCGCCAACGCCGTGTGCCAGCAGGCCGTGACTGGCCTCCTCGACCACCTCCAGGACAAC
 N  G  K  L  G  V  L  G  E  F  A  G  G  A  N  A  V  C  Q  Q  A  V  T  G  L  L  D  H  L  Q  D  N
AGCGACGTCGTGGGGGGGCGCGCCTGGGGCGACTACATGTACTCGTTCGAGCCTCCTCGGGCACCGGCTATGTC
 S  D  V  W  L  G  A  L  W  A  A  G  P  W  N  G  D  Y  M  Y  S  F  E  P  P  S  G  T  G  Y  V
AACTACAACTCGATCTTGAAGAAGTACTTGCCGTAA
 N  Y  N  S  I  L  K  K  Y  L  P
```

Fig. 2

```
GGATCCACTTAGTAACGGGCCGCCACTGTGCTGTGGAAAGCATGAAGTCTCTTCTTCCTGTCACTTGTAGCACCGTCGCGCTCAGCTCGC
                                    M  K  S  L  F  L  S  L  V  A  T  V  A  L  S  S
CAGTATTCTCTGTCGCAGTCTGGGGCAATGCCCGGCATTGGCTTCAGCGAAGCACCGTCTGTGATGCAGGCGCCGGCTGTGTGA
 P  V  F  S  V  A  V  W  G  Q  C  G  G  I  G  F  S  G  S  T  V  C  D  A  G  C  V
AGCTCAACGACTATTACTCTCAATGCCAACCGGCTCCCACTGCTACATCGGCGGCCCAAGTAGCAACGCCACCGTCCGGCACTT
 K  L  N  D  Y  Y  S  Q  C  Q  P  G  A  P  T  A  T  S  A  A  P  S  S  N  A  P  S  T
CGACGGGCCTCGGCCCCCCCCCTTGCTCTGCAGCCGCACGCCGTTCCAGTTCTTCGGTGTCAACGAATCCGGCGCGGAGT
 S  T  A  S  A  P  S  S  L  C  S  G  S  R  T  P  F  Q  F  F  G  V  N  E  S  G  A  E
TCGGCAACCTGAACATCCCGGTGTTCTGGGACGTCGGACACCTGGCCGTCGCCATCCAGCATTGACTTCTTCATGGGCAAGGGAA
 F  G  N  L  N  I  P  G  V  L  G  T  D  Y  T  W  P  S  S  I  D  F  F  M  G  K  G
TGAATACCTTCCGTATTCCGTTCCTCATGGAGCGTCTTGTCCCCCCTGCATCAGGACCTCTGACCAGACGTACTTGG
 M  N  T  F  R  I  P  F  L  M  E  R  L  V  P  P  A  T  G  I  T  G  P  L  D  Q  T  Y  L
GCGGCCTGCAGACGATTGTCAACTACATCACCGGCAAAGGCGCTTTGCTCTCATTGACCGCACAACTTTATGATCTACAATGGCC
 G  G  L  Q  T  I  V  N  Y  I  T  G  K  G  G  F  A  L  I  D  P  H  N  F  M  I  Y  N  G
AGAGCGATCTCCAGTACCAGACTTCCAGAAGTTCTGGCAGGAGTGTTTAAATCGAACAGTCACGTCATCTTCGATG
 Q  T  I  S  S  T  S  D  P  Q  K  F  W  Q  N  L  A  G  V  F  K  S  N  H  V  I  F  D
TTATGAACGAGCCTCACGATATTCCCGCCCAGACCGTTCTCAATGAAGCCAAGCGCTGTGTCGAGAGCGGTGCGA
 V  M  N  E  P  H  D  I  P  A  Q  T  V  F  Q  L  N  Q  A  A  V  N  G  I  R  A  S  G  A
CGTCGCAGCTCATTCTGGTCGAGGGCACAAGCTGGACTGGAGCCTGGATAGCTTGGCACTTCGCAGACCTGCCTGTCTC
 T  S  Q  L  I  L  V  E  G  T  S  W  T  G  A  W  T  W  T  S  G  N  S  D  A  F  G  A
TTAAGGATCCCAACAACAACGTCGCGATCCAGATGCACTACCTGGATAGTGATGGCTCGACAAGTCAAGCAGAACAACTCAAGGGCCTTCCTGGGCGAGATCGGCGCCG
 I  K  D  P  N  N  V  A  I  Q  M  H  Y  L  D  S  D  G  S  T  S  Q  T  C  V  S
CCACCATCGGTGCCGAGCGGTTGCAGGCCGACTCAATGGTTGAAGCAGAACAACTCAAGCAGAATCTGAAGGGCCTTCCTGGGCGAGATCGGCGCCG
 P  T  I  G  A  E  R  L  Q  A  A  T  Q  W  L  K  Q  N  N  L  K  G  F  L  G  E  I  G  A
GCTCTAACTCCGCTTGCATCAGCGCTGTGTGCAGGGTGCCGTTGTGTTGCATGCAGCAATCTGGTGTCCCCGGCAATCTCCGCTCTGGGG
 G  S  N  S  A  C  I  S  A  V  Q  G  A  L  C  S  M  Q  Q  S  G  V  W  L  G  A  L  W  W
CTGCGGGCCGGTGTGGGCGACTACTACCAGTCCATCGAGCCGCCCTCTGGCCCGGCCGTCTCCGCCATCCTCCCGCAGGCCCTGCCG
 A  A  G  P  W  G  D  Y  Y  Q  S  I  E  P  P  S  G  P  A  V  S  A  I  L  P  Q  A  L
TGCCGTTCGCGTAA
 L  P  F  A
```

Fig. 6

```
GGAAAGCCGTCAGTATGGTGAAATTTGCGCTTGTGGCAACTGTCGGCGCAATCTTGAGCGCTTCTGCGGCCAATGCGGCTTCTATCTA
           M  V  K  F  A  L  V  A  T  V  G  A  I  L  S  A  S  A  A  N  A  A  S  I  Y
CCAGCAATGTGGAGGCATTGGAGTGTTCGGTCCACTGTTTGCCGACGCCGGTCTTGCCGTTATCCTCAATGCTACTACTTTCA
 Q  Q  C  G  G  I  G  W  S  G  S  T  V  C  D  A  G  L  A  C  V  I  L  N  A  Y  Y  F  Q
GTGCTTGAGCACACTGCCGCGGGCCAGACAACGGACCGGCTCGGGCGACGAAACAACTACCACTCCGTCAACATCAACCTCTCACTACGGG
 C  L  T  P  A  A  G  Q  T  T  G  S  G  A  P  A  S  T  S  H  S  T  V  T  T  G
GAGCTCACACTGCTCTGGCCTCCAGGACGAAGTTCAAGTTCTTCCGGTGTGAATGAAAGCGGCGCCGAATTCGGGAACACTGCTTGCC
 S  S  H  S  T  T  G  T  T  A  T  K  T  T  T  P  S  T  T  T  L  P  A  I  S  V  S
TGGTCGCGTCTGCTCTGGCCTCCAGGACGAAGTTCAAGTTCTTCCGGTGTGAATGAAAGCGGCGCCGAATTCGGGAACACTGCTTGCC
 G  R  V  C  S  G  S  R  T  K  F  F  G  V  N  E  S  G  A  E  F  G  N  T  A  W  P
AGGGCAGCTCGGAAAGACTATACATGAGCCCTCCGGCTACCGGACTCACTGGCCCGTTTAATCAACTTCATGGGGCTGGATTCAATACATTCCGTATCAC
 G  Q  L  G  K  D  Y  T  W  P  S  P  S  S  V  D  Y  F  M  G  A  G  F  N  T  F  R  I  T
CTTCTTGATGGAGAGCTATGAGCCCTCCGGCTACCGGACTCACTGGCCCCGTTTAATCAACTTCATGCGCTACTACAACGGCATAATCAGCAGCACATGT
 F  L  M  E  R  M  S  P  P  A  T  G  L  T  G  P  F  N  Q  T  Y  L  S  G  L  T  T  I  V
CGACTACATCGACAAGAAATCCACGAAGAACGCCATCTTCGACATCCAGAACGAGCCGTACGG
 D  Y  I  T  N  K  G  Y  A  L  I  D  P  H  N  F  M  R  Y  N  N  G  I  I  S  S  T  S
TGACTTCGCAGCTTGGTGGAGCAATTGGACCGTATACGAAGTTGGCCATCAATTCGAATTCAAGTCGCCGTCACGTTGATTCTGGT
 D  F  A  T  W  W  S  N  L  A  T  V  F  K  S  T  K  N  A  I  F  D  I  Q  N  E  P  Y  G
AATCGATGCGCAGACGGTCATACACTGGAGCTTGGACGTTGGGCGCTTCGGCGGAAACGAGCTGCTTCGCGGCCGTTACGGATCCTTACAACAA
 I  D  A  Q  T  V  Y  E  L  N  Q  A  A  I  N  S  I  R  A  A  G  A  T  S  Q  L  I  L  V
TGAAGGAACGTCATACACTGGAGCTTGGACCGTATACGAAGTTGGAGCAGCTTCGCGGCGCCGTTACGGATCCTTACAACAA
 E  G  T  S  Y  T  G  A  W  T  M  V  S  S  G  N  G  A  A  F  A  A  V  T  D  P  Y  N
CACGGCAATTGAAATGCACCAATACCTGCTGCACAAACAGGACTCAAGGATTCCTGGAGTGTGTCTCCACCATTGGGTCGCAACG
 T  A  I  E  M  H  Q  Y  L  D  S  D  G  S  G  T  N  E  D  C  V  S  S  T  I  G  S  R
TCTCCAAGCTGCTGTTCGATGAACTTTGCTATATGCAACAAGCAAGGCGGCTCCTGGATCGGCGCTCTGTGGGCTGCCCTGTGGGTCTCCCTGGTG
 L  Q  A  A  T  A  W  L  Q  Q  T  G  L  K  G  F  L  G  E  T  G  A  G  S  N  S  Q  C  I
CGACGCCGTGTTCGATGAACTTACTCGATTGAACCTCGAGTTGCCGCTATCCCAGAAGTCCTTCCTCAGGGTCCTGCTCAATTCCTAG
 D  A  V  F  D  E  L  C  Y  M  Q  Q  Q  G  G  S  W  I  G  A  L  W  A  A  G  P  W
GGGCACGTACATTTACTCGATTGAACCTCGAGTTGCCGCTATCCCAGAAGTCCTTCCTCAGGGTCCTGCTCAATTCCTAG
 G  T  Y  I  Y  S  I  E  P  P  S  G  A  A  I  P  E  V  L  P  Q  G  L  A  P  F  L
```

Fig. 9

```
ATGAAATACCCTCTACTCCTTGCAACCAGCGCTGCCCTGGCTCTTGCTGGGCCTTCTCTCTTTTGTTTGTATG
 M  K  Y  P  L  L  A  T  S  A  A  L  A  L  A  G  P  Q  G  F  S  K  R  A  S  S  F  V
TGTAGAGCCCATAAGAATAAGAGACTGAACTGACCTGAATTTTGAGGGTTGTGTACCAGCGAGTTTGGCAATCAGAACATT
                                         W  F  G  T  S  E  S  G  A  E  F  G  N  Q  N  I
CCGGGTGTTTTGGGGACGGACTACATTTGGCCCGACACTTCAGCACTTCAAACGGGTATGAACATCTTTCGGGTGGCATTT
 P  G  V  L  G  T  D  Y  I  W  P  D  T  S  A  I  Q  T  L  R  N  A  G  M  N  I  F  R  V  A  F
TGATGGAGCGATTGGTTCCCACCACATTGACTTCAACTCCGGATTCGCAAGAACGTACGTTATCCTCGTCAACAA
 L  M  E  R  L  V  P  T  T  L  T  S  T  P  D  S  T  Y  L  Q  D  L  K  S  V
TGCAACCCCGTGCTAAACGATTCTCCAGACAGTTGACTACATCACGTCGACCCCCATAACTTCCACAAGTGACTTTGCTGCA
                                     L  D  Y  I  T  G  A  Y  A  I  V  D  P  H  N  F  G  R  Y
AAGTTGAACCTTTCATCTAACCAATCTGAAAAATCCCTCGACGGGTGTATTAGCTATGGCAATATAATCAACTACTTACTTCACTACTTTGTTCCCCA
                                     Y  G  N  I  I  N  S  T  S  D  F  A  A
TTTTGGACCACCGTCGCAAAGCAGTTTGCATCGAATGACAAGACCTGCTGTACTGAACCTCAATCAAGCGGCCATTAATGCCATCGAGCTGC
 F  W  T  T  V  A  K  Q  F  A  S  N  D  K  V  I  F  D  T
CTAACTGACATCTGCAGACAGCAACGAATTCAACACGAGGACCAAACGCTTGTACTGGTGCTGGACGTGGTGCCTGGACGTCAGTCTTGAC
              N  N  E  F  N  T  E  D  Q  T  L  V  L  N  L  N  Q  A  A  I  N  A  I  R  A  A
CGGAGCCCACCTCTCAGTATATCTTTGTGGAAGGGAATTCTTGGAGTGGCGCAAATGGACGTCGGTCAGTCTCAGCTCGACCATCGG
 G  A  T  S  Q  Y  I  F  V  E  G  N  S  W  S  G  A  W  T  W  T  S  V  N  T  N  L  V  S  L  T
GGACCCCAACAACAAGATAGTCTACGAGATGCACCAGTACTTGACTTGGTGATGGCAAATTGGGGCGAATTCTTGGGGCGTGCTAACTCGGTCTG
 D  P  N  N  K  I  V  Y  E  M  H  Q  Y  L  D  S  D  G  S  G  T  S  D  T  C  V  S  S  T  I  G
CCAAGGAGCGTGTACAATCGGCACCGAGTGGCTGAAAAGCAATGGGGAAATTCTTGGAGTTGCGGAATTGCGGTGCTAACTGGTCTG
 Q  E  R  V  Q  S  A  T  E  W  L  K  S  N  G  K  L  G  F  L  G  E  F  A  G  G  A  N  S  V  C
TCAGAGCGCCGTGACTGGAATGCTGGACTATATGCAAGCGAATAGTGACGTTCTGGCTCGGCGCCATCTCTGTCTGCTGCCAGTGGTGGG
 Q  S  A  V  T  G  M  L  D  Y  M  Q  A  N  S  D  V  W  L  G  A  S  W  A  A  G  P  W  W  G
AACCTATATATATCGATTGAGCCGCCATCTCCCCTCTTCCCCAGCTCCGGAAG
 T  Y  I  Y  S  I  E  P  P  S  G  T  A  Y  S  Y  Y  L  N  I  L  S  A  Y  F  P  S  S  G  S
```

Fig. 10A

```
TTCCACAACCACAACTACCTCCACTACCACCCGCTCTACATTGACAAGCACTACAGTATCCACCAAATCAACAAGCACCACTACAAGCGC
 S  F  T  T  T  S  T  T  R  S  T  T  S  I  H  Q  T  R  T  T  V  S  T  T  K  S  T  T  T  S  A
CACGAAATCGACAAGCACCACGACACCAAGCACCAGCAGTCTACTGTCAACAGCATTCACTGGGCACAGTGTGGCGGCATTGG
 T  E  I  D  K  H  H  D  T  K  H  Q  Q  S  T  V  L  L  Q  Q  H  S  L  G  T  V  W  R  H  W
CTGGACGGGGGCGACGAGTGTGCCAGCCCGTATACCTGCCAGGTCCAGTTGTAATGCGTATTATTCGCAGTGTCTGTAATGCAGAAGTATCAGAAA
 L  D  G  G  D  E  C  A  S  P  Y  T  C  Q  V  Q  L  *  C  V  L  *  C  R  S  I  R  K
```

POLYPEPTIDES HAVING ENDOGLUCANASE ACTIVITY AND POLYNUCLEOTIDES ENCODING SAME

CROSS-REFERENCE TO RELATED APPLICATIONS

This application is a 35 U.S.C. 371 national application of PCT/US07/63710 filed on Mar. 9, 2007 and claims priority from U.S. provisional application Ser. No. 60/784,088 filed on Mar. 20, 2006, which applications are fully incorporated herein by reference.

REFERENCE TO A SEQUENCE LISTING

This application contains a Sequence Listing in computer readable form. The computer readable form is incorporated herein by reference.

REFERENCE TO A DEPOSIT OF BIOLOGICAL MATERIAL

This application contains a reference to deposits of biological material which have been made at the Northern Regional Research Center (NRRL) under the Budapest Treaty and assigned accession numbers NRRL B-30900N, NRRL B-30902, NRRL B-30903, and NRRL B-30904, which microbial deposits are incorporated herein by reference.

BACKGROUND OF THE INVENTION

1. Field of the Invention

The present invention relates to isolated polypeptides having endoglucanase activity and isolated polynucleotides encoding the polypeptides. The invention also relates to nucleic acid constructs, vectors, and host cells comprising the polynucleotides as well as methods for producing and using the polypeptides.

2. Description of the Related Art

Cellulose is a polymer of the simple sugar glucose covalently bonded by beta-1,4-linkages. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiohydrolase I is a 1,4-beta-D-glucan cellobiohydrolase (E.C. 3.2.1.91) activity which catalyzes the hydrolysis of 1,4-beta-D-glucosidic linkages in cellulose, cellotetriose, or any beta-1,4-linked glucose containing polymer, releasing cellobiose from the reducing ends of the chain. Cellobiohydrolase II is a 1,4-D-glucan cellobiohydrolase (E.C. 3.2.1.91) activity which catalyzes the hydrolysis of 1,4-beta-D-glucosidic linkages in cellulose, cellotetriose, or any beta-1,4-linked glucose containing polymer, releasing cellobiose from the non-reducing ends of the chain. Cellobiose is a water-soluble beta-1,4-linked dimer of glucose. Beta-glucosidases hydrolyze cellobiose to glucose.

The conversion of cellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol.

Roy et al, 1990, *Journal of General Microbiology* 136: 1967-1972, disclose the purification and properties of an extracellular endoglucanase from *Myceliophthora thermophila* ATCC 48104 Chernoglazov et al., 1988, *Biokhimiya* 53: 475-482, disclose the isolation, purification, and substrate specificity of an endoglucanase from *Myceliophthora thermophila*. Klyosov et al., 1988, *Biotechnology Letters* 10: 351-354, disclose a thermostable endoglucanase from *Myceliophthora thermophila*, Guzhova and Loginova, 1987, *Prikladnaya Biokhimiya I Mikrabiologiya* 23: 820-825, disclose cellulolytic enzymes from *Myceliophthora thermophila*. Rabinovich et al., 1986, *Bioorganicheskaya Khimiya* 12: 1549-1560, disclose the purification and characterization of an endoglucanase from *Myceliophthora thermophila*, Svistova et al., 1986, *Mikrobiologiya* 55: 49-54, disclose the regulation of cellulose biosynthesis in *Myceliophthora thermophila*. Bhat and Maheshwari, 1987, *Applied and Environmental Microbiology* 53: 2175-2182, disclose the activity of components of the extracellular cellulose system of *Myceliophthora thermophila*. Klyosov et al., 1987, *Prikladnaya Biokhimiya I Mikrobiologiya* 23: 44-50, disclose a thermostable endoglucanase from *Myceliophthora thermophila*. Jorgensen et al., 2003, *Enzyme and Microbial Technology* 32: 851-861, and Thygesen et al., 2003, *Enzyme and Microbial Technology* 32: 606-615, disclose cellulose-degrading enzymes from *Penicillium brasilianum* IBT 20888.

It would be an advantage in the art to identify new endoglucanases having improved properties, such as improved hydrolysis rate, better thermal stability, reduced adsorption to lignin, and ability to hydrolyze non-cellulosic components of biomass, such as hemicellulose, in addition to hydrolyzing cellulose. Endoglucanases with a broad range of side activities on hemicellulose can be especially beneficial for improving the overall hydrolysis yield of complex, hemicellulose-rich biomass substrates.

It is an object of the present invention to provide improved polypeptides having endoglucanase activity and polynucleotides encoding the polypeptides.

SUMMARY OF THE INVENTION

The present invention relates to isolated polypeptides having endoglucanase activity selected from the group consisting of:

(a) a polypeptide comprising an amino acid sequence which has at least 80% identity with the mature polypeptide of SEQ ID NO: 4 or SEQ ID NO: 10, at least 85% identity with the mature polypeptide of SEQ ID NO: 6, or at least 75% identity with the mature polypeptide of SEQ ID NO: 8;

(b) a polypeptide which is encoded by a polynucleotide which hybridizes under at least high stringency conditions with (i) the mature polypeptide coding sequence of SEQ ID NO: 3, SEQ ID NO: 5, SEQ ID NO: 7, or SEQ ID NO: 9, (ii) the cDNA sequence contained in the mature polypeptide coding sequence of SEQ ID NO: 3 or SEQ ID NO: 9 or the genomic DNA sequence comprising the mature polypeptide coding sequence of SEQ ID NO: 5 or SEQ ID NO: 7 or (iii) a full-length complementary strand of (i) or (ii);

(c) a polypeptide which is encoded by a polynucleotide having at least 80% identity with the mature polypeptide coding sequence of SEQ ID NO: 3 or SEQ ID NO: 9, at least 85% identity with the mature polypeptide coding sequence of SEQ ID NO: 5, or at least 75% identity with the mature polypeptide coding sequence of SEQ ID NO: 7; and (d) a variant comprising a substitution, deletion, and/or insertion of one or more amino acids of the mature polypeptide of SEQ ID NO: 4, SEQ ID NO: 6, SEQ ID NO: 8, or SEQ ID NO: 10.

The present invention also relates to isolated polynucleotides encoding polypeptides having endoglucanase activity, selected from the group consisting of:

(a) a polynucleotide encoding a polypeptide comprising an amino acid sequence which has at least 80% identity with the mature polypeptide of SEQ ID NO: 4 or SEQ ID NO: 10, at least 85% identity with the mature polypeptide of SEQ ID NO: 6, or at least 75% identity with the mature polypeptide of SEQ ID NO 8;

(b) a polynucleotide which hybridizes under at least high stringency conditions with (i) the mature polypeptide coding sequence of SEQ ID NO: 3, SEQ ID NO: 5, SEQ ID NO: 7, or SEQ ID NO: 9, (ii) the cDNA sequence contained in the mature polypeptide coding sequence of SEQ ID NO: 3 or SEQ ID NO: 9 or the genomic DNA sequence comprising the mature polypeptide coding sequence of SEQ ID NO: 5 or SEQ ID NO: 7, or (iii) a complementary strand of (i) or (ii);

(c) a polynucleotide having at least 80% identity with the mature polypeptide coding sequence of SEQ ID NO: 3 or SEQ ID NO: 9, at least 85% identity with the mature polypeptide coding sequence of SEQ ID NO: 5, or at least 75% identity with the mature polypeptide coding sequence of SEQ ID NO: 7; and (d) a polynucleotide encoding a variant comprising a substitution, deletion, and/or insertion of one or more amino acids of the mature polypeptide of SEQ ID NO: 4, SEQ ID NO: 6, SEQ ID NO: 8, or SEQ ID NO: 10.

In a preferred aspect, the mature polypeptide is amino acids 17 to 389 of SEQ ID NO: 4. In another preferred aspect, the mature polypeptide is amino acids 16 to 397 of SEQ ID NO: 6. In another preferred aspect, the mature polypeptide is amino acids 22 to 429 of SEQ ID NO: 8. In another preferred aspect, the mature polypeptide is amino acids 25 to 421 of SEQ ID NO: 10. In another preferred aspect, the mature polypeptide coding sequence is nucleotides 67 to 1185 of SEQ ID NO: 3. In another preferred aspect, the mature polypeptide coding sequence is nucleotides 84 to 1229 of SEQ ID NO: 5 In another preferred aspect, the mature polypeptide coding sequence is nucleotides 77 to 1300 of SEQ ID NO: 7. In another preferred aspect, the mature polypeptide coding sequence is nucleotides 73 to 1468 of SEQ ID NO: 9.

The present invention also relates to nucleic acid constructs, recombinant expression vectors, recombinant host cells comprising the polynucleotides, and methods of producing a polypeptide having endoglucanase activity.

The present invention also relates to methods of inhibiting the expression of a polypeptide in a cell, comprising administering to the cell or expressing in the cell a double-stranded RNA (dsRNA) molecule, wherein the dsRNA comprises a subsequence of a polynucleotide of the present invention. The present also relates to such a double-stranded inhibitory RNA (dsRNA) molecule, wherein optionally the dsRNA is an siRNA or an miRNA molecule.

The present invention also relates to methods of using the polypeptides having endoglucanase activity in the conversion of cellulose to glucose and various substances.

The present invention also relates to plants comprising an isolated polynucleotide encoding such a polypeptide having endoglucanase activity.

The present invention also relates to methods for producing such a polypeptide having endoglucanase activity, comprising: (a) cultivating a transgenic plant or a plant cell comprising a polynucleotide encoding such a polypeptide having endoglucanase activity under conditions conducive for production of the polypeptide; and (b) recovering the polypeptide.

The present invention further relates to nucleic acid constructs comprising a gene encoding a protein, wherein the gene is operably linked to a nucleotide sequence encoding a signal peptide comprising or consisting of amino acids 1 to 16 of SEQ ID NO: 4, amino acids 1 to 15 of SEQ ID NO: 6, amino acids 1 to 21 of SEQ ID NO: 8, or amino acids 1 to 16 of SEQ ID NO: 10 and a second nucleotide sequence encoding a propeptide comprising or consisting of amino acids 17 to 24 of SEQ ID NO: 10, wherein the gene is foreign to the first and second nucleotide sequences

BRIEF DESCRIPTION OF THE FIGURES

FIG. 2 shows the genomic DNA sequence and the deduced amino acid sequence of a *Myceliophthora thermophila* CBS 117.65 endoglucanase (SEQ ID NOs: 3 and 4, respectively).
FIG. 6 shows the cDNA sequence and the deduced amino acid sequence of a basidiomycete CBS 495.95 endoglucanase (SEQ ID NOs: 5 and 6, respectively).
FIG. 9 shows the cDNA sequence and the deduced amino acid sequence of a basidiomycete CBS 494.95 endoglucanase (SEQ ID NOs: 7 and 8, respectively).
FIGS. 10A and 10B show the genomic DNA sequence and the deduced amino acid sequence of a *Penicillium brasilianum* strain IBT 20888 endoglucanase (SEQ ID NOs: 9 and 10, respectively)

DEFINITIONS

Figure 1:
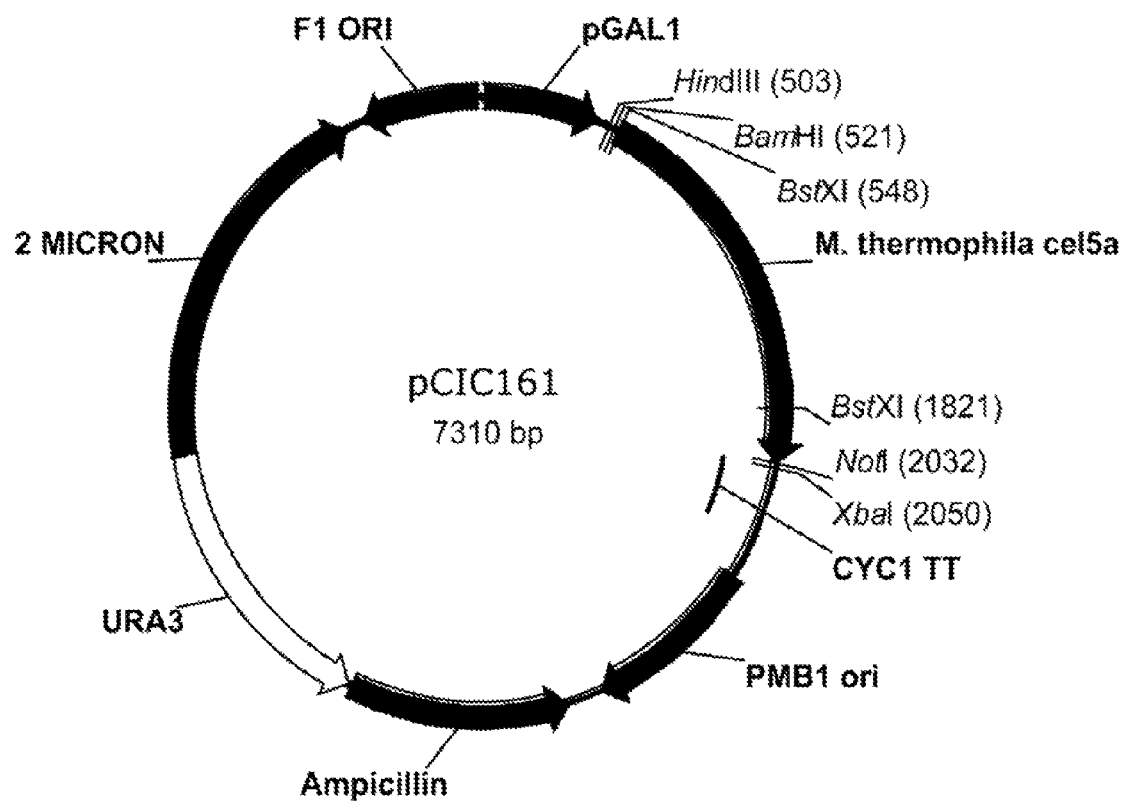
FIG. 1 shows a restriction map of pCIC161.

Endoglucanase activity: The term "endoglucanase activity" is defined herein as an endo-1,4-beta-D-glucan 4-glucanohydrolase (E.C. No. 3.2.1.4) which catalyses the endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. For purposes of the present invention, endoglucanase activity is determined using carboxymethyl cellulose (CMC) hydrolysis according to the procedure of Ghose, 1987, *Pure and Appl. Chem.* 59: 257-268. One unit of endoglucanase activity is defined as 1.0 μmole of reducing sugars produced per minute at 50° C., pH 4.8.

In a preferred aspect, the polypeptides of the present invention having endoglucanase activity further have enzyme activity toward one or more substrates selected from the group consisting of xylan, xyloglucan, arabinoxylan, 1,4-beta-D-mannan, and galactomannan. The activity of the polypeptides having endoglucanase activity on these polysaccharide substrates is determined as percent of the substrate hydrolyzed to reducing sugars after incubating the substrate (5 mg per ml) with a polypeptide having endoglucanase activity of the present invention (5 mg protein per g of substrate) for 24 hours with intermittent stirring at pH 5.0 (50 mM sodium acetate) and 50° C. Reducing sugars in hydrolysis mixtures are deter wined by the p-hydroxybenzoic acid hydrazide (PHBAH) assay.

In a more preferred aspect, the polypeptides of the present invention having endoglucanase activity further have enzyme activity toward xylan. In another more preferred aspect, the polypeptides of the present invention having endoglucanase activity further have enzyme activity toward xyloglucan. In another more preferred aspect, the polypeptides of the present invention having endoglucanase activity further have enzyme activity toward arabinoxylan. In another more preferred aspect, the polypeptides of the present invention having endoglucanase activity further have enzyme activity toward 1,4-beta-D-mannan. In another more preferred aspect, the polypeptides of the present invention having endoglucanase activity further have enzyme activity toward galactomannan. In another more preferred aspect, the polypeptides of the present invention having endoglucanase activity further have enzyme activity toward xylan, xyloglucan, arabinoxylan, 1,4-beta-D-mannan, and/or galactomannan.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the endoglucanase activity of mature polypeptide of SEQ ID NO: 4, SEQ ID NO: 6, SEQ ID NO: 8, or SEQ ID NO: 10.

Family 5 glycoside hydrolase or Family GH5: The term "Family 5 glycoside hydrolase" or "Family GH5" is defined herein as a polypeptide falling into the glycoside hydrolase Family 5 according to Henrissat B., 1991. A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively or recombinantly associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Mature polypeptide: The term "mature polypeptide" is defined herein as a polypeptide having endoglucanase activity that is in its final form following translation and any post-translational modifications, such as N-terminal processing, C-terminal truncation, glycosylation, etc.

Mature polypeptide coding sequence: The term "mature polypeptide coding sequence" is defined herein as a nucleotide sequence that encodes a mature polypeptide having endoglucanase activity.

Identity: The relatedness between two amino acid sequences or between nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The output of Needle labeled "longest identity" is used as the percent identity and is calculated as follows:

(Identical Residues×100)/(Length of Alignment− Number of Gaps in Alignment)

For purposes of the present invention, the degree of identity between two nucleotide sequences is determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EDNAFULL matrix. The output of Needle labeled "longest identity" is used as the percent identity and is calculated as follows:

(Identical Residues×100)/(Length of Alignment− Number of Gaps in Alignment)

Homologous sequence: The term "homologous sequence" is defined herein as a predicted protein which gives an E value (or expectancy score) of less than 0.001 in a fasts search (Pearson, W. R., 1999, in *Bioinformatics Methods and Protocols*, S. Misener and S. A. Krawetz, ed., pp. 185-219) with the mature endoglucanase of SEQ ID NO: 4, SEQ ID NO: 6, SEQ ID NO: 8, or SEQ ID NO: 10.

Polypeptide fragment: The term "polypeptide fragment" is defined herein as a polypeptide having one or more amino acids deleted from the amino and/or carboxyl terminus of the mature polypeptide of SEQ ID NO: 4, SEQ ID NO: 6, SEQ ID NO: 8, or SEQ ID NO: 10; or a homologous sequence thereof, wherein the fragment has endoglucanase activity. In a preferred aspect, a fragment contains at least 295 amino acid residues, more preferably at least 315 amino acid residues, and most preferably at least 335 amino acid residues of the mature polypeptide of SEQ ID NO: 4 or a homologous sequence thereof. In another preferred aspect, a fragment contains at least 320 amino acid residues, more preferably at least 340 amino acid residues, and most preferably at least 360 amino acid residues of the mature polypeptide of SEQ ID NO: 6 or a homologous sequence thereof. In another preferred aspect, a fragment contains at least 325 amino acid residues, more preferably at least 345 amino acid residues, and most preferably at least 365 amino acid residues of the mature polypeptide of SEQ ID NO: 8 or a homologous sequence thereof. In another preferred aspect, a fragment contains at least 335 amino acid residues, more preferably at least 355 amino acid residues, and most preferably at least 375 amino acid residues of the mature polypeptide of SEQ ID NO: 10 or a homologous sequence thereof.

Subsequence: The term "subsequence" is defined herein as a nucleotide sequence having one or more nucleotides deleted from the 5' and/or 3' end of the mature polypeptide coding sequence of SEQ ID NO: 3, SEQ ID NO: 5, SEQ ID NO: 7, or SEQ ID NO: 9; or a homologous sequence thereof; wherein the subsequence encodes a polypeptide fragment having endoglucanase activity. In a preferred aspect, a subsequence contains at least 885 nucleotides, more preferably at least 945 nucleotides, and most preferably at least 1005 nucleotides of the mature polypeptide coding sequence of SEQ ID NO: 3 or a homologous sequence thereof. In another preferred aspect, a subsequence contains at least 960 nucleotides, more preferably at least 1020 nucleotides, and most preferably at least 1080 nucleotides of the mature polypeptide coding sequence of SEQ ID NO: 5 or a homologous sequence thereof. In another preferred aspect, a subsequence contains at least 975 nucleotides, more preferably at least 1035 nucleotides, and most preferably at least 1095 nucleotides of the mature polypeptide coding sequence of SEQ ID NO: 7 or a homologous sequence thereof. In another preferred aspect, a subsequence contains at least 1005 nucleotides, more preferably at least 1065 nucleotides, and most preferably at least 1125 nucleotides of the mature polypeptide coding sequence of SEQ ID NO: 9 or a homologous sequence thereof.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide which is at least 20% pure, preferably at least 40% pure, more preferably at least 60% pure, even more preferably at least 80% pure, most preferably at least 90% pure, and even most preferably at least 95% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively or recombinantly associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, or recombinant nucleotide sequence.

Mature polypeptide coding sequence: The term "mature polypeptide coding sequence" is defined herein as a nucleotide sequence that encodes a mature polypeptide having endoglucanase activity.

cDNA: The term "cDNA" is defined herein as a DNA molecule which can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA which is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention, and which is operably linked to additional nucleotides that provide for its expression.

Host cell: The term "host cell", as used herein, includes any cell type which is susceptible to transformation, transfection, transduction, and the like with a nucleic acid construct or expression vector comprising a polynucleotide of the present invention.

Modification: The term "modification" means herein any chemical modification of the polypeptide consisting of the mature polypeptide of SEQ ID NO 4, SEQ ID NO: 6, SEQ ID NO: 8, or SEQ ID NO: 10; or a homologous sequence thereof; as well as genetic manipulation of the DNA encoding such a polypeptide. The modification can be substitutions, deletions and/or insertions of one or more amino acids as well as replacements of one or more amino acid side chains.

Artificial variant: When used herein, the term "artificial variant" means a polypeptide having endoglucanase activity produced by an organism expressing a modified nucleotide sequence of the mature polypeptide coding sequence of SEQ ID NO: 3, SEQ ID NO: 5, SEQ ID NO: 7, or SEQ ID NO: 9; or a homologous sequence thereof. The modified nucleotide sequence is obtained through human intervention by modification of the nucleotide sequence disclosed in SEQ ID NO: 3, SEQ ID NO: 5, SEQ ID NO: 7, or SEQ ID NO: 9; or a homologous sequence thereof.

DETAILED DESCRIPTION OF THE INVENTION

Polypeptides Having Endoglucanase Activity

In a first aspect, the present invention relates to isolated polypeptides comprising an amino acid sequence which has a degree of identity to the mature polypeptide of SEQ ID NO: 4, SEQ ID NO: 6, SEQ ID NO: 8, or SEQ ID NO: 10, of at least 60%, preferably at least 65%, more preferably at least 70%, more preferably at least 75%, more preferably at least 80%, more preferably at least 85%, even more preferably at least 90%, most preferably at least 95%, and even most preferably at least 96%, 97%, 98%, or 99%, which have endoglucanase activity (hereinafter "homologous polypeptides"). In a preferred aspect, the homologous polypeptides have an amino acid sequence which differs by ten amino acids, preferably by five amino acids, more preferably by four amino acids, even more preferably by three amino acids, most preferably by two amino acids, and even most preferably by one amino acid from the mature polypeptide of SEQ ID NO: 4, SEQ ID NO: 6, SEQ ID NO: 8, or SEQ ID NO: 10.

A polypeptide of the present invention preferably comprises the amino acid sequence of SEQ ID NO: 4 or an allelic variant thereof; or a fragment thereof that has endoglucanase activity. In a preferred aspect, a polypeptide comprises the amino acid sequence of SEQ ID NO: 4. In another preferred aspect, a polypeptide comprises the mature polypeptide of SEQ ID NO: 4. In another preferred aspect, a polypeptide comprises amino acids 17 to 389 of SEQ ID NO: 4, or an allelic variant thereof; or a fragment thereof that has endoglucanase activity. In another preferred aspect, a polypeptide comprises amino acids 17 to 389 of SEQ ID NO: 4. In another preferred aspect, a polypeptide consists of the amino acid sequence of SEQ ID NO 4 or an allelic variant thereof; or a fragment thereof that has endoglucanase activity. In another preferred aspect, a polypeptide consists of the amino acid sequence of SEQ ID NO: 4. In another preferred aspect, a polypeptide consists of the mature polypeptide of SEQ ID NO: 4. In another preferred aspect, a polypeptide consists of amino acids 17 to 389 of SEQ ID NO: 4 or an allelic variant thereof; or a fragment thereof that has endoglucanase activity. In another preferred aspect, a polypeptide consists of amino acids 17 to 389 of SEQ ID NO: 4.

A polypeptide of the present invention preferably also comprises the amino acid sequence of SEQ ID NO: 6 or an allelic variant thereof; or a fragment thereof that has endoglucanase activity. In a preferred aspect, a polypeptide comprises the amino acid sequence of SEQ ID NO: 6. In another preferred aspect, a polypeptide comprises the mature polypeptide of SEQ ID NO: 6. In another preferred aspect, a polypeptide comprises amino acids 16 to 397 of SEQ ID NO: 6, or an allelic variant thereof; or a fragment thereof that has endoglucanase activity. In another preferred aspect, a polypeptide comprises amino acids 16 to 397 of SEQ ID NO: 6. In another preferred aspect, a polypeptide consists of the amino acid sequence of SEQ ID NO: 6 or an allelic variant thereof; or a fragment thereof that has endoglucanase activity. In another preferred aspect, a polypeptide consists of the amino acid sequence of SEQ ID NO: 6. In another preferred aspect, a polypeptide consists of the mature polypeptide of SEQ ID NO: 6. In another preferred aspect, a polypeptide consists of amino acids 16 to 397 of SEQ ID NO: 6 or an allelic variant thereof; or a fragment thereof that has endoglucanase activity. In another preferred aspect, a polypeptide consists of amino acids 16 to 397 of SEQ ID NO: 6.

A polypeptide of the present invention preferably also comprises the amino acid sequence of SEQ ID NO: 8 or an allelic variant thereof; or a fragment thereof that has endoglucanase activity. In a preferred aspect, a polypeptide comprises the amino acid sequence of SEQ ID NO: 8. In another preferred aspect, a polypeptide comprises the mature polypeptide of SEQ ID NO: 8. In another preferred aspect, a polypeptide comprises amino acids 22 to 429 of SEQ ID NO: 8, or an allelic variant thereof; or a fragment thereof that has endoglucanase activity. In another preferred aspect, a polypeptide comprises amino acids 22 to 429 of SEQ ID NO: 8. In another preferred aspect, a polypeptide consists of the amino acid sequence of SEQ ID NO: 8 or an allelic variant thereof; or a fragment thereof that has endoglucanase activity. In another preferred aspect, a polypeptide consists of the amino acid sequence of SEQ ID NO: 8. In another preferred aspect, a polypeptide consists of the mature polypeptide of SEQ ID NO: 8. In another preferred aspect, a polypeptide consists of amino acids 22 to 429 of SEQ ID NO: 8 or an allelic variant thereof; or a fragment thereof that has endoglucanase activity. In another preferred aspect, a polypeptide consists of amino acids 22 to 429 of SEQ ID NO: 8.

A polypeptide of the present invention preferably also comprises the amino acid sequence of SEQ ID NO: 10 or an allelic variant thereof; or a fragment thereof that has endoglucanase activity. In a preferred aspect, a polypeptide comprises the amino acid sequence of SEQ ID NO: 10. In another preferred aspect, a polypeptide comprises the mature polypeptide of SEQ ID NO: 10. In another preferred aspect, a polypeptide comprises amino acids 25 to 421 of SEQ ID NO: 10, or an allelic variant thereof; or a fragment thereof that has endoglucanase activity. In another preferred aspect, a polypeptide comprises amino acids 25 to 421 of SEQ ID NO: 10. In another preferred aspect, a polypeptide consists of the amino acid sequence of SEQ ID NO: 10 or an allelic variant thereof; or a fragment thereof that has endoglucanase activity. In another preferred aspect, a polypeptide consists of the amino acid sequence of SEQ ID NO: 10. In another preferred aspect, a polypeptide consists of the mature polypeptide of SEQ ID NO: 10. In another preferred aspect, a polypeptide consists of amino acids 25 to 421 of SEQ ID NO: 10 or an allelic variant thereof; or a fragment thereof that has endoglucanase activity. In another preferred aspect, a polypeptide consists of amino acids 25 to 421 of SEQ ID NO: 10.

In a second aspect, the present invention relates to isolated polypeptides having endoglucanase activity which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 3, SEQ ID NO: 5, SEQ ID NO: 7, or SEQ ID NO: 9, (ii) the cDNA sequence contained in the mature polypeptide coding sequence of SEQ ID NO: 3 or SEQ ID NO: 9 or the genomic DNA sequence comprising the mature polypeptide coding sequence of SEQ ID NO: 5 or SEQ ID NO: 7, (iii) a subsequence of (i) or (ii), or (iv) a complementary strand of (i), (ii), or (iii) (J. Sambrook, E. F. Fritsch, and T, Maniatis, 1989, *Molecular Cloning, A Laboratory Manual,* 2d edition, Cold Spring Harbor, N.Y.). A subsequence of the mature polypeptide coding sequence of SEQ ID NO: 3, SEQ ID NO: 5, SEQ ID NO: 7, or SEQ ID NO: 9 contains at least 100 contiguous nucleotides or preferably at least 200 contiguous nucleotides. Moreover, the subsequence may encode a polypeptide fragment which has endoglucanase activity. In a preferred aspect, the mature polypeptide coding sequence is nucleotides 67 to 1185 of SEQ ID NO: 3. In another preferred aspect, the mature polypeptide coding sequence is nucleotides 84 to 1229 of SEQ ID NO: 5. In another preferred aspect, the mature polypeptide coding sequence is nucleotides 77 to 1300 of SEQ ID NO: 7. In another preferred aspect, the mature polypeptide coding sequence is nucleotides 73 to 1468 of SEQ ID NO: 9. In another preferred aspect, the complementary strand is the full-length complementary strand of the mature polypeptide coding sequence of SEQ ID NO: 3, SEQ ID NO: 5, SEQ ID NO: 7, or SEQ ID NO: 9.

The nucleotide sequence of SEQ ID NO: 3, SEQ ID NO: 5, SEQ ID NO: 7, or SEQ ID NO: 9; or a subsequence thereof; as well as the amino acid sequence of SEQ ID NO: 4, SEQ ID NO: 6, SEQ ID NO: 8, or SEQ ID NO: 10; or a fragment thereof; may be used to design a nucleic acid probe to identify and clone DNA encoding polypeptides having endoglucanase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene for example, with $^{32}P$, $^{3}H$, $^{35}S$, biotin, or avidin). Such probes are encompassed by the present invention.

A genomic DNA or cDNA library prepared from such other organisms may, therefore, be screened for DNA which hybridizes with the probes described above and which encodes a polypeptide having endoglucanase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO. 3, SEQ ID NO: 5, SEQ ID NO: 7, or SEQ ID NO: 9; or a subsequence thereof; the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 3, SEQ ID NO: 5, SEQ ID NO: 7, or SEQ ID NO: 9; the cDNA sequence contained in the mature polypeptide coding sequence of SEQ ID NO: 3 or SEQ ID NO: 9 or the genomic DNA sequence comprising the mature polypeptide coding sequence of SEQ ID NO: 5 or SEQ ID NO: 7; its complementary strand; or a subsequence thereof; under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO: 3. In another preferred aspect, the nucleic acid probe is nucleotides 67 to 1185 of SEQ ID NO: 3. In another preferred aspect, the nucleic acid probe is a polynucleotide sequence which encodes the polypeptide of SEQ ID NO: 4, or a subsequence thereof. In another preferred aspect, the nucleic acid probe is SEQ ID NO: 3. In another preferred aspect, the nucleic acid probe is the polynucleotide sequence contained in plasmid pCIC161 which is contained in *E. coli* NRRL B-30902, wherein the polynucleotide sequence thereof encodes a polypeptide having endoglucanase activity. In another preferred aspect, the nucleic acid probe is the mature polypeptide coding region contained in plasmid pCIC161 which is contained in *E. coli* NRRL 5-30902.

In another preferred aspect, the nucleic acid probe is the mature polypeptide coding sequence of SEQ ID NO: 5. In another preferred aspect, the nucleic acid probe is nucleotides 84 to 1229 of SEQ ID NO: 5. In another preferred aspect, the nucleic acid probe is a polynucleotide sequence which encodes the polypeptide of SEQ ID NO: 6, or a subsequence thereof. In another preferred aspect, the nucleic acid probe is SEQ ID NO: 5. In another preferred aspect, the nucleic acid probe is the polynucleotide sequence contained in plasmid pCIC453 which is contained in *E. coli* NRRL B-30903, wherein the polynucleotide sequence thereof encodes a polypeptide having endoglucanase activity. In another preferred aspect, the nucleic acid probe is the mature polypeptide coding region contained in plasmid pCIC453 which is contained in *E. coli* NRRL B-30903.

In another preferred aspect, the nucleic acid probe is the mature polypeptide coding sequence of SEQ ID NO: 7. In another preferred aspect, the nucleic acid probe is nucleotides 77 to 1300 of SEQ ID NO: 7. In another preferred aspect, the nucleic acid probe is a polynucleotide sequence which encodes the polypeptide of SEQ ID NO: 8, or a subsequence thereof. In another preferred aspect, the nucleic acid probe is SEQ ID NO: 7. In another preferred aspect, the nucleic acid probe is the polynucleotide sequence contained in plasmid pCIC486 which is contained in *E. coli* NRRL B-30904, wherein the polynucleotide sequence thereof encodes a polypeptide having endoglucanase activity. In another preferred aspect, the nucleic acid probe is the mature polypeptide coding region contained in plasmid pCIC486 which is contained in *E. coli* NRRL B-30904.

In another preferred aspect, the nucleic acid probe is the mature polypeptide coding sequence of SEQ ID NO: 9. In another preferred aspect, the nucleic acid probe is nucleotides 73 to 1468 of SEQ ID NO: 9. In another preferred aspect, the nucleic acid probe is a polynucleotide sequence which encodes the polypeptide of SEQ ID NO: 10, or a subsequence thereof. In another preferred aspect, the nucleic acid probe is SEQ ID NO: 9. In another preferred aspect, the nucleic acid probe is the polynucleotide sequence contained in plasmid pPBCel5C which is contained in *E. coli* NRRL B-30900N, wherein the polynucleotide sequence thereof encodes a polypeptide having endoglucanase activity. In another preferred aspect, the nucleic acid probe is the mature polypeptide coding region contained in plasmid pPBCel5C which is contained in *E. coli* NRRL B-30900N.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes which are about 15 nucleotides to about 70 nucleotides in length, the carrier material is washed once in 6×SCC plus 0.1% SOS for 15 minutes and twice each for 15 minutes using 6×SSC at 5° C. to 10° C. below the calculated In a third aspect, the present invention relates to isolated polypeptides encoded by polynucleotides comprising or consisting of nucleotide sequences which have a degree of identity to the mature polypeptide coding sequence of SEQ ID NO: 3, SEQ ID NO: 5, SEQ ID NO: 7, or SEQ ID NO: 9 of at least 60%, preferably at least 65%, more preferably at least 70%, more preferably at least 75%, more preferably at least 80%, more preferably at least 85%, more preferably at least 90%, even more preferably at least 95%, and most preferably at least 97% identity, which encode an active polypeptide. In a preferred aspect, the mature polypeptide coding sequence is nucleotides 67 to 1185 of SEQ ID NO: 3. In another preferred aspect, the mature polypeptide coding sequence is nucleotides 84 to 1229 of SEQ ID NO: 5. In another preferred aspect, the mature polypeptide coding sequence is nucleotides 77 to 1300 of SEQ ID NO: 7. In another preferred aspect, the mature polypeptide coding sequence is nucleotides 73 to 1468 of SEQ ID NO: 9. See polynucleotide section herein.

In a fourth aspect, the present invention relates to artificial variants comprising a substitution, deletion, and/or insertion of one or more amino acids of the mature polypeptide of SEQ ID NO: 4, SEQ ID NO: 6, SEQ ID NO: 8, or SEQ ID NO: 10; or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, *In, The Proteins*, Academic Press, New York. The most commonly occurring exchanges are Ala/Ser, Val/Ile Asp/Glu, Thr/Ser, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., endoglucanase activity) to identify amino acid residues that are critical to the activity of the molecule. See also, Hilton of et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904: Wlodaver et al., 1992, *FEBS Lett.* 309: 59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413, or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 4, SEQ ID NO: 6, SEQ ID NO: 8, or SEQ ID NO: 10, such as amino acids 17 to 389 of SEQ ID NO: 2, amino acids 16 to 397 of SEQ ID NO: 6, amino acids 22 to 429 of SEQ ID NO: 8, or amino acids 25 to 421 of SEQ ID NO; 10, is 10, preferably 9, more preferably 8, more preferably 7, more preferably at most 6, more preferably 5, more preferably 4, even more preferably 3, most preferably 2, and even most preferably 1.

Sources of Polypeptides Having Endoglucanase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide having endoglucanase activity of the present invention may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus*, or *Oceanobacillus* polypeptide having [enzyme] activity, or a Gram negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having endoglucanase activity.

In a preferred aspect, the polypeptide is a *Bacillus alkalaphilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megatenum, Bacillus pumilus, Bacillus stearothermophilus, Bacillus subtilis*, or *Bacillus thuringiensis* polypeptide having endoglucanase activity.

In another preferred aspect, the polypeptide is a *Streptococcus equisimilis, Streptococcus pyogenes, Streptococcus uberis*, or *Streptococcus equi* subsp. *Zooepidemicus* polypeptide having endoglucanase activity.

In another preferred aspect, the polypeptide is a *Streptomyces achromogenes, Streptomyces avermitilis, Streptomyces coelicolor, Streptomyces griseus*, or *Streptomyces lividans* polypeptide having endoglucanase activity.

A polypeptide having endoglucanase activity of the present invention may also be a fungal polypeptide, and more preferably a yeast polypeptide such as a *Candida, Kluyveromyces, Pichia, Saccharomyces, Schizosaccharomyces*, or *Yarrowia* polypeptide having endoglucanase activity; or more preferably a filamentous fungal polypeptide such as an *Acremonium, Aspergillus, Aureobasidium, Chrysosporium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, or *Trichoderma* polypeptide having endoglucanase activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having endoglucanase activity.

In another preferred aspect, the polypeptide is an *Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei*, or *Trichoderma viride* polypeptide having endoglucanase activity.

In another preferred aspect, the polypeptide is a *Penicillium brasilianum, Penicillium camembertii, Penicillium capsulatum, Penicillium chrysogenum, Penicillium citreonigrum, Penicillium citrinum, Penicillium claviforme, Penicillium corylophilum, Penicillium crustosum, Penicil-*

*lium digitatum, Penicillium expansum, Penicillium funiculosum, Penicillium glabrum, Penicillium granulatum, Penicillium griseofulvum, Penicillium islandicum, Penicillium italicum, Penicillium janthinellum, Penicillium lividum, Penicillium megasporum, Penicillium melinii, Penicillium notatum, Penicillium oxalicum, Penicillium puberulum, Penicillium purpurescens, Penicillium purpurogenum, Penicillium roquefortii, Penicillium rugulosum, Penicillium spinulosum, Penicillium waksmanii,* or *Penicillium* sp. polypeptide having endoglucanase activity.

In a more preferred aspect, the polypeptide is a *Myceliophthora thermophila* polypeptide, and most preferably a *Myceliophthora thermophila* CBS 111.65 polypeptide, e.g., the polypeptide of SEQ ID NO: 4, or the mature polypeptide thereof.

In another more preferred aspect, the polypeptide is a basidiomycete CBS 495.95 polypeptide, e.g., the polypeptide of SEQ ID NO: 6, or the mature polypeptide thereof.

In another more preferred aspect, the polypeptide is a basidiomycete CBS 494.95 polypeptide, e.g., the polypeptide of SEQ ID NO: 8, or the mature polypeptide thereof.

In another more preferred aspect, the polypeptide is a *Penicillium brasilianum* polypeptide, and most preferably a *Penicillium brasilianum* IBT 20888 polypeptide, e.g., the polypeptide of SEQ ID NO: 10, or the mature polypeptide thereof.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having endoglucanase activity from the fusion protein.

Examples of cleavage sites include, but are not limited to, a Kex2 site which encodes the dipeptide Lys-Arg (Martin of al., 2003, *J. Ind. Microbial. Biotechnol.* 3: 568-76; Svetina et al., 2000, *J. Biotechnol.* 76: 245-251; Rasmussen-Wilson et al., 1997, *Appl. Environ. Microbial.* 63: 3488-3493; Ward et al., 1995, *Biotechnology* 13: 498-503; and Contreras et al., 1991, *Biotechnology* 9: 378-381), an Ile-(Glu or Asp)-Gly-Arg site, which is cleaved by a Factor Xa protease after the arginine residue (Eaton et al., 1986, *Biochem.* 25: 505-512); a Asp-Asp-Asp-Asp-Lys site, which is cleaved by an enterokinase after the lysine (Collins-Racie et al., 1995, *Biotechnology* 13: 982-987); a His-Tyr-Glu site or His-Tyr-Asp site, which is cleaved by Genenase I (Carter et al. 1989, *Proteins: Structure, Function, and Genetics* 6: 240-248): a Leu-Val-Pro-Arg-Gly-Ser site, which is cleaved by thrombin after the Arg (Stevens, 2003, *Drug Discovery World* 4: 35-48): a Glu-Asn-Leu-Tyr-Phe-Gln-Gly site, which is cleaved by TEV protease after the Gln (Stevens, 2003, supra), and a Leu-Glu-Val-Leu-Phe-Gln-Gly-Pro site, which is cleaved by a genetically engineered form of human rhinovirus 3C protease after the Gln (Stevens, 2003, supra).

Polynucleotides

The present invention also relates to an isolated polynucleotide comprising or consisting of a nucleotide sequence which encodes a polypeptide of the present invention having endoglucanase activity.

In a preferred aspect, the nucleotide sequence comprises or consists of SEQ ID NO: 3. In another more preferred aspect, the nucleotide sequence comprises or consists of the sequence contained in plasmid pCIC161 which is contained in *E. coli* NRRL B-30902 In another preferred aspect, the nucleotide sequence comprises or consists of the mature polypeptide coding region of SEQ ID NO: 3. In another preferred aspect, the nucleotide sequence comprises or consists of nucleotides 67 to 1185 of SEQ ID NO: 3. In another more preferred aspect, the nucleotide sequence comprises or consists of the mature polypeptide coding region contained in plasmid pCIC161 which is contained in *E. coli* NRRL B-30902. The present invention also encompasses nucleotide sequences which encode polypeptides comprising or consisting of the amino acid sequence of SEQ ID NO: 4 or the mature polypeptide thereof, which differ from SEQ ID NO: 3 or the mature polypeptide coding sequence thereof by virtue of the degeneracy of the genetic code. The present invention also relates to subsequences of SEQ ID NO: 3 which encode fragments of SEQ ID NO: 4 that have endoglucanase activity.

In another preferred aspect, the nucleotide sequence comprises or consists of SEQ ID NO: 5. In another more preferred aspect, the nucleotide sequence comprises or consists of the sequence contained in plasmid pCIC453 which is contained in *E. coli* NRRL B-30903. In another preferred aspect, the nucleotide sequence comprises or consists of the mature polypeptide coding region of SEQ ID NO: 5. In another preferred aspect, the nucleotide sequence comprises or consists of nucleotides 84 to 1229 of SEQ ID NO: 5. In another more preferred aspect, the nucleotide sequence comprises or consists of the mature polypeptide coding region contained in plasmid pCIC453 which is contained in *E. coli* NRRL B-30903. The present invention also encompasses nucleotide sequences which encode polypeptides comprising or consisting of the amino acid sequence of SEQ ID NO: 6 or the mature polypeptide thereof, which differ from SEQ ID NO: 5 or the mature polypeptide coding sequence thereof by virtue of the degeneracy of the genetic code. The present invention also relates to subsequences of SEQ ID NO: 5 which encode fragments of SEQ ID NO: 6 that have endoglucanase activity.

In another preferred aspect, the nucleotide sequence comprises or consists of SEQ ID NO: 7. In another more preferred aspect, the nucleotide sequence comprises or consists of the sequence contained in plasmid pCIC486 which is contained in *E. coli* NRRL B-30904. In another preferred aspect, the nucleotide sequence comprises or consists of the mature polypeptide coding region of SEQ ID NO: 7. In another preferred aspect, the nucleotide sequence comprises or consists of nucleotides 77 to 1300 of SEQ ID NO: 7. In another more preferred aspect, the nucleotide sequence comprises or consists of the mature polypeptide coding region contained in plasmid pCIC486 which is contained in *E. coli* NRRL B-30904. The present invention also encompasses nucleotide sequences which encode polypeptides comprising or consisting of the amino acid sequence of SEQ ID NO: 8 or the mature polypeptide thereof, which differ from SEQ ID NO: 7 or the mature polypeptide coding sequence thereof by virtue of the degeneracy of the genetic code. The present invention also relates to subsequences of SEQ ID NO: 7 which encode fragments of SEQ ID NO: 8 that have endoglucanase activity.

In another preferred aspect, the nucleotide sequence comprises or consists of SEQ ID NO: 9. In another more preferred aspect, the nucleotide sequence comprises or consists of the sequence contained in plasmid pPBCel5C which is contained in *E. coli* NRRL B-30900N. In another preferred aspect, the nucleotide sequence comprises or consists of the mature polypeptide coding region of SEQ ID NO: 9. In another preferred aspect, the nucleotide sequence comprises or consists of nucleotides 73 to 1468 of SEQ ID NO: 9. In another more preferred aspect, the nucleotide sequence comprises or consists of the mature polypeptide coding region contained in plasmid pPBCel5C which is contained in *E. coli* NRRL B-30900N. The present invention also encompasses nucleotide sequences which encode polypeptides comprising or consisting of the amino acid sequence of SEQ ID NO: 10 or the mature polypeptide thereof, which differ from SEQ ID NO: 9 or the mature polypeptide coding sequence thereof by virtue of the degeneracy of the genetic code. The present invention also relates to subsequences of SEQ ID NO: 9 which encode fragments of SEQ ID NO: 10 that have endoglucanase activity.

The present invention also relates to mutant polynucleotides comprising or consisting of at least one mutation in the mature polypeptide coding sequence of SEQ ID NO: 3, SEQ ID NO: 5, SEQ ID NO: 7, or SEQ ID NO: 9, in which the mutant nucleotide sequence encodes the mature polypeptide of SEQ ID NO: 4, SEQ ID NO: 6, SEQ ID NO: 8, or SEQ ID NO: 10. In a preferred aspect, the mature polypeptide is amino acids 17 to 389 of SEQ ID NO: 4. In another preferred aspect, the mature polypeptide is amino acids 16 to 397 of SEQ ID NO: 6. In another preferred aspect, the mature polypeptide is amino acids 22 to 429 of SEQ ID NO: 8. In another preferred aspect, the mature polypeptide is amino acids 25 to 421 of SEQ ID NO: 10.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Myceliophthora thermophila* CBS 117.65, basidiomycete CBS 494.95, or basidiomycete CBS 495.95, or another or related organism and thus, for example, may be an allelic or species variant of the polypeptide encoding region of the nucleotide sequence.

The present invention also relates to isolated polynucleotides comprising or consisting of nucleotide sequences which have a degree of identity to the mature polypeptide coding sequence of SEQ ID NO: 3, SEQ ID NO: 5, SEQ ID NO: 7, or SEQ ID NO: 9 of at least 60%, preferably at least 65%, more preferably at least 70%, more preferably at least 75%, more preferably at least 80%, more preferably at least 85%, more preferably at least 90%, even more preferably at least 95%, and most preferably at least 97% identity, which encode an active polypeptide. In a preferred aspect, the mature polypeptide coding sequence is nucleotides 67 to 1185 of SEQ ID NO: 3. In another preferred aspect, the mature polypeptide coding sequence is nucleotides 84 to 1229 of SEQ ID NO: 5. In another preferred aspect, the mature polypeptide coding sequence is nucleotides 77 to 1300 of SEQ ID NO: 7. In another preferred aspect, the mature polypeptide coding sequence is nucleotides 73 to 1468 of SEQ ID NO: 9.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the polypeptide encoding region of SEQ ID NO: 3, SEQ ID NO: 5, SEQ ID NO: 7, or SEQ ID NO: 9, e.g., a subsequence thereof, and/or by introduction of nucleotide substitutions which do not give rise to another amino acid sequence of the polypeptide encoded by the nucleotide sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for endoglucanase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

The present invention also relates to isolated polynucleotides encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 3, SEQ ID NO: 5, SEQ ID NO: 7, or SEQ ID NO: 9, (ii) the cDNA sequence contained in the mature polypeptide coding sequence of SEQ ID NO; 3 or SEQ ID NO: 9 or the genomic DNA sequence comprising the mature polypeptide coding sequence of SEQ ID NO: 5 or SEQ ID NO: 7, or (iii) a complementary strand of (i) or (ii); or allelic variants and subsequences thereof (Sambrook et al., 1989, supra), as defined herein. In a preferred aspect, the mature polypeptide coding sequence of SEQ ID NO: 3 is nucleotides 67 to 1185. In another preferred aspect, the mature polypeptide coding sequence of SEQ ID NO: 5 is nucleotides 84 to 1229. In another preferred aspect, the mature polypeptide coding sequence of SEQ ID NO: 7 is nucleotides 77 to 1300. In another preferred aspect, the mature polypeptide coding sequence of SEQ ID NO: 9 is nucleotides 73 to 1768.

The present invention also relates to isolated polynucleotides obtained by (a) hybridizing a population of DNA under very low, low, medium, medium-high, high, or very high stringency conditions with (i) the mature polypeptide coding sequence of SEQ ID NO: 3, SEQ ID NO: 5, SEQ ID NO: 7, or SEQ ID NO: 9, (ii) the cDNA sequence contained in the mature polypeptide coding sequence of SEQ ID NO: 3 or SEQ ID NO: 9 or the genomic DNA sequence comprising the mature polypeptide coding sequence of SEQ ID NO: 5 or SEQ ID NO: 7, or (iii) a complementary strand of (i) or (ii); and (b) isolating the hybridizing polynucleotide, which encodes a polypeptide having endoglucanase activity. In a preferred aspect, the mature polypeptide coding sequence of SEQ ID NO: 3 is nucleotides 67 to 1185. In another preferred aspect, the mature polypeptide coding sequence of SEQ ID NO: 5 is nucleotides 84 to 1229. In another preferred aspect, the mature polypeptide coding sequence of SEQ ID NO: 7 is nucleotides 77 to 1300. In another preferred aspect, the mature polypeptide coding sequence of SEQ ID NO: 9 is nucleotides 73 to 1768.

Nucleic Acid Constructs

The present invention also relates to nucleic acid constructs comprising an isolated polynucleotide of the present invention operably linked to one or more control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et at, 1978, *Proceedings of the National Academy of Sciences USA* 75: 3727-3731), as well as the tac promoter (DeBoer et al., *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et at, 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et at 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice, i.e., secreted into a culture medium, may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993. *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

In a preferred aspect, the signal peptide comprises or consists of amino acids 1 to 16 of SEQ ID NO: 4. In another preferred aspect, the signal peptide coding region is nucleotides 19 to 69 of SEQ ID NO: 3.

In another preferred aspect, the signal peptide comprises or consists of amino acids 1 to 15 of SEQ ID NO: 6. In another preferred aspect, the signal peptide coding region comprises or consists of nucleotides 39 to 83 of SEQ ID NO: 5.

In another preferred aspect, the signal peptide comprises or consists of amino acids 1 to 21 of SEQ ID NO: 8. In another preferred aspect, the signal peptide coding region comprises or consists of nucleotides 14 to 76 of SEQ ID NO: 7.

In another preferred aspect, the signal peptide comprises or consists of amino acids 1 to 16 of SEQ ID NO: 10. In another preferred aspect, the signal peptide coding region comprises or consists of nucleotides 1 to 48 of SEQ ID NO: 9.

The control sequence may also be a propeptide coding region that codes for an amino acid sequence positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

In a preferred aspect, the propeptide comprises or consists of amino acids 17 to 24 of SEQ ID NO: 10. In another preferred aspect, the propeptide coding region comprises or consists of nucleotides 49 to 72 of SEQ ID NO: 9.

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector which may include one or more convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopius*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Research* 15: 9163-9175: WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The host cell may be any cell useful in the recombinant production of a polypeptide of the present invention, e.g., a prokaryote or a eukaryote.

The prokaryotic host cell may be any Gram positive bacterium or a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus*, and *Oceanobacillus*. Gram negative bacteria include, but not limited to. *E. coli, Pseudomonas, Salmonella, Campylobacter, Helicobacter, Flavobacterium, Fusobacterium, Ilyobacter, Neisseria*, and *Ureaplasma*.

The bacterial host cell may be any Bacillus cell, *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

In a preferred aspect, the bacterial host cell is a *Bacillus amyloliquefaciens, Bacillus lentus, Bacillus licheniformis, Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis. Streptococcus pyogenes, Streptococcus uberis,* and *Streptococcus equi* subsp. *Zooepidemicus.*

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes, Streptomyces avermitilis, Streptomyces coelicolor, Streptomyces griseus,* and *Streptomyces lividans.*

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988. *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol. (Praha)* 49: 399-405), by conjugation (see, e.g., Mazodier et al., 1989, *J. Bacteria* 171: 3583-3585), or by transduction (see, e.g., Burke et al., 2001, *Proc. Natl. Acad. Sci. USA* 98:6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbial.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-2070, by electroporation (see, e.g., Buckley et al., 1999, *Appl. Environ. Microbial.* 65: 3800-3804) or by conjugation (see, e.g., Clewell, 1981 *Microbial. Rev.* 45: 409-436). However, any method known in the for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., *In, Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfect (Blastomycetes). Since the classification of yeast may change in the future, for the purposes of this invention, yeast shall be defined as described in *Biology and Activities of Yeast* (Skinner, F. A., Passmore, S. M., and Davenport. R. R., ads, *Soc. App. Bacteriol. Symposium Series* No. 9, 1980), In an even more preferred aspect, the yeast host cell is a *Candida, Hansenula, Kluyveromyces, Pichia, Saccharomyces. Schizosaccharomyces,* or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysos-*

*porium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium brasilianum, Penicillium purpurogenum, Phanerochaete chrysosporium, Phlebia radiate, Pleurotus eryngii, Thielavia terrestris, Trametes villose, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors. *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention, comprising: (a) cultivating a cell, which in its wild-type form is capable of producing the polypeptide, under conditions conducive for production of the polypeptide; and (b) recovering the polypeptide. In a preferred aspect, the cell is of the genus *Myceliophthora*. In a more preferred aspect, the cell is *Myceliophthora thermophila*. In a most preferred aspect, the cell is *Myceliophthora thermophila* CBS 117.65. In another preferred aspect, the cell is basidiomycete CBS 494.95. In another preferred aspect, the cell is basidiomycete CBS 495.95. In another preferred aspect, the cell is of the genus *Penicillium*. In another more preferred aspect, the cell is *Penicillium brasilianum*. In another most preferred aspect, the cell is *Penicillium brasilianum* IBT 20888.

The present invention also relates to methods for producing a polypeptide of the present invention, comprising: (a) cultivating a host cell under conditions conducive for production of the polypeptide; and (b) recovering the polypeptide.

The present invention also relates to methods for producing a polypeptide of the present invention, comprising: (a) cultivating a host cell under conditions conducive for production of the polypeptide, wherein the host cell comprises a mutant nucleotide sequence having at least one mutation in the mature polypeptide coding sequence of SEQ ID NO: 3, SEQ ID NO: 5, SEQ ID NO: 7, or SEQ ID NO: 9, wherein the mutant nucleotide sequence encodes a polypeptide which comprises or consists of the mature polypeptide of SEQ ID NO: 4, SEQ ID NO: 6, SEQ. ID NO: 8, or SEQ ID NO: 10, and (b) recovering the polypeptide.

In a preferred aspect, the mature polypeptide of SEQ ID NO: 4 is amino acids 17 to 389. In another preferred aspect, the mature polypeptide of SEQ ID NO: 6 is amino acids 16 to 397. In another preferred aspect, the mature polypeptide of SEQ ID NO: 8 is amino acids 22 to 429. In another preferred aspect, the mature polypeptide of SEQ ID NO: 10 is amino acids 25 to 421. In another preferred aspect, the mature polypeptide coding sequence is nucleotides 67 to 1185 of SEQ ID NO: 3. In another preferred aspect, the mature polypeptide coding sequence is nucleotides 84 to 1229 of SEQ ID NO: 5 In another preferred aspect, the mature polypeptide coding sequence is nucleotides 77 to 1300 of SEQ ID NO: 7. In another preferred aspect, the mature polypeptide coding sequence is nucleotides 73 to 1468 of SEQ. ID NO: 9.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Plants

The present invention also relates to plants, e.g., a transgenic plant, plant part, or plant cell, comprising an isolated polynucleotide encoding a polypeptide having endoglucanase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as Festuca, Lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more expression constructs encoding a polypeptide of the present invention into the plant host genome or chloroplast genome and propagating the resulting modified plant or plant cell into a transgenic plant or plant cell.

The expression construct is conveniently a nucleic acid construct which comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mo. Biol.* 18: 675-689: Zhang et al, 1991 *Plant Cell* 3: 1155-1165), organ-specific promoters may be, for example, a promoter from storage sink tissues such as seeds, potato tubers, and fruits (Edwards & Coruzzi, 1990. *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the chlorella virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron which is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274), Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods for producing a polypeptide of the present invention comprising: (a) cultivating a transgenic plant or a plant cell comprising a polynucleotide encoding a polypeptide having endoglucanase activity of the present invention under conditions conducive for production of the polypeptide; and (b) recovering the polypeptide.

Removal or Reduction of Endoglucanase Activity

The present invention also relates to methods for producing a mutant of a parent cell, which comprises disrupting or deleting a polynucleotide sequence, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is inactivated. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence which is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred aspect, the nucleotide sequence is disrupted with a selectable marker such as those described herein.

Alternatively, modification or inactivation of the nucleotide sequence may be performed by established anti-sense or RNAi techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell which comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising: (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method for producing a protein product essentially free of endoglucanase activity by fermentation of a cell which produces both a polypeptide of the present invention as well as the protein product of interest by adding an effective amount of an agent capable of inhibiting endoglucanase activity to the fermentation broth before, during, or after the fermentation has been completed, recovering the product of interest from the fermentation broth, and optionally subjecting the recovered product to further purification.

In a further aspect, the present invention relates to a method for producing a protein product essentially free of endoglucanase activity by cultivating the cell under conditions permitting the expression of the product, subjecting the resultant culture broth to a combined pH and temperature treatment so as to reduce the endoglucanase activity substantially, and recovering the product from the culture broth. Alternatively, the combined pH and temperature treatment may be performed on an enzyme preparation recovered from the culture broth. The combined pH and temperature treatment may optionally be used in combination with a treatment with an endoglucanase inhibitor.

In accordance with this aspect of the invention, it is possible to remove at least 60%, preferably at least 75%, more preferably at least 85%, still more preferably at least 95%, and most preferably at least 99% of the endoglucanase activity. Complete removal of endoglucanase activity may be obtained by use of this method.

The combined pH and temperature treatment is preferably carried out at a pH in the range of 2-3 or 10-11 and a temperature in the range of at least 75-85° C. for a sufficient period of time to attain the desired effect, where typically, 1 to 3 hours is sufficient.

The methods used for cultivation and purification of the product of interest may be performed by methods known in the art.

The methods of the present invention for producing an essentially endoglucanase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The endoglucanase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from endoglucanase activity which is produced by a method of the present invention.

Methods of Inhibiting Expression of a Polypeptide

The present invention also relates to methods of inhibiting expression of a polypeptide in a cell, comprising administering to the cell or expressing in the cell a double-stranded RNA (dsRNA) molecule, wherein the dsRNA comprises a subsequence or portion of a polynucleotide of the present invention. In a preferred aspect, the dsRNA is about 15, 16, 17, 18, 19, 20, 21, 22, 23, 24, 25 or more duplex nucleotides in length. In another preferred aspect, the polypeptide has endoglucanase activity.

The dsRNA is preferably a small interfering RNA (siRNA) or a micro RNA (miRNA). In a preferred aspect, the dsRNA is small interfering RNA (siRNAs) for inhibiting transcription. In another preferred aspect, the dsRNA is micro RNA (miRNAs) for inhibiting translation.

The present invention also relates to such double-stranded RNA (dsRNA) molecules for inhibiting expression of a polypeptide in a cell, wherein the dsRNA comprises a subsequence or portion of a polynucleotide encoding the mature polypeptide of SEQ ID NO: 4, SEQ ID NO: 6, SEQ ID NO: 8, or SEQ ID NO: 10. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing therapeutics, in one aspect, the invention provides methods to selectively degrade RNA using the dsRNA is of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art, see, for example, U.S. Pat. No. 6,506,559; U.S. Pat. No. 6,511,824; U.S. Pat. No. 6,515,109; and U.S. Pat. No. 6,489,127.

Compositions

The present invention also relates to compositions comprising a polypeptide of the present invention. Preferably, the compositions are enriched in such a polypeptide. The term "enriched" indicates that the endoglucanase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, or *Aspergillus oryzae*; *Fusarium*, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, preferably *Humicola insolens* or *Humicola lanuginosa*; or *Trichoderma*, preferably *Trichoderma harzianum*, *Trichoderma koningii*, *Trichoderma longibrachiatum*, *Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention also relates to methods for degrading or converting a cellulosic material, comprising: treating the cellulosic material with a composition comprising an effective amount of a polypeptide having endoglucanase activity of the present invention. In a preferred aspect, the method further comprises recovering the degraded or converted cellulosic material.

The polypeptides and host cells of the present invention may be used in the production of monosaccharides, disaccharides, and polysaccharides as chemical or fermentation feedstocks from cellulosic biomass for the production of ethanol, plastics, other products or intermediates. The composition comprising the polypeptide having endoglucanase activity may be in the form of a crude fermentation broth with or without the cells removed or in the form of a semi-purified or purified enzyme preparation. The composition can also comprise other proteins and enzymes useful in the processing of biomass, e.g., cellobiohydrolase, beta-glucosidase, hemicellulolytic enzymes, enhancers (WO 2005/074647, WO 2005/074656), etc. Alternatively, the composition may comprise a host cell of the present invention as a source of the polypeptide having endoglucanase activity in a fermentation process with the biomass. In particular, the polypeptides and host cells of the present invention may be used to increase the value of processing residues (dried distillers grain, spent grains from brewing, sugarcane bagasse, etc.) by partial or complete degradation of cellulose or hemicellulose. The host cell may also contain native or heterologous genes that encode other proteins and enzymes, mentioned above, useful in the processing of biomass.

In the methods of the present invention, any cellulosic material, such as biomass, can be used. It is understood herein that the term "cellulosic material" encompasses lignocellulose. Biomass can include, but is not limited to, wood resources, municipal solid waste, wastepaper, crops, and crop residues (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40. Springer-Verlag, New York).

The predominant polysaccharide in the primary cell wall of biomass is cellulose, the second most abundant is hemi-cellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Three major classes of enzymes are used to breakdown cellulosic biomass:
(1) The "endo-1,4-beta-glucanases" or 1,4-beta-D-glucan-4-glucanohydrolases (EC 3.2.1.4), which act randomly on soluble and insoluble 1,4-beta-glucan substrates.
(2) The "exo-1,4-beta-D-glucanases" including both the 1,4-beta-D-glucan glucohydrolases (EC 3.2.1.74), which liberate D-glucose from 1,4-beta-D-glucans and hydrolyze D-cellobiose slowly, and cellobiohydrolases (1,4-beta-D-glucan cellobiohydrolases, EC 3.2.1.91), which liberate D-cellobiose from 1,4-beta-glucans.
(3) The "beta-D-glucosidases" or beta-D-glucoside glucohydrolases (EC 3.2.1.21), which act to release D-glucose units from cellobiose and soluble cellodextrins, as well as an array of glycosides.

The polypeptides having endoglucanase activity of the present invention are preferably used in conjunction with other cellulolytic proteins, e.g., exo-1,4-beta-D-glucanases and beta-D-glucosidases, to degrade the cellulose component of the biomass substrate, (see, for example, Brigham et al., 1995, in *Handbook on Bioethanol* (Charles E. Wyman, editor), pp. 119-141 Taylor & Francis, Washington D.C., Lee, 1997, *Journal of Biotechnology* 56: 1-24).

The exo-1,4-beta-D-glucanases and beta-D-glucosidases may be produced by any known method known in the art (see, e.g., Bennett, J. W. and LaSure, L. (eds.), *More Gene Manipulations in Fungi*, Academic Press, CA, 1991).

The optimum amounts of a polypeptide having endoglucanase activity and other cellulolytic proteins depends on several factors including, but not limited to, the mixture of component cellulolytic proteins, the cellulosic substrate, the concentration of cellulosic substrate, the pretreatment(s) of the cellulosic substrate, temperature, time, pH, and inclusion of fermenting organism (e.g., yeast for Simultaneous Saccharification and Fermentation). The term "cellulolytic proteins" is defined herein as those proteins or mixtures of proteins shown as being capable of hydrolyzing or converting or degrading cellulose under the conditions tested.

In a preferred aspect, the amount of polypeptide having endoglucanase activity per g of cellulosic material is about 0.5 to about 50 mg, preferably about 0.5 to about 40 mg, more preferably about 0.5 to about 25 mg, more preferably about 0.75 to about 20 mg, more preferably about 0.5 to about 15 mg, even more preferably about 0.5 to about 10 mg, and most preferably about 2.5 to about 10 mg per g of cellulosic material, In another preferred aspect, the amount of cellulolytic proteins per g of cellulosic material is about 0.5 to about 50 mg, preferably about 0.5 to about 40 mg, more preferably about 0.5 to about 25 mg, more preferably about 0.75 to about 20 mg, more preferably about 0.75 to about 15 mg, even more preferably about 0.5 to about 10 mg, and most preferably about 2.5 to about 10 mg per g of cellulosic material.

In the methods of the present invention, the composition may be supplemented by one or more additional enzyme activities to improve the degradation of the cellulosic material. Preferred additional enzymes are hemicellulases, esterases (e.g., lipases, phospholipases, and/or cutinases), proteases, laccases, peroxidases, or mixtures thereof.

In the methods of the present invention, the additional enzyme(s) may be added prior to or during fermentation, including during or after the propagation of the fermenting microorganism(s).

The enzymes may be derived or obtained from any suitable origin, including, bacterial, fungal, yeast or mammalian origin. The term "obtained" means herein that the enzyme may have been isolated from an organism which naturally produces the enzyme as a native enzyme. The term "obtained" also means herein that the enzyme may have been produced recombinantly in a host organism, wherein the recombinantly produced enzyme is either native or foreign to the host organism or has a modified amino acid sequence, e.g., having one or more amino acids which are deleted, inserted and/or substituted, i.e., a recombinantly produced enzyme which is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

The enzymes may also be purified. The term "purified" as used herein covers enzymes free from other components from the organism from which it is derived. The term "purified" also covers enzymes free from components from the native organism from which it is obtained. The enzymes may be purified, with only minor amounts of other proteins being present. The expression "other proteins" relate in particular to other enzymes. The term "purified" as used herein also refers to removal of other components, particularly other proteins and most particularly other enzymes present in the cell of origin of the enzyme of the invention. The enzyme may be "substantially pure," that is, free from other components from the organism in which it is produced, that is, for example, a host organism for recombinantly produced enzymes. In a preferred aspect, the enzymes are at least 75% (w/w), preferably at least 80%, more preferably at least 85%, more preferably at least 90%, more preferably at least 95%, more preferably at least 96%, more preferably at least 97%, even more preferably at least 98%, or most preferably at least 99% pure. In another preferred aspect, the enzyme is 100% pure.

The enzymes used in the present invention may be in any form suitable for use in the processes described herein, such as, for example, a crude fermentation broth with or without cells, a dry powder or granulate, a non-dusting granulate, a liquid, a stabilized liquid, or a protected enzyme. Granulates may be produced, e.g., as disclosed in U.S. Pat. Nos. 4,106, 991 and 4,661,452, and may optionally be coated by process known in the art. Liquid enzyme preparations may, for instance, be stabilized by adding stabilizers such as a sugar, a sugar alcohol or another polyol, and/or lactic acid or another organic acid according to established process. Protected enzymes may be prepared according to the process disclosed in EP 238,216.

The methods of the present invention may be used to process a cellulosic material to many useful organic products, chemicals and fuels. In addition to ethanol, some commodity and specialty chemicals that can be produced from cellulose include xylose, acetone, acetate, glycine, lysine, organic acids (e.g., lactic acid), 1,3-propanediol, butanediol, glycerol, ethylene glycol, furfural, polyhydroxyalkanoates, cis, cis-muconic acid, and animal feed (Lynd, L. R., Wyman, C. E., and Gerngross, T. U., 1999. *Biocommodity Engineering, Biotechnol. Prog.*, 15: 777-793; Philippidis, G. P., 1996. Cellulose bioconversion technology, in *Handbook on Bioethanol: Production and Utilization*, Wyman, C. E., ed., Taylor & Francis, Washington, D.C., 179-212; and Ryu, D. D. Y., and Mandels, M., 1980, Cellulases: biosynthesis and applications, *Enz. Microb. Technol.*, 2: 91-102). Potential coproduction benefits extend beyond the synthesis of multiple organic products from fermentable carbohydrate. Lignin-rich residues remaining after biological processing can be converted to lignin-derived chemicals, or used for power production.

Conventional methods used to process the cellulosic material in accordance with the methods of the present invention are well understood to those skilled in the art. The methods of the present invention may be implemented using any conventional biomass processing apparatus configured to operate in accordance with the invention.

Such an apparatus may include a batch-stirred reactor, a continuous flow stirred reactor with ultrafiltration, a continuous plug-flow column reactor (Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K, and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Proles, O. V., 1996, Enhancement of enzymatic cellulose hydrolysis using a novel type of bioreactor with intensive stirring induced by electromagnetic field, *Appl. Biochem. Biotechnol.* 56: 141-153).

The conventional methods include, but are not limited to, saccharification, fermentation, separate hydrolysis and fermentation (SHF), simultaneous saccharification and fermentation (SSF), simultaneous saccharification and cofermentation (SSCF), hybrid hydrolysis and fermentation (HHF), and direct microbial conversion (DMC).

SHF uses separate process steps to first enzymatically hydrolyze cellulose to glucose and then ferment glucose to ethanol. In SSF, the enzymatic hydrolysis of cellulose and the fermentation of glucose to ethanol is combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF includes the cofermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF includes two separate steps carried out in the same reactor but at different temperatures, i.e., high temperature enzymatic saccharification followed by SSF at a lower temperature that the fermentation strain can tolerate, DMC combines all three processes (cellulase production, cellulose hydrolysis, and fermentation) in one step (Lynd, L. R., Weimer, P. J., van Zyl, W. H., and Pretorius, I. S., 2002, Microbial cellulose utilization: Fundamentals and biotechnology, *Microbial. Mol. Biol. Reviews* 66: 506-577).

"Fermentation" or "fermentation process" refers to any fermentation process or any process comprising a fermentation step. A fermentation process includes, without limitation, fermentation processes used to produce fermentation products including alcohols (e.g., arabinitol, butanol, ethanol, glycerol, methanol, 1,3-propanediol, sorbitol, and xylitol) organic acids (e.g., acetic acid, acetonic acid, adipic acid, ascorbic acid, citric acid, 2,5-diketo-D-gluconic acid, formic acid, fumaric acid, glucaric acid, gluconic add, glucuronic acid, glutaric acid, 3-hydroxypropionic acid, itaconic acid, lactic acid, malic acid, malonic acid, oxalic acid, propionic acid, succinic acid, and xylonic acid); ketones (e.g., acetone); amino acids (e.g., aspartic acid, glutamic acid, glycine, lysine, serine, and threonine); gases (e.g., methane, hydrogen ($H_2$), carbon dioxide ($CO_2$), and carbon monoxide (CO)). Fermentation processes also include fermentation processes used in the consumable alcohol industry (e.g., beer and wine), dairy industry (e.g., fermented dairy products), leather industry, and tobacco industry.

The present invention further relates to methods of producing a substance, comprising: (a) saccharifying a cellulosic material with a composition comprising an effective amount of a polypeptide having endoglucanase activity; (b) fermenting the saccharified cellulosic material of step (a) with one or more fermentating microorganisms; and (c) recovering the substance from the fermentation. The composition comprising the polypeptide having endoglucanase activity may be in the form of a crude fermentation broth with or without the cells removed or in the form of a semi-purified or purified enzyme preparation or the composition may comprise a host cell of the present invention as a source of the polypeptide having endoglucanase activity in a fermentation process with the biomass.

The substance can be any substance derived from the fermentation. In a preferred embodiment, the substance is an alcohol. It will be understood that the term "alcohol" encompasses a substance that contains one or more hydroxyl moieties. In a more preferred embodiment, the alcohol is arabinitol. In another more preferred embodiment, the alcohol is butanol. In another more preferred embodiment, the alcohol is ethanol. In another more preferred embodiment, the alcohol is glycerol. In another more preferred embodiment, the alcohol is methanol. In another more preferred embodiment, the alcohol is 1,3-propanediol. In another more preferred embodiment, the alcohol is sorbitol. In another more preferred embodiment, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002. The biotechnological production of sorbitol, *Appl. Microbiol. Biotechnol.* 59: 400-

408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred embodiment, the substance is an organic acid. In another more preferred embodiment, the organic acid is acetic acid. In another more preferred embodiment, the organic acid is acetonic acid. In another more preferred embodiment, the organic acid is adipic acid. In another more preferred embodiment, the organic acid is ascorbic acid. In another more preferred embodiment, the organic acid is citric acid. In another more preferred embodiment, the organic acid is 2,5-diketo-D-gluconic acid. In another more preferred embodiment, the organic acid is formic acid. In another more preferred embodiment, the organic acid is fumaric acid. In another more preferred embodiment, the organic acid is glucaric acid, in another more preferred embodiment, the organic acid is gluconic acid. In another more preferred embodiment, the organic acid is glucuronic acid. In another more preferred embodiment, the organic acid is glutaric acid. In another preferred embodiment, the organic acid is 3-hydroxypropionic acid. In another more preferred embodiment, the organic acid is itaconic acid. In another more preferred embodiment, the organic acid is lactic acid. In another more preferred embodiment, the organic acid is malic acid. In another more preferred embodiment, the organic acid is malonic acid. In another more preferred embodiment, the organic acid is oxalic acid. In another more preferred embodiment, the organic acid is propionic acid. In another more preferred embodiment, the organic acid is succinic acid. In another more preferred embodiment, the organic acid is xylonic acid. See, for example, Chen, R., and Lee, Y. Y., 1997, Membrane-mediated extractive fermentation for lactic acid production from cellulosic biomass, *Appl. Biochem, Biotechnol.* 63-65: 435-448.

In another preferred embodiment, the substance is a ketone. It will be understood that the term "ketone" encompasses a substance that contains one or more ketone moieties. In another more preferred embodiment, the ketone is acetone. See, for example, Qureshi and Blaschek, 2003, supra.

In another preferred embodiment, the substance is an amino acid. In another more preferred embodiment, the organic acid is aspartic acid. In another more preferred embodiment, the amino acid is glutamic acid. In another more preferred embodiment, the amino acid is glycine. In another more preferred embodiment, the amino acid is lysine. In another more preferred embodiment, the amino acid is serine. In another more preferred embodiment, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred embodiment, the substance is a gas. In another more preferred embodiment, the gas is methane. In another more preferred embodiment, the gas is $H_2$. In another more preferred embodiment, the gas is $CO_2$. In another more preferred embodiment, the gas is CO. See, for example, Kataoka, N., A. Miya, and K. Kiriyama, 1997. Studies on hydrogen production by continuous culture system of hydrogen-producing anaerobic bacteria, *Water Science and Technology* 36 (6-7); 41-47; and Gunaseelan V. N. in *Biomass and Bioenergy*, Vol. 13 (1-2), pp. 83-114, 1997, Anaerobic digestion of biomass for methane production: A review.

Production of a substance from cellulosic material typically requires four major steps. These four steps are pretreatment, enzymatic hydrolysis, fermentation, and recovery. Exemplified below is a process for producing ethanol, but it will be understood that similar processes can be used to produce other substances, for example, the substances described above.

Pretreatment. In the pretreatment or pre-hydrolysis step, the cellulosic material is heated to break down the lignin and carbohydrate structure, solubilize most of the hemicellulose, and make the cellulose fraction accessible to cellulolytic enzymes. The heating is performed either directly with steam or in slurry where a catalyst may also be added to the material to speed up the reactions. Catalysts include strong acids, such as sulfuric acid and $SO_2$, or alkali, such as sodium hydroxide. The purpose of the pre-treatment stage is to facilitate the penetration of the enzymes and microorganisms. Cellulosic biomass may also be subject to a hydrothermal steam explosion pre-treatment (See U.S. Patent Application No. 20020164730), Saccharification. In the enzymatic hydrolysis step, also known as saccharification, enzymes as described herein are added to the pretreated material to convert the cellulose fraction to glucose and/or other sugars. The saccharification is generally performed in stirred-tank reactors or fermenters under controlled pH, temperature, and mixing conditions. A saccharification step may last up to 200 hours. Saccharification may be carried out at temperatures from about 30° C. to about 65° C., in particular around 50° C., and at a pH in the range between about 4 and about 5, especially around pH 4.5. To produce glucose that can be metabolized by yeast, the hydrolysis is typically performed in the presence of a beta-glucosidase.

Fermentation. In the fermentation step, sugars, released from the cellulosic material as a result of the pretreatment and enzymatic hydrolysis steps, are fermented to ethanol by a fermenting organism, such as yeast. The fermentation can also be carried out simultaneously with the enzymatic hydrolysis in the same vessel, again under controlled pH, temperature, and mixing conditions. When saccharification and fermentation are performed simultaneously in the same vessel, the process is generally termed simultaneous saccharification and fermentation or SSF.

Any suitable cellulosic substrate or raw material may be used in a fermentation process of the present invention. The substrate is generally selected based on the desired fermentation product, i.e., the substance to be obtained from the fermentation, and the process employed, as is well known in the art. Examples of substrates suitable for use in the methods of present invention include cellulose-containing materials, such as wood or plant residues or low molecular sugars DP1-3 obtained from processed cellulosic material that can be metabolized by the fermenting microorganism, and which may be supplied by direct addition to the fermentation medium.

The term "fermentation medium" will be understood to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism suitable for use in a desired fermentation process. Suitable fermenting microorganisms according to the invention are able to ferment, i.e., convert, sugars, such as glucose, xylose, arabinose, mannose, galactose, or oligosaccharides directly or indirectly into the desired fermentation product. Examples of fermenting microorganisms include fungal organisms, such as yeast. Preferred yeast includes strains of the *Saccharomyces* spp., and in particular, *Saccharomyces cerevisiae*. Commercially available yeast include, e.g., Red Star®/™/Lesaffre Ethanol Red (available from Red Star/Lesaffre, USA) FALI (available from Fleischmann's Yeast, a division of Burns Philp Food Inc., USA), SUPERSTART (available from Alltech), GERT STRAND (available from Gert Strand AB, Sweden) and FERMIOL (available from DSM Specialties).

In a preferred embodiment, the yeast is a *Saccharomyces* spp. In a more preferred embodiment, the yeast is *Saccharomyces cerevisiae*. In another more preferred embodiment, the yeast is *Saccharomyces distaticus*. In another more preferred embodiment, the yeast is *Saccharomyces uvarum*. In another preferred embodiment, the yeast is a *Kluyveromyces*. In another more preferred embodiment, the yeast is *Kluyveromyces marxianus*. In another more preferred embodiment, the yeast is *Kluyveromyces fragilis*. In another preferred embodiment, the yeast is a *Candida*. In another more preferred embodiment, the yeast is *Candida pseudotropicalis*. In another more preferred embodiment, the yeast is *Candida brassicae*. In another preferred embodiment, the yeast is a *Clavispora*. In another more preferred embodiment, the yeast is *Clavispora lusitaniae*. In another more preferred embodiment, the yeast is *Clavispora opuntiae*. In another preferred embodiment, the yeast is a *Pachysolen*. In another more preferred embodiment, the yeast is *Pachysolen tannophilus*. In another preferred embodiment, the yeast is a *Bretannomyces*. In another more preferred embodiment, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment glucose to ethanol include, for example. *Zymomonas mobilis* and *Clostridium thermocellurn* (Philippidis, 1996, supra).

It is well known in the art that the organisms described above can also be used to produce other substances, as described herein.

The cloning of heterologous genes in *Saccharomyces cerevisiae* (Chen, Z., Ho, N. W. Y., 1993, Cloning and improving the expression of *Pichia stipitis* xylose reductase gene in *Saccharomyces cerevisiae, Appl. Biochem. Biotechnol.* 39-40: 135-147; Ho, N. W. Y., Chen, Z. Brainard, A. P., 1998, Genetically engineered *Saccharomyces* yeast capable of effectively cofermenting glucose and xylose, *Appl. Environ. Microbiol.* 64: 1852-1859), or in bacteria such as *Escherichia coli* (Beall, D. S., Ohta, K., Ingram, L. O., 1991, Parametric studies of ethanol production from xylose and other sugars by recombinant *Escherichia coli, Biotech. Bioeng*, 38: 296-303), *Klebsiella oxytoca* (Ingram, L. O., Gomes, P. F., Lai, X., Moniruzzaman, M., Wood, B. E., Yomano, L. P., York, S. W., 1998, Metabolic engineering of bacteria for ethanol production, *Biotechnol. Bioeng.* 58: 204-214), and *Zymomonas mobilis* (Zhang, M., Eddy, C., Deanda, K., Finkelstein, M., and Picataggio, S., 1995, Metabolic engineering of a pentose metabolism pathway in ethanologenic *Zymomonas mobilis, Science* 267: 240-243, Deanda, K., Zhang, M., Eddy, C., and Picataggio, S., 1996, Development of an arabinose-fermenting *Zymomonas mobilis* strain by metabolic pathway engineering, *Appl. Environ. Microbiol,* 62: 4465-4470) has led to the construction of organisms capable of converting hexoses and pentoses to ethanol (cofermentation).

Yeast or another microorganism typically is added to the degraded cellulose or hydrolysate and the fermentation is ongoing for about 24 to about 96 hours, such as about 35 to about 60 hours. The temperature is typically between about 26° C. to about 40° C., in particular at about 32° C., and at about pH 3 to about pH 6, in particular around pH 4-5.

In a preferred embodiment, yeast or another microorganism is applied to the degraded cellulose or hydrolysate and the fermentation is ongoing for about 24 to about 96 hours, such as typically 35-60 hours. In a preferred embodiments, the temperature is generally between about 26 to about 40° C., in particular about 32° C., and the pH is generally from about pH 3 to about pH 6, preferably around pH 4-5. Yeast or another microorganism is preferably applied in amounts of approximately $10^5$ to $10^{12}$, preferably from approximately $10^7$ to $10^{10}$, especially approximately $5 \times 10^7$ viable count per ml of fermentation broth. During an ethanol producing phase the yeast cell count should preferably be in the range from approximately $10^7$ to $10^{10}$, especially around approximately $2 \times 10^8$. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

The most widely used process in the art is the simultaneous saccharification and fermentation (SSF) process where there is no holding stage for the saccharification, meaning that yeast and enzyme are added together.

For ethanol production, following the fermentation the mash is distilled to extract the ethanol. The ethanol obtained according to the process of the invention may be used as, e.g., fuel ethanol; drinking ethanol, i.e., potable neutral spirits, or industrial ethanol.

A fermentation stimulator may be used in combination with any of the enzymatic processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, e.g., Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Recovery. The alcohol is separated from the fermented cellulosic material and purified by conventional methods of distillation. Ethanol with a purity of up to about 96 vol. % ethanol can be obtained, which can be used as, for example, fuel ethanol, drinking ethanol, i.e., potable neutral spirits, or industrial ethanol.

For other substances, any method known in the art can be used including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, distillation, or extraction.

In the methods of the present invention, the polypeptide having endoglucanase activity and other cellulolytic protein(s) may be supplemented by one or more additional enzyme activities to improve the degradation of the cellulosic material. Preferred additional enzymes are hemicellulases, esterases (e.g., lipases, phospholipases, and/or cutinases), proteases, laccases, peroxidases, or mixtures thereof.

In the methods of the present invention, the additional enzyme(s) may be added prior to or during fermentation, including during or after the propagation of the fermenting microorganism(s).

Propeptide and Signal Peptides

The present invention also relates to nucleic acid constructs comprising a gene encoding a protein, wherein the gene is operably linked to one or both of a first nucleotide sequence encoding a signal peptide comprising or consisting of amino acids 1 to 16 of SEQ ID NO: 4, amino acids 1 to 15 of SEQ ID NO: 6, amino acids 1 to 21 of SEQ ID NO: 8, or amino acids 1 to 16 of SEQ ID NO: 10 and a second nucleotide sequence encoding a propeptide comprising or consisting of amino acids 17 to 24 of SEQ ID NO: 10, wherein the gene is foreign to the first and second nucleotide sequences In a preferred aspect, the first nucleotide sequence comprises or consists of nucleotides 19 to 69 of SEQ ID NO: 3. In another preferred aspect, the first nucleotide sequence comprises or consists of nucleotides 39 to 83 of SEQ ID NO: 5. In another preferred aspect, the first nucleotide sequence comprises or consists of nucleotides 14 to 76 of SEQ ID NO: 7. In another preferred aspect, the first nucleotide sequence comprises or consists of nucleotides 1 to 48 of SEQ ID NO: 9. In another preferred aspect, the second nucleotide sequence comprises or consists of nucleotides 49 to 72 of SEQ ID NO: 9.

The present invention also relates to recombinant expression vectors and recombinant host cells comprising such nucleic acid constructs.

The present invention also relates to methods for producing a protein comprising (a) cultivating such a recombinant host cell under conditions suitable for production of the protein; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples which should not be construed as limiting the scope of the invention.

EXAMPLES

Materials

Chemicals used as buffers and substrates were commercial products of at least reagent grade.

Strains

*Myceliophthora thermophila* CBS 117.65, basidiomycete CBS 494.95, basidiomycete CBS 495.95, and *Penicillium brasilianum* strain IBT 20888 (IBT Culture Collection of Fungi, Technical University of Denmark, Copenhagen, Denmark) were used as sources of the endoglucanase genes. *Saccharomyces cerevisiae* strain W3124 (MATa; ura 3-52; leu 2-3, 112; his 3-D200; pep 4-1137: prc1::HIS3; prb1::LEU2; cir$^+$) was used for screening of *Myceliophthora thermophila* CBS 117.65 expression libraries for endoglucanase activity. *Aspergillus oryzae* HowB104 (alpha-amylase-negative) was used for expression of the cel5a genes.

Media and Solutions

LB medium was composed per liter of 10 g of tryptone, 5 g of yeast extract, and 5 g of sodium chloride.

LB ampicillin medium was composed per liter of 10 g of tryptone, 5 g of yeast extract, 5 g of sodium chloride, and 50 μg of ampicillin per ml (filter sterilized, added after autoclaving).

LB ampicillin plates were composed per liter of LB ampicillin medium and 15 g of bacto agar.

YPD medium was composed of 1% yeast extract, 2% peptone, and filter-sterilized 2% glucose added after autoclaving.

YPM medium was composed of 1% yeast extract, 2% peptone, and filter-sterilized 2% maltodextrin added after autoclaving.

SC-URA medium with galactose was composed per liter of 100 ml of 10× Basal salts, 28 ml of 20% casamino acids without vitamins, 10 ml of 1% tryptophan, 3.6 ml of 5% threonine (filter sterilized, added after autoclaving), and 100 ml of 20% galactose (filter sterilized, added after autoclaving).

SC-URA medium with glucose was composed per liter of 100 ml of 10× Basal salts solution, 28 ml of 20% casamino acids without vitamins, 10 ml of 1% tryptophan, 3.6 ml of 5% threonine (filter sterilized, added after autoclaving), and 100 ml of 20% glucose (filter sterilized, added after autoclaving).

10× Basal salts solution was composed per liter of 75 g of yeast nitrogen base, 113 g of succinic acid, and 68 g of NaOH.

SC-agar was composed per liter of SC-URA medium (with glucose or galactose as indicated) and 20 g of agar.

0.1% AZCL HE cellulose SC agar plates with galactose were composed per liter of SC-URA medium with galactose, 20 g of agar, and 0.1% AZCL HE cellulose (Megazyme, Wicklow, Ireland).

BA medium was composed per liter of 10 g of corn steep liquor dry matter, 10 g of $NH_4NO_2$, 10 g of $KH_2PO_4$, 0.75 g of $MgSO_4 \cdot 7H_2O$, 0.1 ml of pluronic, and 0.5 g of $CaCO_3$. The pH was adjusted to 6.5 before autoclaving.

COVE plates were composed per liter of 342.3 g of sucrose, 25 g of Noble agar, 20 ml of COVE salts solution, 10 mM acetamide, and 20 mM CsCl. The solution was adjusted to pH 7.0 before autoclaving.

COVE salts solution was composed per liter of 26 g of KCl, 26 g of $MgSO_4 \cdot 7H_2O$, 76 g of $KH_2PO_4$, and 50 ml of COVE trace metals.

COVE trace metals solution was composed per liter of 0.04 g of $NaB_4O_7 \cdot 10H_2O$, 0.4 g of $CuSO_4 \cdot 5H_2O$, 1.2 g of $FeSO_4 \cdot 7H_2O$, 0.7 g of $MnSO_4 \cdot H_2O$, 0.8 g of $Na_2MoO_2 \cdot 2H_2O$, and 10 g of $ZnSO_4 \cdot 7H_2O$.

TE was composed of 10 mM Tris pH 7.4 and 0.1 mM EDTA.

Example 1

Construction of *Myceliophthora thermophila* CBS 117.65 cDNA Expression Libraries in *Saccharomyces cerevisiae*

*Myceliophthora thermophila* CBS 117.65 was cultivated in 200 ml of BA medium at 3° C. for five days at 200 rpm. Mycelia from the shake flask culture were harvested by filtering the contents through a funnel lined with Miracloth™ (CalBiochem, San Diego, Calif., USA). The mycelia were then sandwiched between two Miracloth™ pieces and blotted dry with absorbent paper towels. The mycelial mass was then transferred to Falcon 1059 plastic centrifuge tubes and frozen in liquid nitrogen. Frozen mycelia were stored in a –80° C. freezer until use.

The extraction of total RNA was performed with guanidinium thiocyanate followed by ultracentrifugation through a 5.7 M CsCl cushion, and isolation of poly(A)+RNA was carried out by oligo(dT)-cellulose affinity chromatography, using the procedures described in WO 94/14953.

Double-stranded cDNA was synthesized from 5 µg of poly (A)+ RNA by the RNase H method (Gubler and Hoffman, 1983, *Gene* 25: 263-269, Sambrook et al., 1989, *Molecular cloning: A laboratory manual*, Cold Spring Harbor lab, Cold Spring Harbor, N.Y., USA). The poly(A)$^+$ RNA (5 µg in 5 µl of DEPC (0.1% diethylpyrocarbonate)-treated water) was heated at 70° C. for 8 minutes in a pre-siliconized, RNase-free Eppendorf tube, quenched on ice, and combined in a final volume of 50 µl with reverse transcriptase buffer composed of 50 mM Tris-HCl, pH 8.3, 75 mM KCl, 3 mM MgCl$_2$, 10 mM dithiothreitol (DTT) (Bethesda Research Laboratories, Bethesda, Md., USA), 1 mM of dATP, dGTP and dTTP, and 0.5 mM 5-methyl-dCTP (Pharmacia, Uppsala, Sweden), 40 units of human placental ribonuclease inhibitor (RNasin, Promega, Madison, Wis., USA), 1.45 µg of oligo(dT)$_{18}$-Not I primer (Pharmacia), and 1000 units of SuperScript II RNase H reverse transcriptase (Bethesda Research Laboratories). First-strand cDNA was synthesized by incubating the reaction mixture at 45° C. for 1 hour. After synthesis, the mRNA: cDNA hybrid mixture was gel filtrated through a MicroSpin S-400 HR spin column (Pharmacia) according to the manufacturer's instructions.

After gel filtration, the hybrids were diluted in 250 µl of second strand buffer (20 mM Tris-HCl, pH 7.4, 90 mM KCl, 4.6 mM MgCl$_2$, 10 mM (NH$_4$)$_2$SO$_4$, 0.16 mM NAD) containing 200 µM of each dNTP, 60 units of *E. coli* DNA polymerase I (Pharmacia), 5.25 units of RNase H (Promega), and 15 units of *E. coli* DNA ligase (Boehringer Mannheim, Manheim, Germany). Second strand cDNA synthesis was performed by incubating the reaction tube at 16° C. for 2 hours and an additional 15 minutes at 25° C. The reaction was stopped by addition of EDTA to a final concentration of 20 mM followed by phenol and chloroform extractions.

The double-stranded cDNA was precipitated at –20° C. for 12 hours by addition of 2 volumes of 96% ethanol and 0.2 volume of 10 M ammonium acetate, recovered by centrifugation at 13,000×g, washed in 70% ethanol, dried, and resuspended in 30 µl of Mung bean nuclease buffer (30 mM sodium acetate pH 4.6, 300 mM NaCl, 1 mM ZnSO$_4$, 0.35 mM DTT, 2% glycerol) containing 25 units of Mung bean nuclease (Pharmacia). The single-stranded hair-pin DNA was clipped by incubating the reaction at 30° C. for 30 minutes, followed by addition of 70 µl of 10 mM Tris-HCl-1 mM EDTA pH 7.5, phenol extraction, and precipitation with 2 volumes of 96% ethanol and 0.1 volume of 3 M sodium acetate pH 5.2 on ice for 30 minutes.

The double-stranded cDNAs were recovered by centrifugation at 13,000×g and blunt-ended in 30 µl of T4 DNA polymerase buffer (20 mM Tris-acetate, pH 7.9, 10 mM magnesium acetate, 50 mM potassium acetate, 1 mM DTT) containing 0.5 mM of each dNTP and 5 units of T4 DNA polymerase (New England Biolabs, Ipswich, Mass., USA) by incubating the reaction mixture at 16° C. for 1 hour. The reaction was stopped by addition of EDTA to a final concentration of 20 mM, followed by phenol and chloroform extractions, and precipitation for 12 hours at –20° C. by adding 2 volumes of 96% ethanol and 0.1 volume of 3 M sodium acetate pH 5.2.

After the fill-in reaction the cDNAs were recovered by centrifugation at 13,000×g, washed in 70% ethanol, and dried, The cDNA pellet was resuspended in 25 µl of ligation buffer (30 mM Tris-HCl, pH 7.8, 10 mM MgCl$_2$, 10 mM DTT, 0.5 mM ATP) containing 2.5 µg of non-palindromic Bst XI adaptors (Invitrogen, Carlsbad, Calif., USA), shown below, and 30 units of T4 ligase (Promega), and then incubated at 16° C. for 12 hours. The reaction was stopped by heating at 65° C. for 20 minutes and then cooled on ice for 5 minutes.

```
5'-CTTTCCAGCACA-3'      (SEQ ID NO: 1)

3'-GAAAGGTC-5'          (SEQ ID NO. 2)
```

The adapted cDNA was digested with Not I, followed by incubation for 2.5 hours at 37° C. The reaction was stopped by heating at 65° C. for 10 minutes. The cDNAs were size-fractionated by gel electrophoresis on a 0.8% SeaPlaque GTG low melting temperature agarose gel (Cambrex Corporation, East Rutherford, N.J., USA) in 44 mM Tris Base, 44 mM boric acid, 0.5 mM EDTA (TBE) buffer to separate unligated adaptors and small cDNAs. The cDNA was size-selected with a cut-off at 0.7 kb and rescued from the gel by use of β-Agarase (New England Biolabs, Ipswich, Mass., USA) according to the manufacturer's instructions and precipitated for 12 hours at –20° C. by adding two volumes of 96% ethanol and 0.1 volume of 3 M sodium acetate pH 5.2.

The directional, size-selected cDNA was recovered by centrifugation at 13,000×g, washed in 70% ethanol, dried, and then resuspended in 30 µl of 10 mM Tris-HCl-1 mM EDTA pH 7.5. The cDNAs were desalted by gel filtration through a MicroSpin S-300 HR spin column according to the manufacturers instructions. Three test ligations were carried out in 10 µl of ligation buffer (30 mM Tris-HCl, pH 7.8, 10 mM MgCl$_2$, 10 mM DTT, 0.5 mM ATP) containing 5 µl of double-stranded cDNA (reaction tubes #1 and #2), 15 units of T4 ligase (Promega), and 30 ng (tube #1), 40 ng (tube #2), and 40 ng (tube #3, the vector background control) of Bst XI-Not I cleaved pYES2.0 vector (Invitrogen, Carlsbad, Calif., USA). The ligation reactions were performed by incubation at 16° C. for 12 hours, then heating at 70° C. for 20 minutes, and finally adding 10 µl of water to each tube. One µl of each ligation mixture was electroporated into 40 µl of electrocompetent *E. coli* DH10B cells (Bethesda Research Laboratories) as described by Sambrook et al., 1989, supra.

The *Myceliaphthora thermophila* CBS 117.65 cDNA library was established in *E. coli* DH10B consisting of pools. Each pool was made by spreading transformed *E. coli* on LB ampicillin plates, yielding 15,000-30,000 colonies/plate after incubation at 37° C. for 24 hours. Twenty ml of LB ampicillin medium was added to the plate and the cells were suspended therein. The cell suspension was shaken at 100 rpm in a 50 ml tube for 1 hour at 37° C.

The resulting *Myceliophthora thermophila* CBS 117.65 cDNA library consisted of approximately $10^6$ individual clones, with a vector background of 1%. Plasmid DNA from some of the library pools was isolated using a Plasmid Midi Kit (QIAGEN Inc., Valencia, Calif., USA), according to the manufacturer's instructions, and stored at −20° C., Example 2

Screening of *Myceliophthora thermophila* CBS 117.65 Expression Libraries for Endoglucanase Activity One ml aliquots of purified plasmid DNA (100 ng/ml) from some of the library pools (Example 1) were transformed into *Saccharomyces cerevisiae* W3124 by electroporation (Becker and Guarante, 1991, *Methods Enzymol.* 194: 182-187) and the transformants were plated on SC agar containing 2% glucose and incubated at 30° C. In total, 50-100 plates containing 250-400 yeast colonies were obtained from each pool.

After 3-5 days of incubation, the SC agar plates were replica plated onto a set of 0.1% AZCL HE cellulose SC URA agar plates with galactose. The plates were incubated for 2-4 days at 30° C. and endoglucanase positive colonies were identified as colonies surrounded by a blue halo.

Example 3

Characterization of the *Myceliophthora thermophila* CBS 117.65 cel5a Gene

Endoglucanase-expressing yeast colonies were inoculated into 20 ml of YPD medium in 50 ml glass test tubes. The tubes were shaken at 200 rpm for 2 days at 30° C. The cells were harvested by centrifugation for 10 minutes at 3000 rpm in a Heraeus Megafuge 1.0R centrifuge with a 75002252 rotor (Hanau, Germany).

DNA was isolated according to WO 94/14953 and dissolved in 50 μl of deionized water. The DNA was transformed into *E. coli* DH10B cells by standard procedures according to Sambrook et al., 1989, supra. One *E. coli* transformant subsequently shown to contain the *Myceliophthora thermophila* CBS 117.65 cel5a gene was designated pCIC161 (FIG. 1) and used as the material for deposit of biological material. *E. coli* strain pCIC161 was deposited as *E. coli* NRRL B-30902 on Feb. 23, 2006.

Plasmid DNA was isolated from the *E. coli* transformants using standard procedures according to Sambrook et al., 1989, supra. The full length cDNA sequence of the cel5a gene from *Myceliophthora thermophila* CBS 117.65 was sequenced with a Taq DyeDeoxy Terminator Cycle Sequencing Kit (Perkin Elmer, Wellesley, Mass., USA) and synthetic oligonucleotide primers using an Applied Biosystems ABI PRISM™ 377 DNA Sequencer (ABI, Foster City, Calif., USA) according to the manufacturer's instructions.

The nucleotide sequence (SEQ ID NO: 3) and deduced amino acid sequence (SEQ ID NO: 4) of the *Myceliophthora thermophila* cel5a gene are shown in FIG. 2. The coding sequence is 1170 bp including the stop codon. The encoded predicted protein contains 389 amino acids. The % G+C of the coding region of the gene is 63.6% and the mature polypeptide coding region is 63.6%. Using the SignalP program, version 3 (Nielsen et al., 1997, *Protein Engineering* 10: 1-6), a signal peptide of 16 residues was predicted. The predicted mature protein contains 373 amino acids with a molecular mass of 40.9 kDa.

Analysis of the deduced amino acid sequence of the cel5a gene with the Interproscan program (Zdobnov and Apweiler, 2001, *Bioinformatics* 17: 847-848) showed that the CEL5A protein contained the core sequence typical of a Family 5 glycosyl hydrolase, extending from approximately amino acid residue 77 to residue 350 of the predicted mature polypeptide. The CEL5A protein also contained the sequence signature of a type I fungal cellulose binding domain (CBMI). This sequence signature known as Prosite pattern PS00562 (Sigrist et al., 2002, *Brief Bioinform.* 3: 265-274) was present from amino acid residue 8 to residue 35 of the predicted mature polypeptide.

A comparative pairwise global alignment of amino acid sequences was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Myceliophthora thermophila* gene encoding the CEL5A mature polypeptide shared 75% and 72% identity (excluding gaps) to the deduced amino acid sequences of two Family 5 glycosyl hydrolase proteins from *Neurospora crassa* and *Humicola insolens*, respectively (accession numbers Q7SDR1 and Q12624, respectively).

Example 4

Expression of *Myceliophthora thermophila* CBS 117.65 cel5a Gene in *Aspergillus oryzae*

Figure 3:
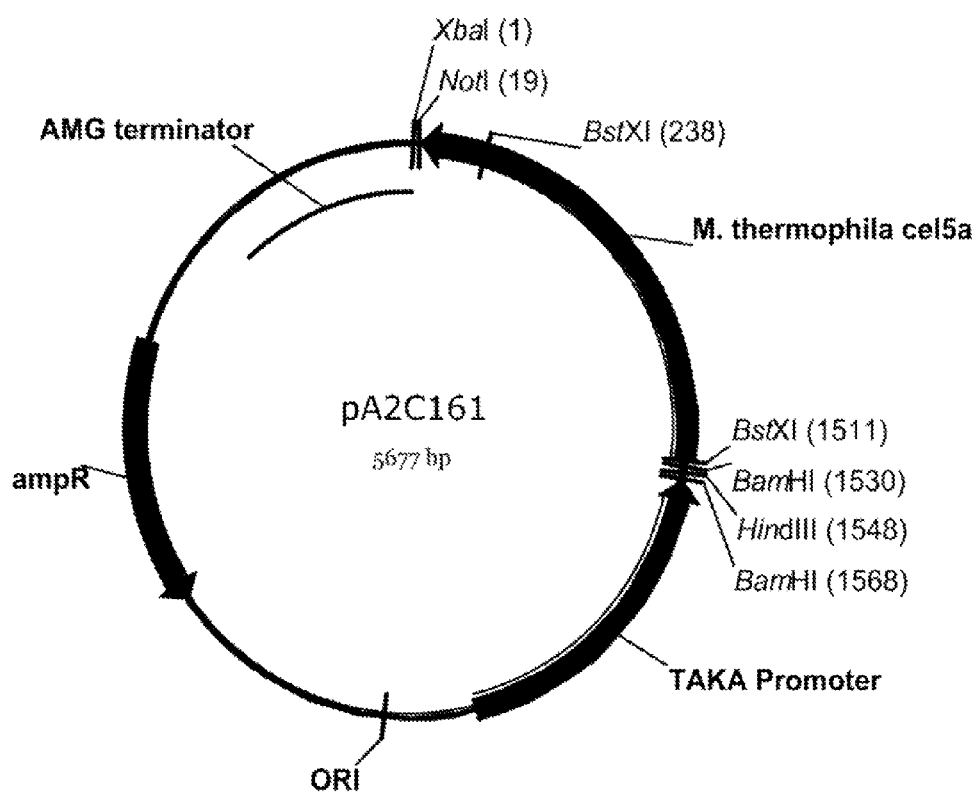
FIG. 3 shows a restriction map of pA2C161.

The *Myceliophthora thermophila* CBS 117.65 cel5a gene was excised from the pYES2.0 vector using Hind III and Xba I, and ligated into the *Aspergillus* expression vector pHD414 (EP 238 023, WO 93/11249) using standard methods (Sambrook et al., 1989, supra). The *Aspergillus* expression vector pHD414 is a derivative of p775 (EP 238 023). The resulting plasmid was designated pA2C161 (FIG. 3), Protoplasts of *Aspergillus oryzae* HowB104 were prepared as described in WO 95/02043. One hundred microliters of protoplast suspension was mixed with 5-25 μg of the *Aspergillus* expression vector pA2C161 in 10 μl of STC composed of 1.2 M sorbitol, 10 mM Tris-HCl, pH 7.5, 10 mM CaCl$_2$) and further mixed with 5-25 μg of p3SR2, an *Aspergillus nidulans* amdS gene carrying plasmid (Christensen et al., 1988, *Bio/Technology* 6: 1419-1422). The mixture was left at room temperature for 25 minutes. Two hundred microliters of 60% PEG 4000 (BDH, Poole, England) (polyethylene glycol, molecular weight 4,000), 10 mM CaCl$_2$, and 10 mM Tris-HCl pH 7.5 was added and gently mixed and finally 0.85 ml of the same solution was added and gently mixed. The mixture was left at room temperature for 25 minutes, centrifuged at 2,500×g for 15 minutes, and the pellet was resuspended in 2 ml of 1.2 M sorbitol. This sedimentation process was repeated, and the protoplasts were spread on COVE plates. After incubation for 4-7 days at 37° C. spores were picked and spread in order to isolate single colonies. This procedure was repeated and spores of a single colony after the second reisolation were stored.

Each of the transformants was inoculated in 10 ml of YPM medium. After 2-5 days of incubation at 30° C., 200 rpm, the supernatant was removed. Endoglucanase activity was identified by applying 20 μl of culture broth to 4 mm diameter holes punched out in a 0.1% AZCL HE cellulose SC-agar plate and incubation overnight at 30° C. Endoglucanase activity was then identified by a blue halo around a colony. Several transformant broths had endoglucanase activity significantly greater than broth from an untransformed *Aspergillus oryzae* background control, which demonstrated efficient expression of the CEL5A endoglucanase from *Myceliophthora thermophila* CBS 117.65 in *Aspergillus oryzae*.

Example 5

Construction of a Basidiomycete CBS 495.95 cDNA Expression Library in *Saccharomyces cerevisiae*

A cDNA library from basidiomycete CBS 495.95, consisting of approximately $10^6$ individual clones was constructed in *E. coli* as described in Example 1, with a vector background of 1%.

Example 6

Screening of Basidiomycete CBS 495.95 cDNA Expression Libraries for Endoglucanase Activity The screening of the cDNA library (Example 5) was performed as described in Example 2.

Example 7

Characterization of a CEL5A Encoding Gene from Basidiomycete CBS 495.95

Figure 4:
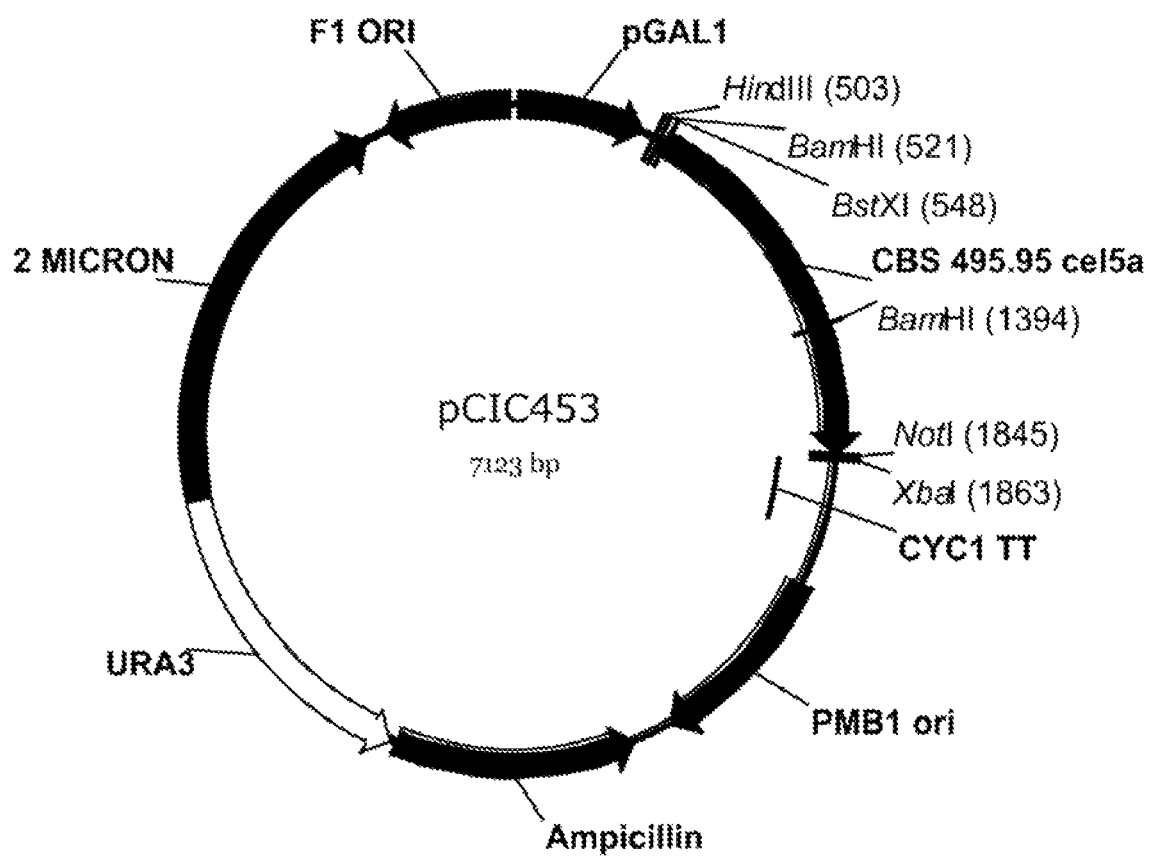
FIG. 4 shows a restriction map of pCIC453.

Cloning of the cel5a gene from basidiomycete CBS 495.95 was carried out as described in Example 3. One *E. coli* transformant subsequently shown to contain a cel5a gene was designated pCIC453 (FIG. 4) and used as the material for deposit of biological material. *E. coli* strain pCIC453 was deposited as *E. coli* NRRL B-30903 on Feb. 23, 2006.

Figure 5:
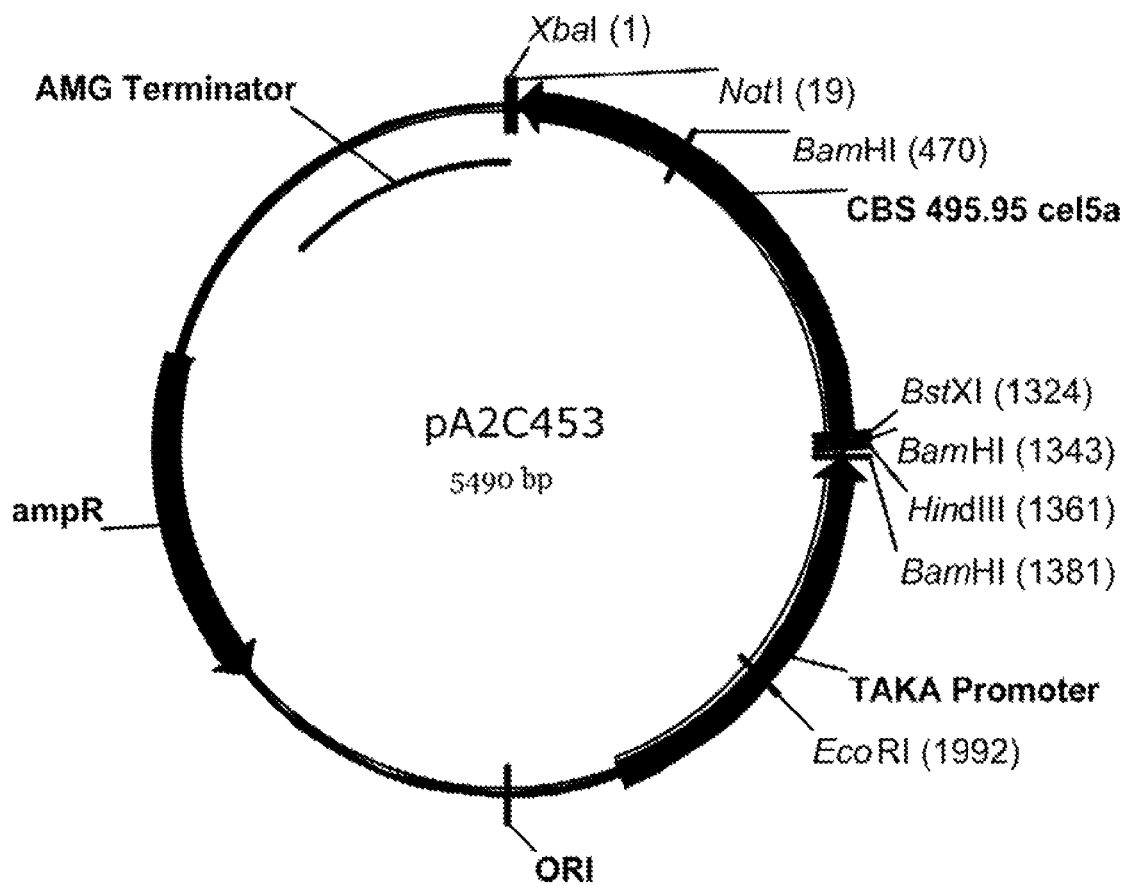
FIG. 5 shows a restriction map of pA2C453.

The basidiomycete CBS 495.95 cel5a gene was excised from pCIC453 using Hind III and Xba I and ligated into the *Aspergillus* expression vector pHD414. The resulting plasmid was designated pA2C453 (FIG. 5).

The nucleotide sequence (SEQ ID NO: 5) and deduced amino acid sequence (SEQ ID NO 6) of the CBS 495.95 cel5a gene are shown in FIG. 6. The coding sequence is 1194 bp including the stop codon. The % G+C of the coding region of the gene is 59.8% and the mature polypeptide coding region is 60.1%, The encoded predicted protein contains 397 amino acids. Using the SignalP program, version 3 (Nielsen et al., 1997, supra), a signal peptide of 15 residues was predicted. The predicted mature protein contains 382 amino acids with a molecular mass of 40.1 kDa.

Analysis of the deduced amino acid sequence of the cel5a gene with the Interproscan program (Zdobnov and Apweiler, 2001, supra) showed that the CEL5A protein contained the core sequence typical of a Family 5 glycosyl hydrolase, extending from approximately residues 81 to 359 of the predicted mature polypeptide. The CEL5A protein also contained the sequence signature of a type I fungal cellulose binding domain (CBMI). This sequence signature known as Prosite pattern PS00562 (Sigrist et al., 2002, supra) was present from amino acid residue 8 to residue 36 of the predicted mature polypeptide.

A comparative pairwise global alignment of amino acid sequences was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the CBS 495.95 gene encoding the CEL5A mature polypeptide shared 82% and 79% identity (excluding gaps) to the deduced amino acid sequences of two Family 5 glycosyl hydrolase proteins from *Irpex lacteus* and *Trametes hirsuta*, respectively (accession numbers Q5W7K4 and Q75UV6, respectively).

Example 8

Expression of cel5a Gene from Basidiomycete CBS 495.95 in *Aspergillus oryzae*

Expression of the cel5a gene from basidiomycete CBS 495.95, and analysis of endoglucanase activity was performed as described in Example 4.

Example 9

Construction of a Basidiomycete CBS 494.95 cDNA Expression Library in *Saccharomyces cerevisiae*

A cDNA library from basidiomycete CBS 494.95, consisting of approximately $10^6$ individual clones was constructed in *E. coli* as described in Example 1, with a vector background of 1%.

Example 10

Screening of Basidiomycete CBS 494.95 cDNA Expression Libraries for Endoglucanase Activity The screening of the cDNA library (Example 9) was performed as described in Example 2.

Example 11

Characterization of a CEL5B Encoding Gene from Basidiomycete CBS 494.95

Figure 7:
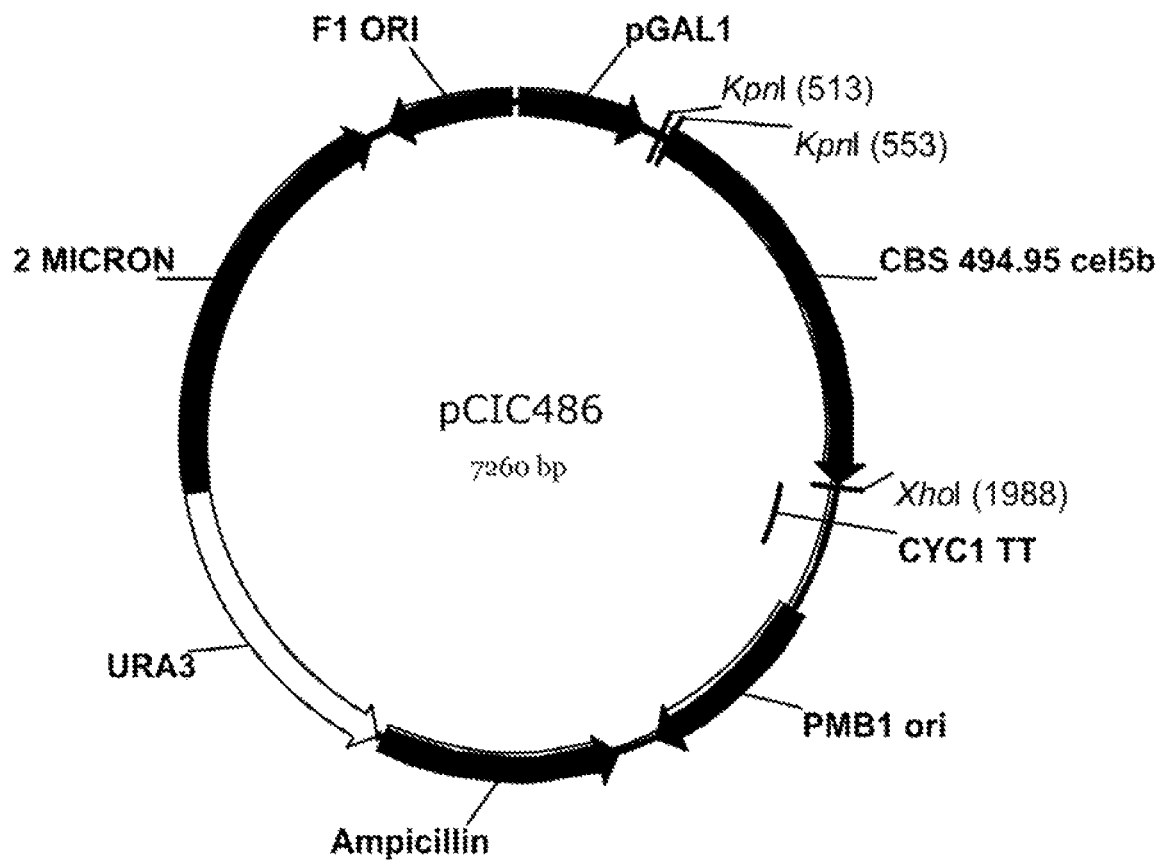
FIG. 7 shows a restriction map of pCIC486.

Cloning of the cel5b gene from basidiomycete CBS 494.95 was carried out as described in Example 3. One *E. coli* transformant subsequently shown to contain the CBS 494.95 cel5b gene was designated pCIC486 (FIG. 7) and used as the material for deposit of biological material. *E. coli* strain pCIC486 was deposited as *E. coli* NRRL B-30904 on Feb. 23, 2006.

Figure 8:
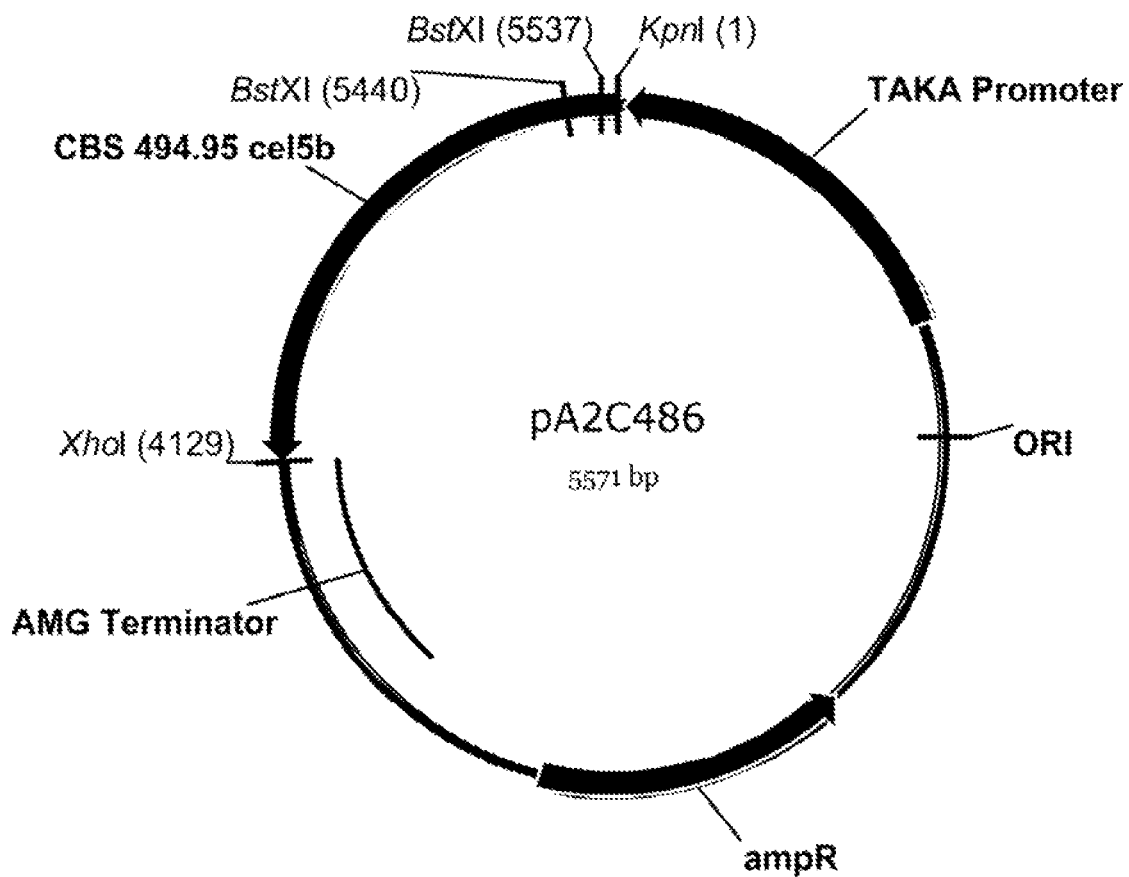
FIG. 8 shows a restriction map of pA2C486.

The basidiomycete CBS 494.95 cel5b gene was excised from the pYES2.0 vector using Kpn I and Xho I and ligated into the *Aspergillus* expression vector pHD423 (Lassen et al., 2001, *Appl Environ Microbiol* 67: 4701-4707), a pHD414 derivative with a Kpn I site in the polylinker. The resulting plasmid was designated pA2C486 (FIG. 8). The nucleotide sequence (SEQ ID NO: 7) and deduced amino acid sequence (SEQ ID NO: 8) of the CBS 494.95 cel5b gene are shown in FIG. 9. The coding sequence is 1290 bp including the stop codon. The % G+C of the coding region of the gene is 56.0% G+C and the mature polypeptide coding region is 56.1%. The encoded predicted protein contains 429 amino acids. Using the SignalP program, version 3 (Nielsen et al., 1997, supra), a signal peptide of 21 residues was predicted. The predicted mature protein contains 408 amino acids with a molecular mass of 43.1 kDa.

Analysis of the deduced amino acid sequence of the cel5b gene with the Interproscan program (Zdobnov and Apweiler, 2001, supra) showed that the CEL5B protein contained the core sequence typical of a Family 5 glycosyl hydrolase, extending from approximately amino acid residue 106 to residue 385 of the predicted mature polypeptide. The CEL5A protein also contained the sequence signature of a type I fungal cellulose binding domain (CBMI). This sequence signature known as Prosite pattern PS00562 (Sigrist et al., 2002, supra) was present from amino acid residue 7 to residue 34 of the predicted mature polypeptide.

A comparative pairwise global alignment of amino acid sequences was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the CBS 495.95 gene encoding the CEL5A mature polypeptide shared 69% and 67% identity (excluding gaps) to the deduced amino acid sequences of two Family 5 glycosyl hydrolase proteins from *Irpex lacteus* and *Trametes hirsuta*, respectively (accession numbers Q5W7K4 and Q75UV6, respectively).

Example 12

Expression of CEL5B from Basidiomycete CBS 494.95 in *Aspergillus oryzae*

Expression of the cel5B gene from basidiomycete CBS 494.95, and analysis of endoglucanase activity was performed as described in Example 4.

Example 13

Purification of Recombinant Endoglucanase from *Myceliophthora thermophila* CBS 117.65, Basidiomycete CBS 494.95, and Basidiomycete CBS 495.95

The endoglucanases from *Myceliophthora thermophila* CBS 117.65, basidiomycete CBS 494.95, and basidiomycete CBS 495.95, produced recombinantly in *Aspergillus oryzae* as described in Examples 4, 8, and 12, were purified to homogeneity using a protocol essentially as described by Otzen et 1999, *Protein Sci.* 8: 1878-87.

Protein concentration in the enzyme preparations was determined using the Bicinchoninic acid (BCA) Microplate Assay according to the manufacturer's instructions for a BCA Protein Assay Reagent Kit (Pierce Chemical Co., Rockford, Ill., USA), Enzyme dilutions were prepared fresh before each experiment from stock enzyme solutions, which were stored at –20° C.

Example 14

Isolation of Genomic DNA from *Penicillium brasilianum* IBT 20888

Spores of *Penicillium brasilianum* strain IBT 20888 were propagated on rice according to Carlsen, 1994, Ph.D. thesis, Department of Biotechnology, The Technical University of Denmark. The spores were recovered with 20 ml of 0.1% Tween 20 and inoculated at a concentration of $1 \times 10^6$ spores per ml into 100 ml of Mandels and Weber medium (Mandels and Weber, 1969, *Adv. Chem. Ser.* 95: 394-414) containing 1% glucose supplemented per liter with 0.25 g of yeast extract and 0.75 g of Bactopeptone in a 500 ml baffled shake flask. The fungal mycelia were harvested after 24 hours of aerobic growth at 30° C., 150 rpm.

Mycelia were collected by filtration through a Nalgene DS0281-5000 filter (Nalge Nunc International Corporation, Rochester, N.Y., USA) until dryness and frozen in liquid nitrogen. The frozen mycelia were ground to a powder in a dry ice chilled mortar and distributed to a screw-cap tube. The powder was suspended in a total volume of 40 ml of 50 mM CAPS (3-(cyclohexylamino)-1-propanesulfonic add)-NaOH pH 11 buffer containing 0.5% lithium dodecyl sulfate and 0.5 mM EDTA. The suspension was placed at 60° C. for 2 hours and periodically resuspended by inversion. To the suspension was added an equal volume of phenol:chloroform (1:1 v/v) neutralized with 0.1 M Tris base, and the tube was mixed on a rotating wheel at 37° C. for 2 hours. After centrifugation at 2500 rpm for 10 minutes in a Sorvall H1000B rotor, the aqueous phase (top phase) was re-extracted again with phenol:chloroform (1:1 v/v) and centrifuged at 15,000×g for 5 minutes. The aqueous phase from the second extraction was brought to 2.5 M ammonium acetate (stock 10 M) and placed at –20° C. until frozen. After thawing, the extract was centrifuged at 15,000×g for 20 minutes in a cold rotor. The pellet (primarily rRNA) was discarded and the nucleic acids in the supernatant were precipitated by addition of 0.7 volumes of isopropanol. After centrifugation at 15,000×g for 15 minutes, the pellet was rinsed three times with 5 ml of 70% ethanol (without resuspension), air-dried almost completely, and dissolved in 1.0 ml of 0.1×TE. The dissolved pellet was transferred to two 1.5 ml microfuges tubes. The nucleic acids were precipitated by addition of ammonium acetate (0.125 ml) to 2.0 M and ethanol to 63% (1.07 ml) and centrifuged at maximum speed for 10 minutes in a Sorvall MC 12V microcentrifuge (Kendro Laboratory Products, Asheville, N.C., USA). The pellet was rinsed twice with 70% ethanol, air-dried completely, and dissolved in 500 µl of 0.1×TE.

Example 15

Preparation of a Genomic DNA Library of *Penicillium brasilianum* IBT 20888

Genomic libraries were constructed using a TOPO Shotgun Subcloning Kit (Invitrogen, Carlsbad, Calif., USA). Briefly, total cellular DNA was sheared by nebulization under 10 psi nitrogen for 15 seconds and size-fractionated on 1% agarose gels using 40 mM Tris base-20 mM sodium acetate-1 mM disodium EDTA (TAE) buffer. DNA fragments migrating in the size range 3-6 kb were excised and eluted using a MiniElute™ Gel Extraction Kit (QIAGEN Inc, Valencia, Calif., USA). The eluted fragments were size-fractionated again using a 1% agarose gel as above and DNA fragments migrating in the size range 3-6 kb were excised and eluted using a MiniElute™ Gel Extraction Kit.

The eluted DNA fragments were blunt end repaired and dephosphorylated using shrimp alkaline phosphatase (Roche Applied Science, Manheim, Germany). The blunt end DNA fragments were cloned into the pCR4Blunt-TOPO vector (Invitrogen, Carlsbad, Calif., USA) according to the manufacturer's instructions, transformed into electrocompetent *E. coli* TOP10 cells by electroporation, and plated on LB ampicillin plates. The electroporation resulted in 15,300 clones.

Example 16

Purification of Native CEL5C Endoglucanase from *Penicillium brasilianum* IBT 20888

The endoglucanase was purified and assayed as described in Jørgensen et al., 2003 (*Enzyme Microb. Technol.* 32: 851-861). The substrate was azo-carboxymethyl cellulose (Megazyme International Ireland Ltd., Bray, Ireland) and the incubation time was 15 minutes. Purified enzyme was stored frozen at –20° C.

Example 17

N-Terminal Sequencing of CEL5C Endoglucanase from *Penicillium brasilianum* IBT 20888

The purified sample of *Penicillin brasilianum* CEL5C endoglucanase (Example 16) was thawed. A 100 µl aliquot of the sample was added to 100 µl of SDS-PAGE sample buffer (4 ml of 0.5 M TRIS-HCl, pH 6.8, 20 ml of 10% SDS, 20 ml of glycerol (87%), 56 ml of Milli-Q® ultrapure water, and 15 grains of bromophenol blue) in an Eppendorf tube and heated to 95° C. for 4 minutes. Following heating four 20 µl aliquots of the diluted sample were applied separately to a precast 4-20% SDS polyacrylamide gel (Invitrogen, Carlsbad, Calif., USA). In addition to the four lanes containing the sample, a Mark 12 protein standard mixture (Invitrogen, Carlsbad, Calif., USA) was applied to the gel.

The gel was run in an Xcell SureLock™ gel apparatus (Invitrogen Carlsbad, Calif., USA) for 90 minutes with initial power settings of 40 mA at maximum 135 V. Following electrophoresis the gel was incubated for 5 minutes in a blotting solution consisting of 10 mM CAPS pH 11 containing 6% methanol A ProBlott membrane (Applied Biosystems, Foster City, Calif., USA) was wetted for 1 minute in pure methanol before being placed in the blotting solution for 5 minutes in order to saturate the membrane with 10 mM CAPS pH 11 containing 6% methanol.

Electroblotting was carried out in a Semi Dry Blotter II apparatus (KemEnTec, Copenhagen, DK) as follows. Six pieces of Whatman no. 1 paper wetted in the blotting solution were placed on the positive electrode of the blotting apparatus followed by the ProBlott membrane, the polyacrylamide gel, and six pieces of Whatman no. 1 paper wetted in blotting solution. The blotting apparatus was assembled thereby putting the negative electrode in contact with the upper stack of Whatman no. 1 paper. A weight of 11.3 kg was placed on top of the blotting apparatus. The electroblotting was performed at a current of 175 mA for 180 minutes.

Following the electroblotting the ProBlott membrane was stained for 1 minute in 0.1% (w/v) Coomassie Brilliant Blue R-250 dissolved in 60% methanol, 1% acetic acid, 39% $H_2O$. Destaining of the ProBlott membrane was performed in 40% aqueous methanol for 5 minutes before the membrane was rinsed in deionized water. Finally the ProBlott membrane was air-dried.

For N-terminal amino add sequencing two pieces of the ProBlott membrane consisting of a 65 kDa band were cut out and placed in the blotting cartridge of an Applied Biosystems Precise Protein Sequencer (Applied Biosystems, Foster City, Calif., USA). The N-terminal sequencing was carried out using the method run file for PVDF membrane samples (Pulsed liquid PVDF) according to the manufacturer's instructions.

The N-terminal amino acid sequence was deduced from the resulting chromatograms by comparing the retention time of the peaks in the chromatograms to the retention times of the PTH-amino-acids in the standard chromatogram.

The N-terminal amino acid sequence of the purified *Penicillium brasilianum* CEL5C endoglucanase was determined directly using a Procise 494 HT Sequencing System (Applied Biosystems, Foster City, Calif., USA). The N-terminal sequence was determined to be Ala-Ser-Ser-Phe-Val-Trp-Phe-Gly-Thr-Ser-Glu-Ser-Gly-Ala-Glu-Phe-Gly-Asn-Gln-Asn (amino acids 25 to 44 in SEQ ID NO: 10).

Example 18

PCR Amplification of the cel5c Endoglucanase Gene from *Penicillium brasilianum* IBT 20888

Based on the N-terminal amino acid sequence of the purified *Penicillium brasilianum* endoglucanase, a forward primer was designed using the CODEHOP strategy (Rose et al., 1998, *Nucleic Acids Res.* 26: 1628-35). From database information on other endoglucanases, two reverse primers were designed as shown below using the CODEHOP strategy.

```
Forward primer, Fwd:
                                    (SEQ ID NO: 11)
5'-TTCGGTACCTCTGAGTCTGGNGCNGARTT-3'

Reverse primer, Rev1:
                                    (SEQ ID NO: 12)
5'-TGATCCATATCGTGGTACTCGTTRTTNGTRTCRAA-3'

Reverse primer, Rev2:
                                    (SEQ ID NO: 13)
5'-CCGTTGTAGCGACCGTARTTRTGNGGRTC-3'
where R = A or G, Y = C or T,
K = G or T and N = A, C, G or T
```

Amplification reactions (30 µl) were prepared using approximately 1 µg of *Penicillium brasilianum* genomic DNA as template. In addition, each reaction contained the following components: 30 pmol of the forward primer, 30 pmol of the reverse primer, 200 µM each of dATP, dCTP, dGTP, and dTTP, 1× AmpliTaq polymerase buffer (Applied Biosystems, Foster City, Calif., USA), and 0.5 unit of AmpliTaq polymerase (5.0 U/µl, Applied Biosystems, Foster City, Calif., USA). The reactions were incubated in a Robocycler (Stratagene, La Jolla, Calif., USA) programmed for 1 cycle at 96° C. for 3 minutes and at 72° C. for 3 minutes; 34 cycles each at 95° C. for 0.5 minute, 56° C. for 0.5 minutes, and 72° C. for 1.5 minutes; 1 cycle at 72° C. for 7 minutes; and a soak cycle at 6° C. Taq polymerase was added at 72° C. In the first cycle.

PCR reaction products were separated on a 2% agarose gel (Amresco, Solon, Ohio, USA) using TAE buffer. A band of approximately 650 bp (Fwd and Rev1 primers) and bands of approximately 320 and 380 bp (Fwd and Rev2 primers) were excised from the gel and purified using a MiniElute™ Gel Extraction Kit (QIAGEN Inc., Valencia, Calif., USA) according to the manufacturer's instructions. The purified PCR products were subsequently analyzed by DNA sequencing. The 320 bp product was found to encode a portion of a glycosyl hydrolase Family 5 polypeptide that was designated CEL5C.

Example 19

Screening of Genomic Library of *Penicillium brasilianum* IBT 20888

Colony lifts of the library described in Example 15 were performed (Maniatis et al., 1982, *Molecular Cloning, A Laboratory Manual*, Cold Spring Harbor Press, Cold Spring Harbor, N.Y.) and the DNA was cross-linked onto Hybond N+ membranes (Amersham, Arlington Heights, Ill., USA) for 2 hours at 80° C. The membranes from the colony lifts were pre-wetted using 0.2×SSC (30 mM NaCl, 3 mM sodium citrate), 0.2% SDS. The pre-wetted filters were placed in a beaker with 7.5 ml of 6×SSPE (0.9 M NaCl, 0.06 M $NaH_2PO_4$, and 6 mM EDTA), 7% SDS) per filter at 68° C. in a shaking water bath for 30 minutes.

Approximately 40 ng of the PCR product described in Example 18 were random-primer labeled using a Stratagene Prime-It II Kit (Stratagene, La Jolla, Calif.) according to the manufacturer's instructions. The radiolabeled gene fragment was separated from unincorporated nucleotide using a MinElute PCR Purification Kit (QIAGEN Inc., Valencia, Calif., USA).

The radioactive probe was denatured by adding 5.0 M NaOH to a final concentration of 0.5 M, and added to the hybridization solution at an activity of approximately $0.5 \times 10^6$ cpm per ml of hybridization solution. The mixture was incubated for 10 hours at 68° C. in a shaking water bath. Following incubation, the membranes were washed three times in 0.2×SSC, 0.2% SDS at 68° C. The membranes were then dried on blotting paper for 15 minutes, wrapped in SaranWrap™, and exposed to X-ray film overnight at −80° C. with intensifying screens (Kodak, Rochester, N.Y., USA).

Colonies producing hybridization signals with the probe were inoculated into 1 ml of LB ampicillin medium and cultivated overnight at 37° C. Dilutions of each solution were made and 100 µl were plated onto LB ampicillin plates. The dilution for each positive that produced about 40 colonies per plate was chosen for secondary lifts. The lifts were prepared, hybridized, and probed as above. Two colonies from each positive plate were inoculated into 3 ml of LB ampicillin medium and cultivated overnight at 37° C.

Miniprep DNA was prepared from each colony using a Bio Robot 9600 (QIAGEN Inc, Valencia, Calif., USA) according to the manufacturer's protocol. The size of each insert was determined by Eco RI restriction and agarose gel electrophoresis. Two clones each contained an approximately 5.5 kb insert. Sequencing revealed that the clones were identical, and they were hereafter referred to as pKKAH1 (see Example 20).

Example 20

Characterization of the cel5c Genomic Sequence Encoding the CEL5C Endoglucanase from *Penicillin brasilianum* IBT 20888

DNA sequencing of the *Penicillium brasilianum* endoglucanase gene from pKKAH1 was performed with an Applied Biosystems Model 3700 Automated DNA Sequencer (Applied Biosystems, Foster City, Calif., USA) using the primer walking technique with dye-terminator chemistry (Giesecke et al., 1992, *J. Viral. Methods* 38: 47-60).

The nucleotide sequence (SEQ ID NO: 9) and deduced amino add sequence (SEQ ID NO: 10) of the *Penicillium brasilianum* cel5c gene are shown in FIGS. 10A and 10B. The genomic coding sequence of 1471 bp (including stop codon) encodes a polypeptide of 421 amino acids, interrupted by 4 introns of 51 bp (89-139 bp), 47 bp (352-398 bp), 55 bp (464-518 bp), and 52 bp (617-668 bp). The % G+C content of the coding region of the gene is 51.2% and the mature polypeptide coding region is 50.8%. Using the SignalP software program (Nielsen et al., 1997, *Protein Engineering* 10: 1-6), a signal peptide of 16 residues was predicted. Based on the N-terminal sequence of the endoglucanase, residues 17 through 24 appear to constitute a pro-region that is proteolytically cleaved during maturation. The predicted mature protein contains 397 amino adds and has a predicted mass of 42.6 kDa.

Analysis of the deduced amino add sequence of the cel5c gene with the Interproscan program (Zdobnov and Apweiler, 2001, supra) showed that the CEL5C protein contained the core sequence typical of a Family 5 glycosyl hydrolase, extending from approximately residues 32 to 307 of the predicted full-length polypeptide. The CEL5C protein also contained the sequence signature of a type I fungal cellulose binding domain (CBMI). This sequence signature known as Prosite pattern PS00562 (Sigrist et al., 2002, supra) was present from amino add residue 393 to residue 420 of the predicted polypeptide.

A comparative pairwise global alignment of amino acid sequences in public databases was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the *Penicillium brasilianum* cel5c gene encoding the CEL5C mature polypeptide shared 74.9% and 74.5% identity (excluding gaps) to the deduced amino add sequences of two predicted Family 5 glycosyl hydrolase proteins from *Neosartorya fischeri* and *Aspergillus fumigatus*, respectively (accession numbers A1DAP7 and Q4WM09, respectively).

Example 21

Construction of an *Aspergillus oryzae* Expression Plasmid for the cel5c Endoglucanase Gene from *Penicillium brasilianum* IBT 20888

The *Aspergillus* expression plasmid pJaL721 (WO 03/008575) consists of an expression cassette based on the *Aspergillus niger* neutral amylase II promoter fused to the *Aspergillus nidulans* triose phosphate isomerase non-translated leader sequence (NA2-tpi) and the *Aspergillus niger* amyloglycosidase terminator. Also present on the plasmid is the selective marker amdS from *Aspergillus nidulans* enabling growth on acetamide as sole nitrogen source and the URA3 marker from *Saccharomyces cerevisiae* enabling growth of the pyrF defective *Escherichia coli* strain DB6507 (ATCC 35673). Transformation into *E. coli* DB6507 was performed using the *Saccharomyces cerevisiae* URA3 gene as selective marker as described below.

*E. coli* DB6507 was made competent by the method of Mandel and Higa, 1970, *J. Mol. Biol.* 45: 154. Transformants were selected on solid M9 medium (J. Sambrook, E. F. Fritsch, and T. Maniatis, 1989, *Molecular Cloning, A Laboratory Manual*, 2d edition, Cold Spring Harbor, N.Y.) supplemented per liter with 1 g of casamino acids, 500 µg of thiamine, and 10 mg of kanamycin.

The endoglucanase gene was cloned into pJaL721 as described below. The cel5c endoglucanase gene from *Penicillium brasilianum* was amplified by PCR using the following two oligonucleotide primers:

```
Forward PCR:
                                  (SEQ ID NO: 14)
5'-AATTGGATCCACCATGAAATACCCTCTACTCCTGGCAAC-3'

Reverse PCR:
                                  (SEQ ID NO: 15)
5'-TTAACTCGAGTTACAGACACTGCGAATAATACGCATTC-3'
```

To facilitate cloning a restriction enzyme site was inserted into the 5' end of each primer where the forward primer contained a Bam HI site and the reverse primer contained an Xho I site.

Genomic DNA prepared as in Example 14 was used as template in the PCR reaction. The reaction was performed in a volume of 50 µl containing 1.0 unit of Phusion (Finnzymes Oy, Espoo, Finland), 1× Phusion buffer HF (Finnzymes Oy, Espoo, Finland), 500 ng of genomic, 250 μM of each dNTP, and 50 pmol of each of the two primers described above. The amplification was carried out in a PTC-220 DNA Engine Dyad Peltier Thermal Cycler (MJ Research, Inc., Waltham, Mass., USA) programmed for 1 cycle at 95° C. for 5 minutes; 24 cycles each at 94° C. for 0.5 minute, 58° C. for 0.5 minute, and 68° C. for 4.0 minutes; and 1 cycle at 68° C. for 15 minutes. The hot start PCR technique (Chou et al., 1992, *Nucleic Acids Res.* 20: 1717) was used and the Phusion polymerase was added after 1 minute of the first cycle.

Figure 11:
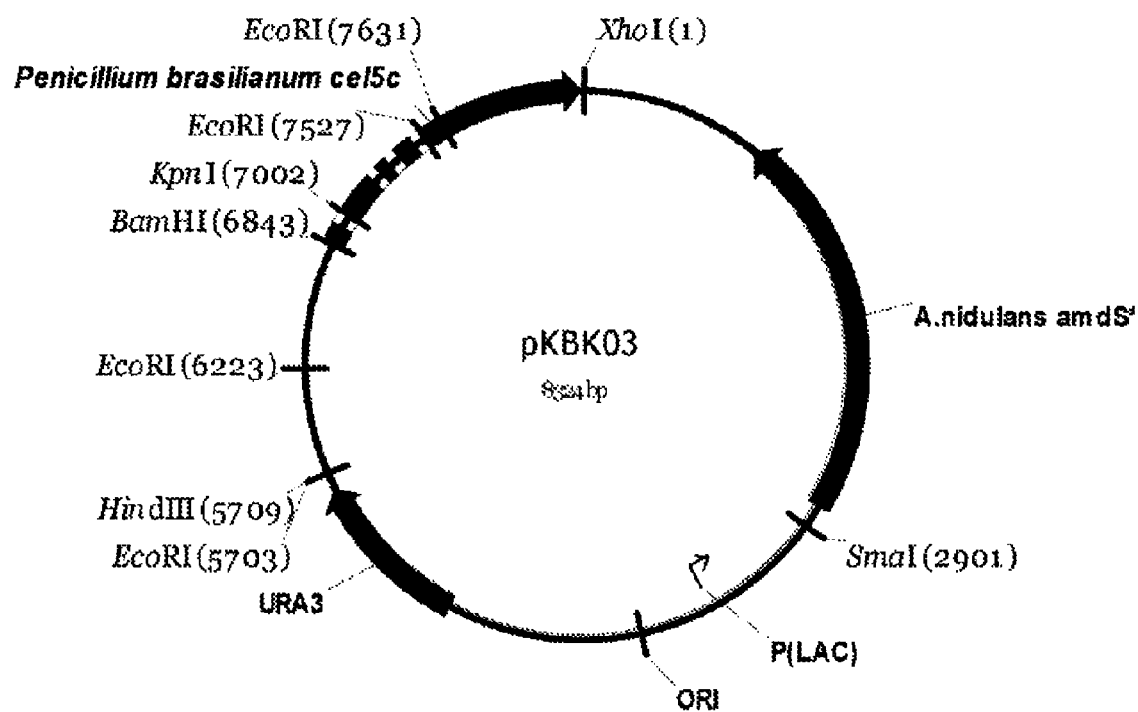
FIG. 11 shows a restriction map of pKBK03.

The PCR reaction produced a single DNA fragment of approximately 1500 bp in length. The fragment was digested with Bam HI and Xho I and isolated by agarose gel electrophoresis, purified, and cloned into pJaL721 digested with Bam HI and Xho I, resulting in a plasmid designated pKBK03 (FIG. 11). The sequence of the endoglucanase gene in pKBK03 was verified by sequencing with an Applied Biosystems 3730xl DNA Analyzer.

In order to create a plasmid for deposit of biological material, pKBK03 was digested with Bam HI and Xho I and purified. The fragment was blunt end repaired using Klenow enzyme (Roche Applied Science, Manheim, Germany) for 30 minutes at 25° C. Plasmid pUC13 was digested with Sma I and dephosphorylated with Calf Intestinal Protease (Roche Applied Science, Manheim, Germany; CIP) for 1 hour at 37° C. and the CIP was inactivated by heating the sample to 80° C. for 15 minutes.

Figure 12:
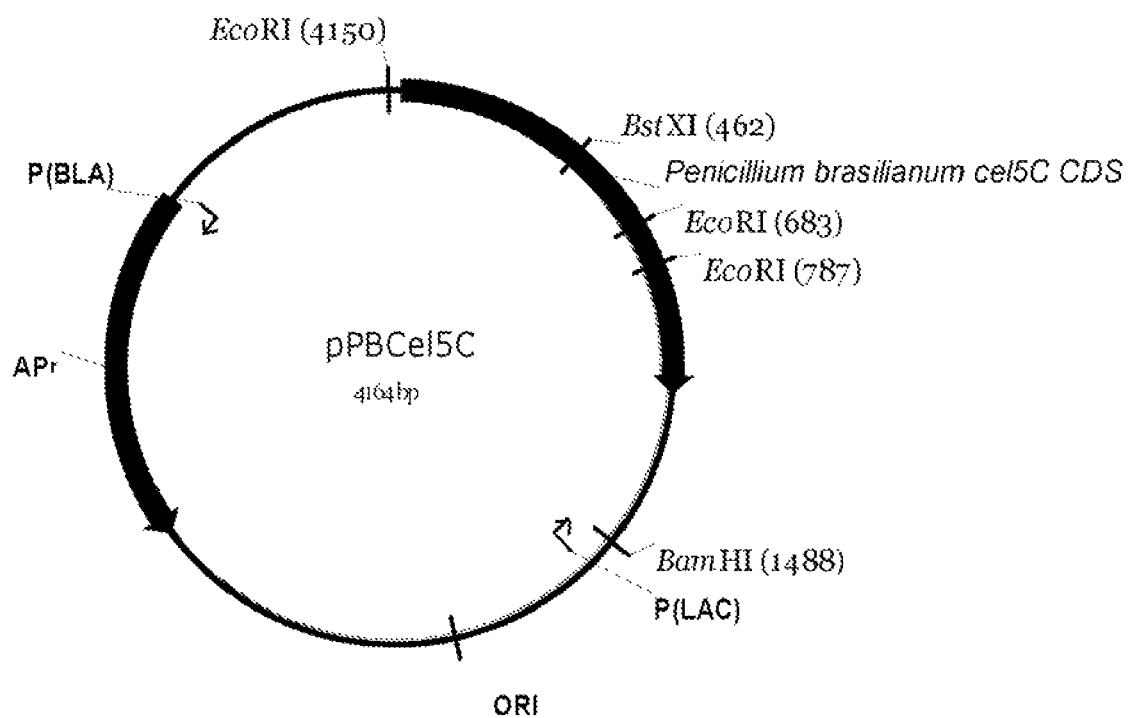
FIG. 12 shows a restriction map of pPBCel5C.

The blunt end repaired fragment and the dephosphorylated pUC13 fragment were ligated overnight at 16° C. using T4 DNA ligase (Roche Applied Science, Manheim, Germany). A 0.25 μg sample of the ligated product was transformed into *Escherichia coli* DH5α (Invitrogen, Carlsbad, Calif., USA). After incubation overnight at 37° C. on LB ampicillin plates, transformants were transferred to 2 ml of LB medium and incubated at 37° C. A plasmid designated pPBCel5C (FIG. 12) was purified using Jetquick Plasmid Miniprep (Genomed, Löhne, Germany). The sequence of the endoglucanase gene was verified by sequencing with an Applied Biosystems 3730xl DNA Analyzer. *E. coli* TOP10 cells (Invitrogen, Carlsbad, Calif.) containing plasmid pPBCel5C (strain designation PBCel5C) were deposited with the Agricultural Research Service Patent Culture Collection, Northern Regional Research Center, 1815 University Street, Peoria, Ill., 61604, as NRRL B-30900N, with a deposit date of Feb. 23, 2006.

Example 22

Expression of the *Penicillium brasilianum* IBT 20888 CEL5C Endoglucanase in *Aspergillus oryzae*

*Aspergillus oryzae* BECh2 (WO 00/30322) was transformed with 5 μg of pKBK03 as described by Christensen et al., 1988, *Biotechnology* 6: 1419-1422.

Transformants were cultivated in 50 ml tubes for 4 days at 30° C. in 10 ml of YPM medium. The whole broths were centrifuged at 12,100×g and the supernatants removed. The supernatants were analyzed by SDS-PAGE using a Criterion XT Precast Gel, 10% Bis-Tris gel in a XT MES buffer (Bio-Rad Laboratories, Hercules, Calif., USA) according to the manufacturers instructions. A 10 μl volume of supernatant was mixed with 9 μl of sample buffer (0.125 M Tris-HCl pH 6.8, 20% glycerol, and 4.6% SDS), and 1 μl of 1 M dithiothreitol, and heated to 96° C. for 5 minutes. In 16 out of 20 supernatants, one band of approximately 65 kDa was visible in the range of the standards 35 kDa to 150 kDa by SDS-PAGE. The supernatants resulting in a visible band after SDS-PAGE also contained endoglucanase activity, assayed as described in Example 3. The higher the intensity of the band, the higher endoglucanase activity measured in the same supernatant.

One transformant was designated *Aspergillus oryzae* KBK03.

Example 23

Production and Purification of Recombinant *Penicillium brasilianum* IBT 20888 CEL5C Endoglucanase

*Aspergillus oryzae* transformant KBK03 was grown in twenty 500 ml shake flasks with 200 ml of YPM medium.

The biomass was removed from 4.0 liters of fermentation broth by centrifugation and filtration. SDS-PAGE analysis was performed as described in Example 9. The endoglucanase solution was loaded onto a XK 50 column (Amersham Biosciences, Uppsala, Sweden) containing 110 g of Avicel Ph 101 (Merck KGaA, Darmstadt, Germany) pre-equilibrated with 25 mM Tris pH 7.5 prior to loading and the bound enzyme was eluted with 25 mM Tris, 1% triethanolamine at pH 11.6. Elution of the endoglucanase was monitored at 280 nm. The eluted protein containing fractions were pooled immediately and the pH adjusted to 7.5. Fractions containing the endoglucanase were pooled.

The protein content was determined from the absorbance at 280 nm and the extinction coefficient calculated from the primary structure of the endoglucanase.

The purification was followed by SDS-PAGE. The samples were boiled for 2 minutes with an equal volume of 2× sample buffer and ⅕ volume of 1% PMSF and loaded onto a 4-20% Tris-glycine gel (Invitrogen, Carlsbad, Calif., USA). The gel was stained with GelCode Blue Stain Reagent (Pierce, Rockford, Ill., USA) and destained with water. SOS-PAGE revealed one band of approximately 65 kDa.

Example 24

Characterization of Purified Recombinant *Penicillium brasilianum* IBT 20888 CEL5C Endoglucanase The purified recombinant *Penicillium brasilianum* CEL5C endoglucanase described in Example 23 was characterized with regard to pH optimum, temperature optimum, and temperature stability. The endoglucanase activity was measured as described in Example 16 at temperatures from 20° C. to 80° C. and at pH values of 3.0 to 10.0. The purified endoglucanase was diluted in ultrapure water (Millipore, Billerica, Mass., USA) to ensure that activity was within the standard curve. For the pH optimum, the substrate was dissolved in Britton-Robinson buffer (50 mM boric acid, 50 mM acetic acid, 50 mM phosphoric acid) adjusted to the desired pH. The temperature stability was determined for 20 hours at 50° C. in the pH range from 4.0 to 6.0. All experimental assays were performed in duplicate.

Figure 13:
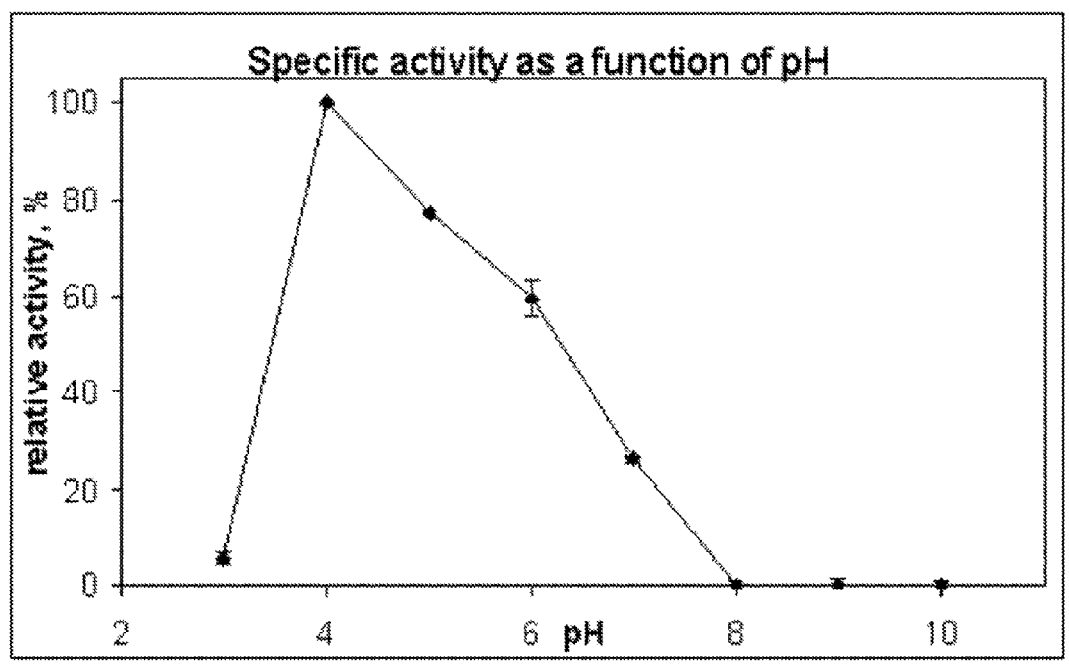
FIG. 13 shows the specific activity of the *Penicillium brasilianum* IBT 20888 CEL5C endoglucanase at different pH values and 50° C. (n=2).

The results of the pH optimum determination is shown in FIG. 13. The optimum pH was close to 4.0 at 50° C. with very little activity at pH 3.0 and approximately 80% of peak activity at pH 5.0.

Figure 14:
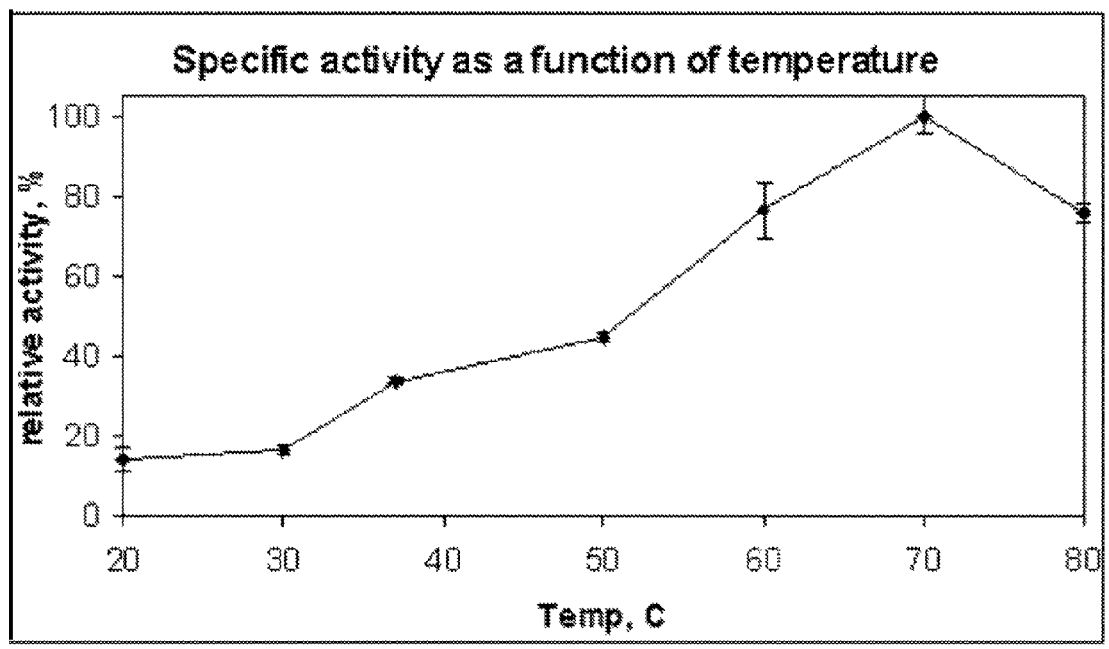
FIG. 14 shows the specific activity of the *Penicillium brasilianum* IBT 20888 CEL5C endoglucanase at different temperatures and pH 4.8 (n=2).

The results of the temperature optimum determination is shown in FIG. 14. The temperature optimum at pH 4.8 was approximately 70° C. with more than 75% of peak activity from 60° C. to 80° C.

Figure 15:
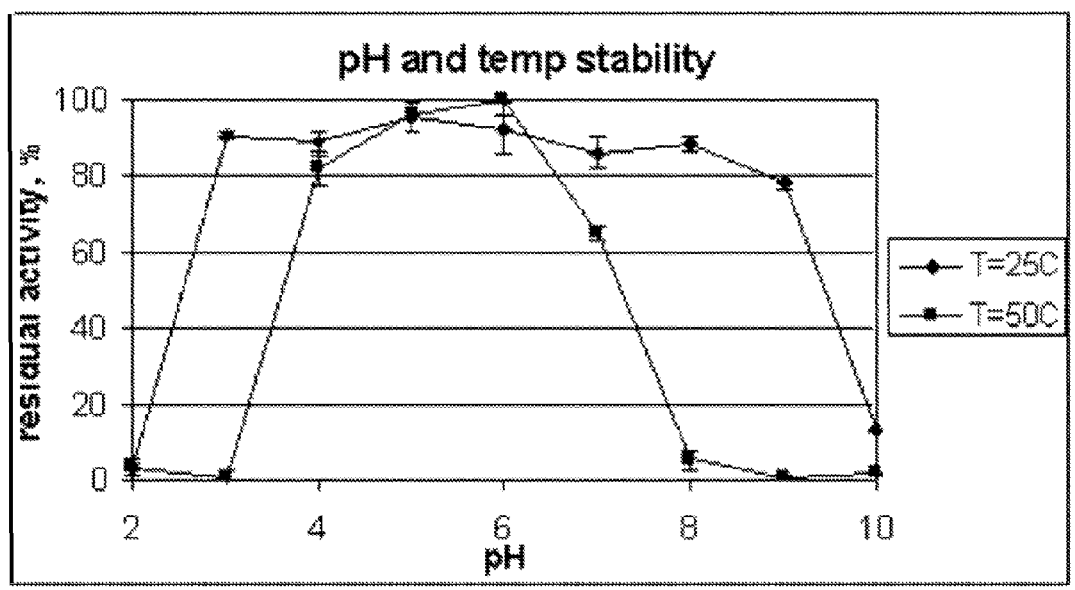
FIG. 15 shows the residual activity of the *Penicillium brasilianum* IBT 20888 CEL5C endoglucanase after 20 hours of incubation at different pH values and 25° C. and 50° C. (n=2).

The results of the temperature stability determination is shown in FIG. 15. When pre-incubated in the absence of substrate for 20 hours at 25° C. and 50° C. in the pH range from 4.0 to 6.0, the endoglucanase retained more than 80% of its starting activity.

Example 25

Preparation of Substrates

Pretreated corn stover (PCS) was prepared by the U.S. Department of Energy National Renewable Energy Laboratory (NREL) using dilute sulfuric acid. The following conditions were used for the pretreatment: 1.4 wt % sulfuric acid at 165° C. and 107 psi for 8 minutes. Compositional analysis was performed at NREL. Cellulose and hemicellulose were determined by a two-stage sulfuric acid hydrolysis with subsequent analysis of sugars by high performance liquid chromatography (HPLC) using NREL Standard Analytical Procedure #002. Lignin was determined gravimetrically after hydrolyzing the cellulose and hemicellulose fractions with sulfuric acid (NREL Standard Analytical Procedure #003). Water-insoluble solids in the pretreated corn stover (PCS) were determined to be 56.5% cellulose, 4.6% hemicellulose, and 28.4% lignin.

The PCS was washed with large volume of deionized water on a Kimax funnel with a glass filter of coarse porosity (Fisher Scientific, Pittsburg, Pa., USA). Water-washed PCS was milled in a coffee grinder and additionally washed with deionized water on a 22 μm Millipore Filter with a 6P Express Membrane (Millipore, Bedford, Mass., USA). Dry weight of the milled PCS was 32.4%.

A 10 mg/ml stock suspension of phosphoric acid-swollen cellulose (PASC) in deionized water was prepared using the following procedure. One hundred and fifty ml of ice-cold 85% o-phosphoric acid was added to 5 g of Avicel PH101 (FMC Corp., Philadelphia, Pa., USA) moistened with water. The suspension was slowly stirred in an ice bath for one hour, and 100 ml of ice-cold acetone was added to the suspension at constant stirring. The slurry was transferred to a Kimax funnel with a glass filter of coarse porosity, washed three times with 100 ml of ice-cold acetone, and drained as completely as possible after each wash. Finally, the slurry was washed twice with 500 ml of water, and again drained as completely as possible after each wash. The PASC was mixed with water to a total volume of 500 ml. Sodium azide was added to a final concentration of 0.02% to prevent microbial growth. The slurry was homogenized using a blender and stored at 4° C. for up to one month.

Carboxymethylcellulose (CMC, sodium salt, type 7L2) with an average degree of substitution (DS) of 0.7 was obtained from Aqualon Division of Hercules Inc., Wilmington, Del., USA. A 6.25 mg/ml solution of CMC in 50 mM sodium acetate pH 5.0 was prepared by slowly adding CMC to the vigorously agitated buffer. The slurry was heated to approximately 60° C. under continuous stirring until the CMC was completely dissolved.

Bacterial cellulose (BC) was prepared from Nate de Coco, a food-grade commercial cellulose (Fujicco Co., Kobe, Japan), as described in Boisset et al., 1999, *Biochemical Journal*, 340: 829-835. A 1 mg/ml suspension of bacterial cellulose in deionized water with 0.01% (w/v) sodium azide was stored at 4° C.

Avicel PH101 was obtained from FMC Corporation, Philadelphia, Pa., USA.

Xylan from birchwood was obtained from Sigma, St. Louis, Mo., USA. Xyloglucan from Tamarind seed (amyloid, lot 00401), wheat arabinoxylan (medium viscosity, 27 cSt, lot 90601), 1,4-beta-D-mannan (borohydride reduced, Man:Gal=97:3, degree of polymerization DP ~15, lot 90302), and carob galactomannan (low viscosity, borohydride reduced, lot 90301) were obtained from Megazyme, Bray, Ireland.

Example 26 p-Hydroxybenzoic Acid Hydrazide Assay for Determination of Reducing Sugars

Reducing sugars (RS) were determined by a p-hydroxybenzoic acid hydrazide (PHBAH) assay (Lever, 1972, *Anal. Biochem.* 47: 273-279), which was adapted to a 96-well microplate format.

A 90-μl aliquot of the diluted sample was placed into each well of a 96-well conical-bottomed microplate (Costar, clear polycarbonate, Corning Inc., Acton, Mass., USA). The assay was initiated by adding 60 μl of 1.25% PHBAH in 2% sodium hydroxide to each well. The uncovered plate was heated on a custom-made heating block for 10 minutes at 95° C. Following heating, the microplate was cooled to room temperature, and 35 μl of deionized water was added to each well. A 100 μl aliquot was removed from each well and transferred to a flat-bottomed 96-well plate (Costar, medium binding polystyrene, Corning Inc., Acton, Mass., USA). The absorbance at 410 nm ($A_{410}$) was measured using a SpectraMAX Microplate Reader (Molecular Devices, Sunnyvale, Calif., USA). The $A_{410}$ value was translated into glucose equivalents using a standard curve.

The standard curve was obtained with six glucose standards (0.005, 0.010, 0.025, 0.050, 0.075, and 0.100 mg/ml), which were treated similarly to the samples. Glucose standards were prepared by diluting 10 mg/ml stock glucose solution with deionized water.

For all substrates except for xylan and arabinoxylan, the degree of conversion (%) was calculated using the following equation:

$$\text{Conversion}_{(\%)} = \text{RS}_{(mg/ml)} \times 100 \times 162 / (\text{Initial substrate concentration}_{(mg/ml)} \times 180) = \text{RS}_{(mg/ml)} \times 100 / (\text{Initial substrate concentration}_{(mg/ml)} \times 1.111)$$

For xylan and arabinoxylan, percent of substrate hydrolyzed to RS was calculated using the following equation:

$$\text{Conversion}_{(\%)} = \text{RS}_{(mg/ml)} \times 100 \times 132 / (\text{Initial substrate concentration}_{(mg/ml)} \times 150) = \text{RS}_{(mg/ml)} \times 100 / (\text{Initial substrate concentration}_{(mg/ml)} \times 1.136)$$

In these equations, RS is the concentration of reducing sugars in solution measured in glucose equivalents (mg/ml), and the factors 1.111 and 1.136 reflect the weight gain in converting corresponding polysaccharides to hexose (MW 180) or pentose (MW 150) sugars.

Example 27

Relative Activity of Endoglucanases on Carboxymethyl-Cellulose at 50° C.

Table 1 shows the relative activity of the purified endoglucanases from *Myceliophthora thermophila* CBS 117.65, basidiomycete CBS 494.95, and basidiomycete CBS 495.95 toward the soluble sodium salt of carboxymethylcellulose (CMC). The relative activity is shown as percentage of the activity of basidiomycete CBS 495.95 endoglucanase. The activity was determined by measuring the concentration of reducing sugars (RS) produced from CMC (5 mg/ml) after 30 minutes of hydrolysis in 50 mM sodium acetate pH 5.0 at 50°

C. Hydrolysis was carried out without stirring in the presence of 0.5 mg/ml bovine serum albumin (BSA, Sigma. St. Louis, Mo., USA). Reducing sugars were determined using p-hydroxybenzoic acid hydrazide (PHBAH) assay described in Example 26.

TABLE 1

Relative activity of endoglucanases on carboxymethylcellulose (5 mg/ml) at pH 5.0 and 50° C.

| Endoglucanase | Activity on CMC, % |
|---|---|
| Myceliophthora thermophila Cel5A | 28 |
| basidiomycete CBS 494.95 Cel5B | 44 |
| basidiomycete CBS 495.95 Cel5A | 100 |

Example 28

Thermal Stability of Endoglucanases at 40° C.-80° C.

The thermal stability of the purified endoglucanases from Myceliophthora thermophila CBS 117.65, basidiomycete CBS 494.95, and basidiomycete CBS 495.95 was determined by incubating enzyme solutions at five temperatures (40° C., 50° C., 60° C., 70° C., and 80° C.), and measuring the residual activity of enzymes on carboxymethylcellulose (CMC).

The enzymes were diluted in 50 mM sodium acetate pH 5.0, which contained 3.0 mg/ml BSA, and incubated for 3 hours in 1.1-ml ImmunoWare Microtubes arranged in an 8×12 microplate format (Pierce, Rockford, Ill., USA). BSA was added in order to prevent possible enzyme adsorption onto the plastic walls of microtubes. The protein concentration in the incubation mixtures was chosen so that each enzyme would give less than 1% conversion of CMC in subsequent assay for CMCase activity.

After a 3 hour incubation, 15 µl aliquots were removed using an 8-channel pipettor, and added to 75 µl of CMC solution (6 mg/ml in 50 mM sodium acetate pH 5.0) in a 96-well conical-bottomed microplate (Costar, clear polycarbonate, Corning Inc., Acton, Mass., USA). The residual CMCase activity was then measured as described in Example 27, and expressed as a percentage of the initial CMCase activity (Table 2).

At 40° C. and 50° C., all three endoglucanases were stable and retained 98-100% of the initial CMCase activity after 3 hours of incubation. At 60° C. and 70° C., the Myceliophthora thermophila Cel5A showed better stability than the two other endoglucanases, and retained 100% and 49.3% of the initial CMCase activity after a 3-hour incubation, respectively. None of the endoglucanases were stable at 80° C.

TABLE 2

Residual CMCase activity of endoglucanases after incubation for three hours at pH 5.0 and 40-80° C.

| Endoglucanase | Residual CMC-ase activity, % of initial activity | | | | |
|---|---|---|---|---|---|
| | 40° C. | 50° C. | 60° C. | 70° C. | 80° C. |
| Myceliophthora thermophila Cel5A | 100 | 100 | 100 | 49.3 | 3.8 |
| basidiomycete CBS 494.95 Cel5B | 100 | 98 | 28.0 | 5.0 | 4.1 |
| basidiomycete CBS 495.95 Cel5A | 100 | 99 | 6.4 | 2.4 | 0.8 |

Example 29

Relative Activity of Endoglucanases on Phosphoric Acid-Swollen Cellulose at 40-70° C.

The activity of the purified endoglucanases from basidiomycete CBS 494.95 and basidiomycete CBS 495.95 on phosphoric acid-swollen cellulose (PASC) was determined by measuring the concentration of the reducing sugars (RS) released during initial hydrolysis of PASC (2 mg/ml) in 50 mM sodium acetate pH 5.0. Hydrolysis was carried out without stirring in the presence of 0.5 mg/ml bovine serum albumin (BSA, Sigma, St Louis, Mo., USA). The enzymes were diluted so that the RS concentration would increase linearly during the initial 30 to 90 minutes of hydrolysis, and the degree of PASC conversion would not exceed 2% during this time. Reducing sugars were determined using the p-hydroxybenzoic acid hydrazide (PHBAH) assay as described in Example 26.

Figure 16:
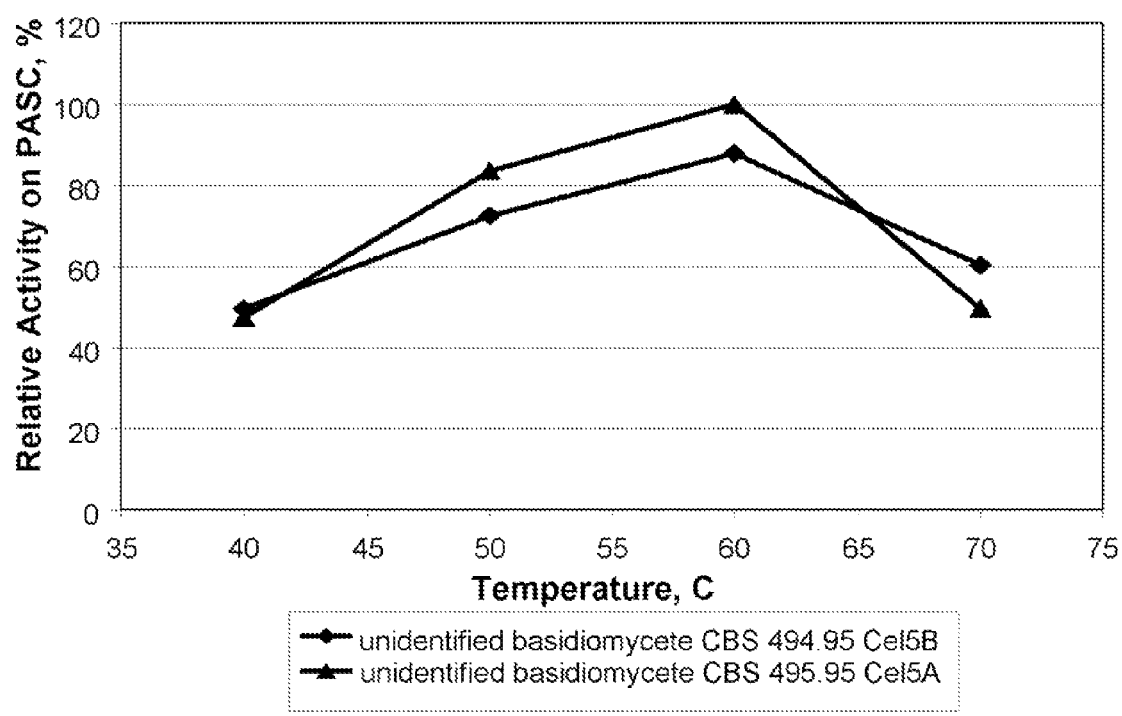
FIG. 16 shows the relative activity on PASC (2 mg/ml) as a function of temperature for basidiomycete CBS 494.95 and basidiomycete CBS 495.95 at pH 5.0.

The relative activity as a function of temperature of the endoglucanases from basidiomycete CBS 494.95 and basidiomycete CBS 495.95 is shown in FIG. 16. The activity is shown as percentage of the activity of the endoglucanase from basidiomycete CBS 495.95 at 60° C. For both endoglucanases, the activity on PASC attained the maximum value at $T_{opt}=60°$ C.

Example 30

Long-Term Hydrolysis of Phosphoric Acid-Swollen Cellulose at 40-70° C.

Hydrolysis of phosphoric acid-swollen cellulose (PASC, 2 mg/ml) by the purified endoglucanases from basidiomycete CBS 494.95 and basidiomycete CBS 495.95 was carried out for 45 hours in 50 mM sodium acetate pH 5.0 containing 0.5 mg/ml BSA at four temperatures, 40° C., 50° C., 60° C., and 70° C. The endoglucanases were used at three protein loadings, 0.056, 0.167, or 0.5 mg per g of PASC. The reactions with the initial volume of 1 ml were run without stirring in 1.1-ml ImmunoWare Microtubes arranged in an 8×12 microplate format (Pierce, Rockford. Ill. USA).

One hundred microliter aliquots were removed from the reactions at different time points (1, 1.5, 3, 6, 21, 27, and 45 hours) using an 8-channel pipettor, and added to 25 µl of 2% NaOH in MultiScreen HV 96-well filtration plate (Millipore, Bedford, Mass., USA). The collected samples were vacuum-filtered into a flat-bottomed microplate to remove the PASC residue. The filtrates were analyzed for reducing sugars by the p-hydroxybenzoic acid hydrazide (PHBAH) assay as described in Example 26.

Figure 17:
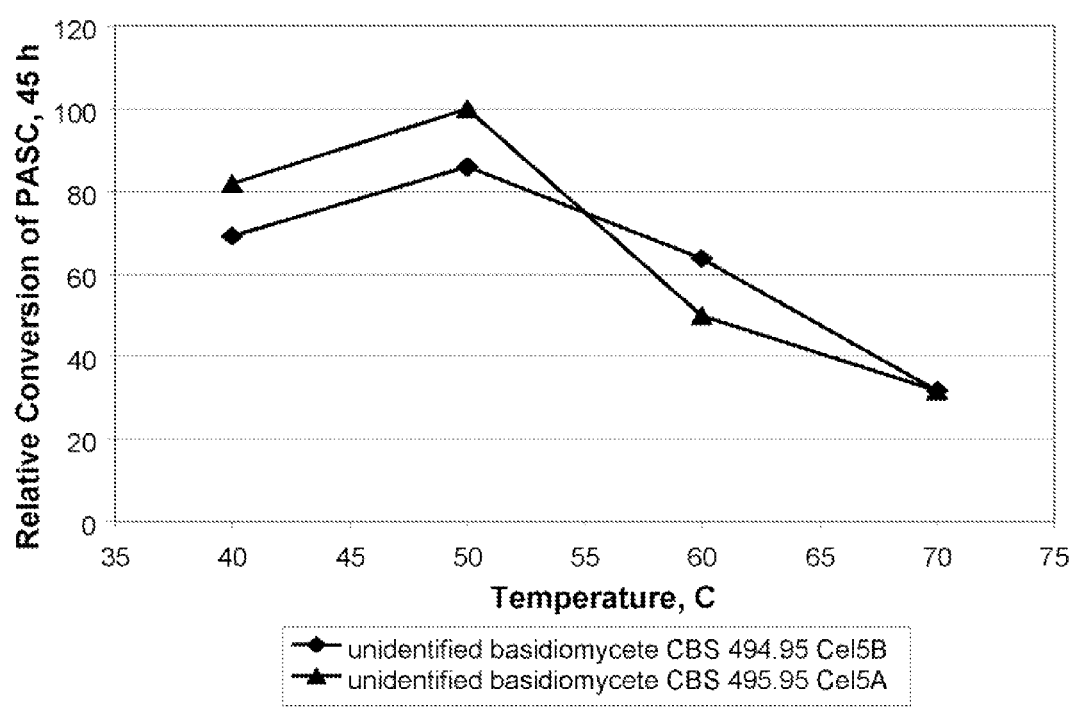
FIG. 17 shows the relative conversion of PASC (2 mg/ml) as a function of temperature after 45 hours of hydrolysis with basidiomycete CBS 494.95 and basidiomycete CBS 495.95 (0.5 mg protein per g of PASC) at pH 5.0.

FIG. 17 shows the relative conversion of PASC after a 45 hour incubation with the endoglucanases from basidiomycete CBS 494.95 and basidiomycete CBS 495.95 (0.5 mg protein per g of PASC) as a function of temperature. The relative conversion is shown as a percentage of the conversion obtained after 45-hour incubation with basidiomycete CBS 495.95 at 50° C. Temperature profiles obtained at two other protein loadings, 0.056 and 0.167 mg protein per g of PASC, had similar shapes. For both endoglucanases, the optimal temperature for long-term hydrolysis of PASO was 50° C.

Example 31

Characterization of Endoglucanases on Various Polysaccharide Substrates at 50° C.

The purified endoglucanases from Myceliophthora thermophila CBS 117.65, basidiomycete CBS 494.95, and basidiomycete CBS 495.95 were evaluated in the hydrolysis of various polysaccharides at pH 5.0 (50 mM sodium acetate buffer) and 50° C. The results were compared with those for recombinant *Trichoderma reesei* Cel7B (EGI) endoglucanase. The GH5 endoglucanases had low activity on insoluble substrates with high degree of crystallinity: bacterial cellulose, Avicel, and PCS.

TABLE 3

Relative conversion of various polysaccharide substrates (5 mg/ml) by endoglucanases (5 mg protein per g solids); pH 5.0, 50° C., 24 hours

| Substrate | *Myceliophthora thermophila* Cel5A | basidiomycete CBS 494.95 Cel5B | basidiomycete CBS 495.95 Cel5A | *Trichoderma reesei* Cel7B |
|---|---|---|---|---|
| Pretreated corn stover (PCS) | 2 | 6 | 6 | 10 |
| Phosphoric acid-swollen cellulose (PASC)** | 10 | 40 | 70 | 38 |
| Carboxymethylcellulose (CMC)** | 12 | 12 | 12 | 14 |
| Bacterial cellulose (BC)* | 1 | 5 | 5 | 5 |
| Avicel (microcrystalline cellulose) | 1 | 2 | 3 | 5 |
| Birchwood xylan | 0 | 3 | 2 | 51 |
| Tamarind xyloglucan | 0 | 1 | 1 | 87 |
| Wheat arabinoxylan | 6 | 7 | 8 | 81 |
| 1,4-β-D-Mannan | 70 | 73 | 100 | 2 |
| Carob galactomannan | 52 | 54 | 62 | 3 |

*Initial concentration of bacterial cellulose was 0.9 mg/ml
**All endoglucanases were used at 0.25 mg protein per g solids for hydrolysis of PASC and CMC recombinant *Trichoderma reesei* Cel7B (EGI) endoglucanase. Recombinant *Trichoderma reesei* Cel7B (EGI) endoglucanase produced by *Aspergillus oryzae* can be prepared according to Takashima et al. 1998, *Journal of Bacteriology* 65: 163-171.

The polysaccharides included pretreated corn stover (PCS), phosphoric acid-swollen cellulose (PASC), carboxymethylcellulose (CMC), bacterial cellulose (BC), Avicel, xylan, xyloglucan, arabinoxylan, mannan and galactomannan. All substrates were used at 5 mg/ml, with the exception of bacterial cellulose, which was used at 0.9 mg/ml.

Reactions with an initial volume of 1 ml were carried out for 24 hours with intermittent stirring in Eppendorf 96 Deep-Well Plates (1.2 ml, VWR Scientific, West Chester, Pa., USA) capped with Eppendorf 96 DeepWell Mats (VWR Scientific, West Chester, Pa., USA). Unless otherwise specified, the enzymes were loaded at 5 mg of protein per g of solids.

After 24 hours, 20 µl aliquots were removed from the hydrolysis reactions using an 8-channel pipettor, and added to 180 µl of 102 mM $Na_2CO_3$-58 mM $NaHCO_3$) in a Multi-Screen HV 96-well filtration plate (Millipore, Bedford, Mass., USA) to terminate the hydrolysis. The samples were vacuum-filtered into a flat-bottomed microplate. After appropriate dilution, the filtrates were analyzed for reducing sugars using the p-hydroxybenzoic acid hydrazide (PHBAH) assay as described in Example 26.

Table 3 shows relative conversion of various polysaccharides by the endoglucanases after 24-hour incubation. The relative conversion was calculated as a percentage of conversion obtained after 24-hour hydrolysis of 1,4-β-D-mannan by basidiomycete CBS 495.95 Cel5A endoglucanase. Endoglucanases from glycoside hydrolase (GH) family 5 had relatively high activity on mannan and galactomannan, but low activity on xylan, xyloglucan and arabinoxylan. In contrast, *Trichoderma reesei* Cel7B had relatively high activity on xylan, xyloglucan and arabinoxylan, but low activity on mannan and galactomannan. The GH5 endoglucanases showed better hydrolysis of PASC (insoluble unsubstituted amorphous cellulose) than CMC (soluble substituted cellulose derivative). The GH5 endoglucanases had low activity on insoluble substrates with high degree of crystallinity: bacterial cellulose, Avicel, and PCS.

Example 32

Hydrolysis of Soluble Beta-Glucan from Barley by Endoglucanases at 60° C.

The activity of the endoglucanases from *Myceliophthora thermophila* CBS 117.65, basidiomycete CBS 494.95, and basidiomycete CBS 495.95 on soluble beta-glucan from barley (medium viscosity, 230 kDa, Megazyme International Ireland Ltd., Bray, Ireland) was determined at pH 5.5 (50 mM sodium acetate with 0.02% sodium azide) and 60° C. The results were compared with those for *Trichoderma reesei* Cel7B (EGI) endoglucanase. Recombinant *Trichoderma reesei* Cel7B (EGI) endoglucanase can be prepared as described in Example 31.

The initial concentration of beta-glucan in the hydrolysis reactions was 1.0% (w/v). One ml reactions were run without stirring in Eppendorf 96 DeepWell Plates (1.2 ml, VWR Scientific, West Chester, Pa., USA). The enzymes were used at three protein loadings, 0.05, 0.1, and 0.2 mg per g of glucan. In a buffer control, the endoglucanases were substituted with 50 mM sodium acetate pH 5.5 containing 0.02% sodium azide.

Figure 18:
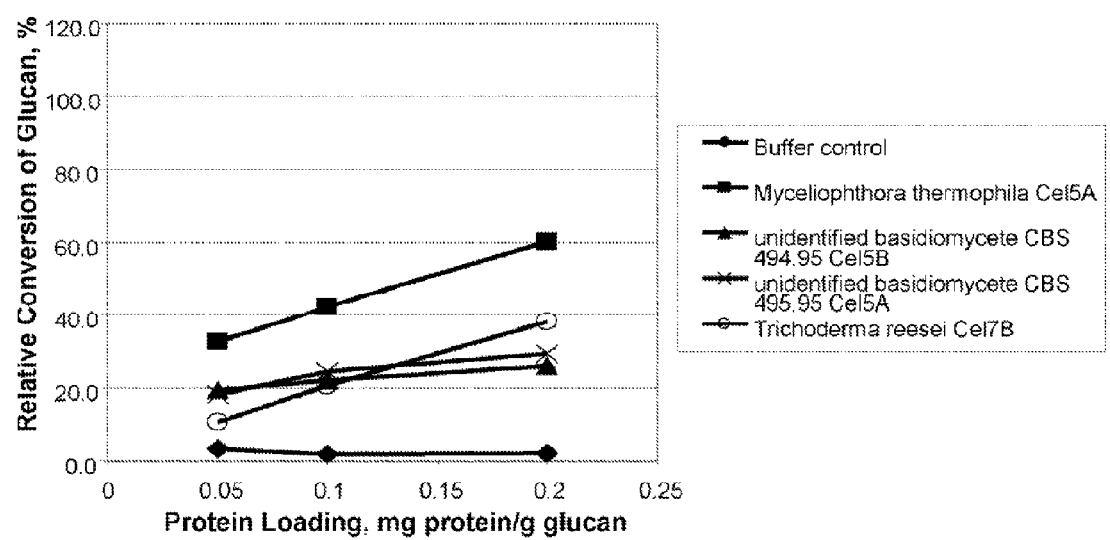
FIG. 18 shows a comparison of endoglucanases from *Myceliophthora thermophila* CBS 117.65, basidiomycete CBS 494.95, basidiomycete CBS 495.95, and *Trichoderma reesei* for production of reducing sugars from beta-glucan (1% w/v) after 2-hour hydrolysis reaction at pH 5.5 and 60° C.
Figure 19:
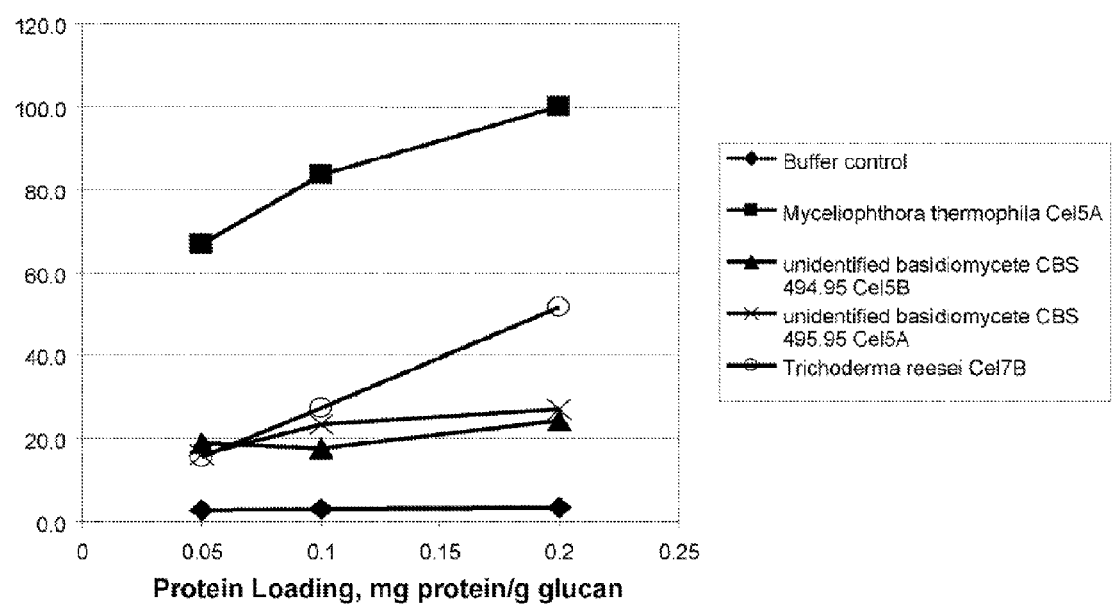
FIG. 19 shows a comparison of endoglucanases from *Myceliophthora thermophila* CBS 117.65, basidiomycete CBS 494.95, basidiomycete CBS 495.95, and *Trichoderma reesei* for production of reducing sugars from beta-glucan (1% w/v) after 2-hour hydrolysis reaction at pH 5.5 and 60° C.

Aliquots were removed from the hydrolysis reactions at 2 hours and 24 hours, diluted with deionized water, and analyzed for reducing sugars using the p-hydroxybenzoic acid hydrazide (PHBAH) assay as described in Example 26. The relative conversion of beta-glucan as a function of protein loading at two incubation times, 2 hours and 24 hours, is shown in FIGS. 18 and 19, respectively. The relative conversion is shown as a percentage of conversion obtained after 24 hour hydrolysis of beta-glucan by *Myceliophthora thermophila* CBS 117.65 Cel5A endoglucanase (0.2 mg protein per g of glucan).

The endoglucanases from basidiomycete CBS 494.95 and basidiomycete CBS 495.95 showed similar performance in hydrolyzing beta-glucan, and produced no additional increase in reducing sugar concentration after 2 hour hydrolysis. In contrast, the endoglucanases from *Myceliophthora*

*thermophila* and *Trichoderma reesei* continued to produce new reducing end-groups beyond the 2 hour incubation time. The *Myceliophthora thermophila* endoglucanase showed better performance in hydrolyzing beta-glucan than the basidiomycete CBS 494.95 Cel5B endoglucanase and basidiomycete CBS 495.95 Cel5A endoglucanase.

Deposit of Biological Material

The following biological materials have been deposited under the terms of the Budapest Treaty with the Agricultural Research Service Patent Culture Collection, Northern Regional Research Center, 1815 University Street, Peoria, Ill., 61604, and given the following accession numbers:

| Deposit | Accession Number | Date of Deposit |
| --- | --- | --- |
| *E. coli* strain PBCel5C | NRRL B-30900N | Feb. 23, 2006 |
| *E. coli* strain pCIC161 | NRRL B-30902 | Feb. 23, 2006 |
| *E. coli* strain pCIC453 | NRRL B-30903 | Feb. 23, 2006 |
| *E. coli* strain pCIC486 | NRRL B-30904 | Feb. 23, 2006 |

The strains have been deposited under conditions that assure that access to the cultures will be available during the pendency of this patent application to one determined by the Commissioner of Patents and Trademarks to be entitled thereto under 37 C.F.R. §1.14 and 35 U.S.C. §122. The deposits represent substantially pure cultures of the deposited strains. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated polypeptide having endoglucanase activity, selected from the group consisting of:
   (a) a polypeptide comprising an amino acid sequence which has at least 95% sequence identity with the mature polypeptide of SEQ ID NO: 4;
   (b) a polypeptide which is encoded by a polynucleotide which hybridizes under at least high stringency conditions with (i) the mature polypeptide coding sequence of SEQ ID NO: 3, (ii) the cDNA sequence contained in the mature polypeptide coding sequence of SEQ ID NO: 3, or (iii) a full-length complementary strand of (i) or (ii); and
   (c) a polypeptide which is encoded by a polynucleotide having at least 95% sequence identity with the mature polypeptide coding sequence of SEQ ID NO: 3.

2. The polypeptide of claim 1, which comprises or consists of the amino acid sequence of SEQ ID NO: 4.

3. The polypeptide of claim 1, which is encoded by a polynucleotide comprising or consisting of SEQ ID NO: 3.

4. The polypeptide of claim 1, which is encoded by the polynucleotide contained in plasmid pCIC161 which is contained in E. coli NRRL B-30902.

5. An isolated polynucleotide comprising a nucleotide sequence which encodes the polypeptide of claim 1.

6. A nucleic acid construct comprising the polynucleotide of claim 5 operably linked to one or more control sequences that direct the production of the polypeptide in an expression host.

7. A recombinant host cell comprising the nucleic acid construct of claim 6.

8. A method for producing the polypeptide of claim 1 comprising: (a) cultivating a cell, which in its wild-type form is capable of producing the polypeptide, under conditions conducive for production of the polypeptide; and (b) recovering the polypeptide.

9. A method for producing the polypeptide of claim 1 comprising: (a) cultivating a host cell comprising a nucleic acid construct comprising a nucleotide sequence encoding the polypeptide under conditions conducive for production of the polypeptide; and (b) recovering the polypeptide.

10. A method for producing a mutant of a parent cell, which comprises disrupting or deleting a nucleotide sequence encoding the polypeptide of claim 1, which results in the mutant producing less of the polypeptide than the parent cell.

11. A method for producing the polypeptide of claim 1, comprising: (a) cultivating a transgenic plant or a plant cell comprising a polynucleotide encoding a polypeptide having endoglucanase activity under conditions conducive for production of the polypeptide; and (b) recovering the polypeptide.

12. A transgenic plant, plant part or plant cell, which has been transformed with a polynucleotide encoding the polypeptide of claim 1.

13. A method of degrading or converting a cellulosic material, comprising: treating the cellulosic material with a composition comprising an effective amount of a polypeptide having endoglucanase activity of claim 1.

14. A method of degrading or converting a cellulosic material, comprising: treating the biomass with a composition comprising the host cell of claim 7.

15. A method of producing a substance, comprising: (a) saccharifying a cellulosic material with a composition comprising an effective amount of a polypeptide having endoglucanase activity of claim 1, (b) fermenting the saccharified cellulosic material of step (a) with one or more fermentating microorganisms; and (c) recovering the substance from the fermentation.

16. The polypeptide of claim 1, comprising an amino acid sequence which has at least 97% sequence identity with the mature polypeptide of SEQ ID NO: 4.

17. The polypeptide of claim 1, comprising an amino acid sequence which has at least 98% sequence identity with the mature polypeptide of SEQ ID NO: 4.

18. The polypeptide of claim 1, comprising an amino acid sequence which has at least 99% sequence identity with the mature polypeptide of SEQ ID NO: 4.

19. The polypeptide of claim 1, comprising or consisting of the amino acid sequence of the mature polypeptide of SEQ ID NO: 4.

20. The polypeptide of claim 19, wherein the mature polypeptide is amino acids 17 to 389 of SEQ ID NO: 4.

21. The polypeptide of claim 1, which is encoded by a polynucleotide having at least 97% sequence identity with the mature polypeptide coding sequence of SEQ ID NO: 3.

22. The polypeptide of claim 1, which is encoded by a polynucleotide having at least 98% sequence identity with the mature polypeptide coding sequence of SEQ ID NO: 3.

23. The polypeptide of claim 1, which is encoded by a polynucleotide having at least 99% sequence identity with the mature polypeptide coding sequence of SEQ ID NO: 3.

24. The polypeptide of claim 1, which is encoded by a polynucleotide comprising or consisting of the mature polypeptide coding sequence of SEQ ID NO: 3.

25. The polypeptide of claim 24, wherein the mature polypeptide coding sequence is nucleotides 67 to 1185 of SEQ ID NO: 3.

26. The polypeptide of claim 1, which is encoded by a polynucleotide which hybridizes under at least very high stringency conditions with (i) the mature polypeptide coding sequence of SEQ ID NO: 3, (ii) the cDNA sequence contained in the mature polypeptide coding sequence of SEQ ID NO: 3, or (iii) a full-length complementary strand of (i) or (ii).

* * * * *

SEQUENCE LISTING

```
<160> NUMBER OF SEQ ID NOS: 15

<210> SEQ ID NO 1
<211> LENGTH: 12
<212> TYPE: DNA
<213> ORGANISM: Myceliophthora thermophila

<400> SEQUENCE: 1
ctttccagca ca                                                         12

<210> SEQ ID NO 2
<211> LENGTH: 8
<212> TYPE: DNA
<213> ORGANISM: Myceliophthora thermophila

<400> SEQUENCE: 2 gaaaggtc                                                               8

<210> SEQ ID NO 3
<211> LENGTH: 1188
<212> TYPE: DNA
<213> ORGANISM: Myceliophthora thermophila

<400> SEQUENCE: 3
cgacttgaaa cgccccaaat gaagtcctcc atcctcgcca gcgtcttcgc cacgggcgcc      60
gtggctcaaa gtggtccgtg gcagcaatgt ggtggcatcg gatggcaagg atcgaccgac     120
tgtgtgtcgg gctaccactg cgtctaccag aacgattggt acagccagtg cgtgcctggc     180
gcggcgtcga caacgctgca gacatcgacc acgtccaggc ccaccgccac cagcaccgcc     240
cctccgtcgt ccaccacctc gcctagcaag ggcaagctga agtggctcgg cagcaacgag     300
tcgggcgccg agttcggcga gggcaattac cccggcctct ggggcaagca cttcatcttc     360
ccgtcgactt cggcgattca gacgctcatc aatgatggat acaacatctt ccggatcgac     420
ttctcgatgg agcgtctggt gcccaaccag ttgacgtcgt ccttcgacca gggttacctc     480
cgcaacctga ccgaggtggt caacttcgtg acgaacgcgg gcaagtacgc cgtcctggac     540
```

```
ccgcacaact acggccggta ctacggcaac atcatcacgg acacgaacgc gttccggacc    600
ttctggacca acctggccaa gcagttcgcc tccaactcgc tcgtcatctt cgacaccaac    660
aacgagtaca acacgatgga ccagaccctg gtgctcaacc tcaaccaggc cgccatcgac    720
ggcatccggg ccgccggcgc gacctcgcag tacatcttcg tcgagggcaa cgcgtggagc    780
ggggcctgga gctggaacac gaccaacacc aacatggccg ccctgacgga cccgcagaac    840
aagatcgtgt acgagatgca ccagtacctc gactcggaca gctcgggcac ccacgccgag    900
tgcgtcagca gcaccatcgg cgcccagcgc gtcgtcggag ccacccagtg gctccgcgcc    960
aacggcaagc tcggcgtcct cggcgagttc gccggcggcg ccaacgccgt ctgccagcag   1020
gccgtcaccg gcctcctcga ccacctccag gacaacagcg acgtctggct gggtgccctc   1080
tggtgggccg ccggtccctg gtggggcgac tacatgtact cgttcgagcc tccttcgggc   1140
accggctatg tcaactacaa ctcgatcttg aagaagtact tgccgtaa               1188
```

<210> SEQ ID NO 4
<211> LENGTH: 389
<212> TYPE: PRT
<213> ORGANISM: Myceliophthora thermophila

<400> SEQUENCE: 4

```
Met Lys Ser Ser Ile Leu Ala Ser Val Phe Ala Thr Gly Ala Val Ala
1               5                   10                  15

Gln Ser Gly Pro Trp Gln Gln Cys Gly Gly Ile Gly Trp Gln Gly Ser
            20                  25                  30

Thr Asp Cys Val Ser Gly Tyr His Cys Val Tyr Gln Asn Asp Trp Tyr
        35                  40                  45

Ser Gln Cys Val Pro Gly Ala Ala Ser Thr Thr Leu Gln Thr Ser Thr
    50                  55                  60

Thr Ser Arg Pro Thr Ala Thr Ser Thr Ala Pro Pro Ser Ser Thr Thr
65                  70                  75                  80

Ser Pro Ser Lys Gly Lys Leu Lys Trp Leu Gly Ser Asn Glu Ser Gly
                85                  90                  95

Ala Glu Phe Gly Glu Gly Asn Tyr Pro Gly Leu Trp Gly Lys His Phe
            100                 105                 110

Ile Phe Pro Ser Thr Ser Ala Ile Gln Thr Leu Ile Asn Asp Gly Tyr
        115                 120                 125

Asn Ile Phe Arg Ile Asp Phe Ser Met Glu Arg Leu Val Pro Asn Gln
    130                 135                 140

Leu Thr Ser Ser Phe Asp Gln Gly Tyr Leu Arg Asn Leu Thr Glu Val
145                 150                 155                 160

Val Asn Phe Val Thr Asn Ala Gly Lys Tyr Ala Val Leu Asp Pro His
                165                 170                 175

Asn Tyr Gly Arg Tyr Tyr Gly Asn Ile Ile Thr Asp Thr Asn Ala Phe
            180                 185                 190

Arg Thr Phe Trp Thr Asn Leu Ala Lys Gln Phe Ala Ser Asn Ser Leu
        195                 200                 205

Val Ile Phe Asp Thr Asn Asn Glu Tyr Asn Thr Met Asp Gln Thr Leu
    210                 215                 220

Val Leu Asn Leu Asn Gln Ala Ala Ile Asp Gly Ile Arg Ala Ala Gly
225                 230                 235                 240

Ala Thr Ser Gln Tyr Ile Phe Val Glu Gly Asn Ala Trp Ser Gly Ala
                245                 250                 255

Trp Ser Trp Asn Thr Thr Asn Thr Asn Met Ala Ala Leu Thr Asp Pro
```

```
                  260               265               270
Gln Asn Lys Ile Val Tyr Glu Met His Gln Tyr Leu Asp Ser Asp Ser
        275                 280                 285
Ser Gly Thr His Ala Glu Cys Val Ser Ser Thr Ile Gly Ala Gln Arg
        290                 295                 300
Val Val Gly Ala Thr Gln Trp Leu Arg Ala Asn Gly Lys Leu Gly Val
305                 310                 315                 320
Leu Gly Glu Phe Ala Gly Ala Asn Ala Val Cys Gln Gln Ala Val
                325                 330                 335
Thr Gly Leu Leu Asp His Leu Gln Asp Asn Ser Asp Val Trp Leu Gly
                340                 345                 350
Ala Leu Trp Trp Ala Ala Gly Pro Trp Trp Gly Asp Tyr Met Tyr Ser
        355                 360                 365
Phe Glu Pro Pro Ser Gly Thr Gly Tyr Val Asn Tyr Asn Ser Ile Leu
        370                 375                 380
Lys Lys Tyr Leu Pro
385

<210> SEQ ID NO 5
<211> LENGTH: 1232
<212> TYPE: DNA
<213> ORGANISM: Unknown
<220> FEATURE:
<223> OTHER INFORMATION: Basidiomycete CBS 495.95

<400> SEQUENCE: 5
ggatccactt agtaacggcc gccagtgtgc tggaaagcat gaagtctctc ttcctgtcac      60
ttgtagcgac cgtcgcgctc agctcgccag tattctctgt cgcagtctgg gggcaatgcg     120
gcggcattgg cttcagcgga agcaccgtct gtgatgcagg cgccggctgt gtgaagctca     180
acgactatta ctctcaatgc caacccggcg ctcccactgc tacatccgcg cgccaagta     240 gcaacgcacc gtccggcact tcgacggcct cggccccctc ctccagcctt tgctctggca     300
gccgcacgcc gttccagttc ttcggtgtca acgaatccgg cgcggagttc ggcaacctga     360
acatccccgg tgttctgggc accgactaca cctggccgtc gccatccagc attgacttct     420
tcatgggcaa gggaatgaat accttccgta ttccgttcct catggagcgt cttgtccccc     480
ctgccactgg catcacagga cctctcgacc agacgtactt gggcggcctg cagacgattg     540
tcaactacat caccggcaaa ggcggctttg ctctcattga cccgcacaac tttatgatct     600
acaatggcca gacgatctcc agtaccagcg acttccagaa gttctggcag aacctcgcag     660
gagtgtttaa atcgaacagt cacgtcatct tcgatgttat gaacgagcct cacgatattc     720
ccgcccagac cgtgttccaa ctgaaccaag ccgctgtcaa tggcatccgt gcgagcggtg     780
cgacgtcgca gctcattctg gtcgagggca aagctggac tggagcctgg acctggacga     840
cctctggcaa cagcgatgca ttcggtgcca ttaaggatcc caacaacaac gtcgcgatcc     900
agatgcatca gtacctggat agcgatggct ctggcacttc gcagacctgc gtgtctccca     960
ccatcggtgc cgagcggttg caggctgcga ctcaatggtt gaagcagaac aacctcaagg    1020
gcttcctggg cgagatcggc gccggctcta actccgcttg catcagcgct gtgcagggtg    1080
cgttgtgttc gatgcagcaa tctggtgtgt ggctcggcgc tctctggtgg gctgcgggcc    1140
cgtggtgggg cgactactac cagtccatcg agccgccctc tggcccggcg gtgtccgcga    1200
tcctcccgca ggccctgctg ccgttcgcgt aa                                  1232

<210> SEQ ID NO 6
```

```
<211> LENGTH: 397
<212> TYPE: PRT
<213> ORGANISM: Unknown
<220> FEATURE:
<223> OTHER INFORMATION: Basidiomycete CBS 495.95

<400> SEQUENCE: 6

Met Lys Ser Leu Phe Leu Ser Leu Val Ala Thr Val Ala Leu Ser Ser
1               5                   10                  15

Pro Val Phe Ser Val Ala Val Trp Gly Gln Cys Gly Gly Ile Gly Phe
            20                  25                  30

Ser Gly Ser Thr Val Cys Asp Ala Gly Ala Gly Cys Val Lys Leu Asn
        35                  40                  45

Asp Tyr Tyr Ser Gln Cys Gln Pro Gly Ala Pro Thr Ala Thr Ser Ala
    50                  55                  60

Ala Pro Ser Ser Asn Ala Pro Ser Gly Thr Ser Thr Ala Ser Ala Pro
65                  70                  75                  80

Ser Ser Ser Leu Cys Ser Gly Ser Arg Thr Pro Phe Gln Phe Gly
                85                  90                  95

Val Asn Glu Ser Gly Ala Glu Phe Gly Asn Leu Asn Ile Pro Gly Val
            100                 105                 110

Leu Gly Thr Asp Tyr Thr Trp Pro Ser Pro Ser Ser Ile Asp Phe Phe
        115                 120                 125

Met Gly Lys Gly Met Asn Thr Phe Arg Ile Pro Phe Leu Met Glu Arg
    130                 135                 140

Leu Val Pro Pro Ala Thr Gly Ile Thr Gly Pro Leu Asp Gln Thr Tyr
145                 150                 155                 160

Leu Gly Gly Leu Gln Thr Ile Val Asn Tyr Ile Thr Gly Lys Gly Gly
                165                 170                 175

Phe Ala Leu Ile Asp Pro His Asn Phe Met Ile Tyr Asn Gly Gln Thr
            180                 185                 190

Ile Ser Ser Thr Ser Asp Phe Gln Lys Phe Trp Gln Asn Leu Ala Gly
        195                 200                 205

Val Phe Lys Ser Asn Ser His Val Ile Phe Asp Val Met Asn Glu Pro
    210                 215                 220

His Asp Ile Pro Ala Gln Thr Val Phe Gln Leu Asn Gln Ala Ala Val
225                 230                 235                 240

Asn Gly Ile Arg Ala Ser Gly Ala Thr Ser Gln Leu Ile Leu Val Glu
                245                 250                 255

Gly Thr Ser Trp Thr Gly Ala Trp Thr Trp Thr Thr Ser Gly Asn Ser
            260                 265                 270

Asp Ala Phe Gly Ala Ile Lys Asp Pro Asn Asn Val Ala Ile Gln
        275                 280                 285

Met His Gln Tyr Leu Asp Ser Asp Gly Ser Gly Thr Ser Gln Thr Cys
    290                 295                 300

Val Ser Pro Thr Ile Gly Ala Glu Arg Leu Gln Ala Ala Thr Gln Trp
305                 310                 315                 320

Leu Lys Gln Asn Asn Leu Lys Gly Phe Leu Gly Glu Ile Gly Ala Gly
                325                 330                 335

Ser Asn Ser Ala Cys Ile Ser Ala Val Gln Gly Ala Leu Cys Ser Met
            340                 345                 350

Gln Gln Ser Gly Val Trp Leu Gly Ala Leu Trp Ala Ala Gly Pro
        355                 360                 365

Trp Trp Gly Asp Tyr Tyr Gln Ser Ile Glu Pro Pro Ser Gly Pro Ala
    370                 375                 380
```

Val Ser Ala Ile Leu Pro Gln Ala Leu Leu Pro Phe Ala
385                 390                 395

<210> SEQ ID NO 7
<211> LENGTH: 1303
<212> TYPE: DNA
<213> ORGANISM: Unknown
<220> FEATURE:
<223> OTHER INFORMATION: Basidiomycete CBS 495.95

<400> SEQUENCE: 7

```
ggaaagcgtc agtatggtga aatttgcgct tgtggcaact gtcggcgcaa tcttgagcgc    60
ttctgcggcc aatgcggctt ctatctacca gcaatgtgga ggcattggat ggtctgggtc   120
cactgtttgc gacgccggtc tcgcttgcgt tatcctcaat gcgtactact ttcagtgctt   180
gacgcccgcc gcgggccaga caacgacggg ctcgggcgca ccggcgtcaa catcaacctc   240
tcactcaacg gtcactacgg ggagctcaca ctcaacaacc gggacgacgg cgacgaaaac   300
aactaccact ccgtcgacca ccacgaccct acccgccatc tctgtgtctg gtcgcgtctg   360
ctctggctcc aggacgaagt tcaagttctt cggtgtgaat gaaagcggcg ccgaattcgg   420
gaacactgct tggccagggc agctcgggaa agactataca tggccttcgc ctagcagcgt   480
ggactacttc atggggctg gattcaatac attccgtatc accttcttga tggagcgtat   540
gagccctccg gctaccggac tcactggccc attcaaccag acgtacctgt cgggcctcac   600
caccattgtc gactacatca cgaacaaagg aggatacgct cttattgacc cccacaactt   660
catgcgttac aacaacggca taatcagcag cacatctgac ttcgcgactt ggtggagcaa   720
tttggccact gtattcaaat ccacgaagaa cgccatcttc gacatccaga acgagccgta   780
cggaatcgat gcgcagaccg tatacgaact gaatcaagct gccatcaatt cgatccgcgc   840
cgctggcgct acgtcacagt tgattctggt tgaaggaacg tcatacactg gagcttggac   900
gtgggtctcg tccggaaacg gagctgcttt cgcggccgtt acggatcctt acaacaacac   960
ggcaattgaa atgcaccaat acctcgacag cgacggttct gggacaaacg aagactgtgt  1020
ctcctccacc attgggtcgc aacgtctcca agctgccact gcgtggctgc aacaaacagg  1080
actcaaggga ttcctcggag agacgggtgc tgggtcgaat tcccagtgca tcgacgccgt  1140
gttcgatgaa ctttgctata tgcaacagca aggcggctcc tggatcggtg cactctggtg  1200
ggctgcgggt ccctggtggg gcacgtacat ttactcgatt gaacctccga gcggtgccgc  1260
tatcccagaa gtccttcctc agggtctcgc tccattcctc tag                    1303
```

<210> SEQ ID NO 8
<211> LENGTH: 429
<212> TYPE: PRT
<213> ORGANISM: Unknown
<220> FEATURE:
<223> OTHER INFORMATION: Basidiomycete CBS 495.95

<400> SEQUENCE: 8

Met Val Lys Phe Ala Leu Val Ala Thr Val Gly Ala Ile Leu Ser Ala
1               5                   10                  15

Ser Ala Ala Asn Ala Ala Ser Ile Tyr Gln Gln Cys Gly Gly Ile Gly
                20                  25                  30

Trp Ser Gly Ser Thr Val Cys Asp Ala Gly Leu Ala Cys Val Ile Leu
            35                  40                  45

Asn Ala Tyr Tyr Phe Gln Cys Leu Thr Pro Ala Ala Gly Gln Thr Thr
        50                  55                  60

Thr Gly Ser Gly Ala Pro Ala Ser Thr Ser Thr Ser His Ser Thr Val

```
              65                  70                  75                  80
Thr Thr Gly Ser Ser His Ser Thr Thr Gly Thr Thr Ala Thr Lys Thr
                        85                  90                  95
Thr Thr Thr Pro Ser Thr Thr Thr Thr Leu Pro Ala Ile Ser Val Ser
                100                 105                 110
Gly Arg Val Cys Ser Gly Ser Arg Thr Lys Phe Lys Phe Phe Gly Val
            115                 120                 125
Asn Glu Ser Gly Ala Glu Phe Gly Asn Thr Ala Trp Pro Gly Gln Leu
        130                 135                 140
Gly Lys Asp Tyr Thr Trp Pro Ser Pro Ser Ser Val Asp Tyr Phe Met
145                 150                 155                 160
Gly Ala Gly Phe Asn Thr Phe Arg Ile Thr Phe Leu Met Glu Arg Met
                165                 170                 175
Ser Pro Pro Ala Thr Gly Leu Thr Gly Pro Phe Asn Gln Thr Tyr Leu
            180                 185                 190
Ser Gly Leu Thr Thr Ile Val Asp Tyr Ile Thr Asn Lys Gly Gly Tyr
        195                 200                 205
Ala Leu Ile Asp Pro His Asn Phe Met Arg Tyr Asn Asn Gly Ile Ile
    210                 215                 220
Ser Ser Thr Ser Asp Phe Ala Thr Trp Trp Ser Asn Leu Ala Thr Val
225                 230                 235                 240
Phe Lys Ser Thr Lys Asn Ala Ile Phe Asp Ile Gln Asn Glu Pro Tyr
                245                 250                 255
Gly Ile Asp Ala Gln Thr Val Tyr Glu Leu Asn Gln Ala Ala Ile Asn
            260                 265                 270
Ser Ile Arg Ala Ala Gly Ala Thr Ser Gln Leu Ile Leu Val Glu Gly
        275                 280                 285
Thr Ser Tyr Thr Gly Ala Trp Thr Trp Val Ser Ser Gly Asn Gly Ala
    290                 295                 300
Ala Phe Ala Ala Val Thr Asp Pro Tyr Asn Asn Thr Ala Ile Glu Met
305                 310                 315                 320
His Gln Tyr Leu Asp Ser Asp Gly Ser Gly Thr Asn Glu Asp Cys Val
                325                 330                 335
Ser Ser Thr Ile Gly Ser Gln Arg Leu Gln Ala Ala Thr Ala Trp Leu
            340                 345                 350
Gln Gln Thr Gly Leu Lys Gly Phe Leu Gly Glu Thr Gly Ala Gly Ser
        355                 360                 365
Asn Ser Gln Cys Ile Asp Ala Val Phe Asp Glu Leu Cys Tyr Met Gln
    370                 375                 380
Gln Gln Gly Gly Ser Trp Ile Gly Ala Leu Trp Trp Ala Ala Gly Pro
385                 390                 395                 400
Trp Trp Gly Thr Tyr Ile Tyr Ser Ile Glu Pro Pro Ser Gly Ala Ala
                405                 410                 415
Ile Pro Glu Val Leu Pro Gln Gly Leu Ala Pro Phe Leu
            420                 425

<210> SEQ ID NO 9
<211> LENGTH: 1488
<212> TYPE: DNA
<213> ORGANISM: Penicillium brasilianum

<400> SEQUENCE: 9
atgaaatacc ctctactcct ggcaaccagc gctgccctgg ctcttgctgg gcctcaaggc      60
ttctccaagc gagcctcttc ttttgtttgt atgtgtagag cccataagaa taagagctgg     120
```

```
aactgacctg aatttttagg gtttggtacc agcgagtctg gggcggagtt tggcaatcag    180
aacattccgg gtgttttggg gacggactac atttggcccg acacttcagc cattcaaacg    240
ctacgcaacg cgggtatgaa catctttcgg gtggcatttt tgatggagcg attggttccc    300
accacattga cctcaactcc ggattcgacg tatctgcaag acctgaagag tgtacgttat    360
cctcgtcaac aatgcaaccc gtgctaaacg atctccagac agttgactac atcacgtcga    420
ccggcgcata tgctattgtg dacccccata actttggacg atagtaagtt gaaccttca     480
tctaaccaat attgaaaatc tcctcacggg tgtattagct atggcaatat aatcaactcc    540
acaagtgact ttgctgcatt ttggaccacc gtcgcaaagc agtttgcatc gaatgacaag    600
gtcatctttg acacgagtga gcatcactac ttcactaact ttgttccccc actaactgac    660
atctgcagac aacgaattca acacagagga ccaaacgctt gtactgaacc tcaatcaagc    720
ggccattaat gccatccgag ctgccggagc cacctctcag tatatctttg tggaagggaa    780
ttcgtggagt ggtgcctgga cgtggacgtc ggtcaatacc aatctcgtca gcttgacgga    840
ccccaacaac aagatagtct acgagatgca ccagtatctt gactcggatg gatctggcac    900
atccgacaca tgtgtcagct cgaccatcgg ccaggagcgt gtacaatcgg cgaccgagtg    960
gctgaaaagc aatggcaaac ttggattctt gggcgaattt gcggcggtg ctaactcggt   1020
ctgtcagagc gccgtgactg gaatgctgga ctatatgcaa gcgaatagtg acgtctggct   1080
cggcgcatcc tggtgggcag caggaccatg gtggggaacc tatatatatt cgattgagcc   1140
gccatcgggg actgcttatt cttactatct caacatcttg tctgcctact tcccctccag   1200
ctcgggaagt tccacaacca caactacctc cactaccacc cgctctacat cgacaagcac   1260
tacagtatcc accacaaaat caacaagcac cactacaagc gccacgaaat cgacaagcac   1320
cacgacaagc accaccagca ccgggtctac tgctactgca acagcatctc actgggcaca   1380
gtgtggcggc attggctgga cggggcgac gacgtgtgcc agcccgtata cctgccaggt   1440
ccagaatgcg tattattcgc agtgtctgta atgcagaagt atcagaaa                1488
```

<210> SEQ ID NO 10
<211> LENGTH: 421
<212> TYPE: PRT
<213> ORGANISM: Penicillium brasilianum

<400> SEQUENCE: 10

```
Met Lys Tyr Pro Leu Leu Ala Thr Ser Ala Ala Leu Ala Leu Ala
1               5                   10                  15

Gly Pro Gln Gly Phe Ser Lys Arg Ala Ser Ser Phe Val Trp Phe Gly
            20                  25                  30

Thr Ser Glu Ser Gly Ala Glu Phe Gly Asn Gln Asn Ile Pro Gly Val
        35                  40                  45

Leu Gly Thr Asp Tyr Ile Trp Pro Asp Thr Ser Ala Ile Gln Thr Leu
    50                  55                  60

Arg Asn Ala Gly Met Asn Ile Phe Arg Val Ala Phe Leu Met Glu Arg
65                  70                  75                  80

Leu Val Pro Thr Thr Leu Thr Ser Thr Pro Asp Ser Thr Tyr Leu Gln
                85                  90                  95

Asp Leu Lys Ser Val Leu Asp Tyr Ile Thr Ser Gly Ala Tyr Ala
            100                 105                 110

Ile Val Asp Pro His Asn Phe Gly Arg Tyr Tyr Gly Asn Ile Ile Asn
        115                 120                 125

Ser Thr Ser Asp Phe Ala Ala Phe Trp Thr Thr Val Ala Lys Gln Phe
    130                 135                 140
```

```
Ala Ser Asn Asp Lys Val Ile Phe Asp Thr Asn Asn Glu Phe Asn Thr
145                 150                 155                 160

Glu Asp Gln Thr Leu Val Leu Asn Leu Asn Gln Ala Ala Ile Asn Ala
            165                 170                 175

Ile Arg Ala Ala Gly Ala Thr Ser Gln Tyr Ile Phe Val Glu Gly Asn
        180                 185                 190

Ser Trp Ser Gly Ala Trp Thr Trp Thr Ser Val Asn Thr Asn Leu Val
    195                 200                 205

Ser Leu Thr Asp Pro Asn Asn Lys Ile Val Tyr Glu Met His Gln Tyr
210                 215                 220

Leu Asp Ser Asp Gly Ser Gly Thr Ser Asp Thr Cys Val Ser Ser Thr
225                 230                 235                 240

Ile Gly Gln Glu Arg Val Gln Ser Ala Thr Glu Trp Leu Lys Ser Asn
            245                 250                 255

Gly Lys Leu Gly Phe Leu Gly Glu Phe Ala Gly Gly Ala Asn Ser Val
        260                 265                 270

Cys Gln Ser Ala Val Thr Gly Met Leu Asp Tyr Met Gln Ala Asn Ser
    275                 280                 285

Asp Val Trp Leu Gly Ala Ser Trp Trp Ala Ala Gly Pro Trp Trp Gly
290                 295                 300

Thr Tyr Ile Tyr Ser Ile Glu Pro Pro Ser Gly Thr Ala Tyr Ser Tyr
305                 310                 315                 320

Tyr Leu Asn Ile Leu Ser Ala Tyr Phe Pro Ser Ser Ser Gly Ser Ser
            325                 330                 335

Thr Thr Thr Thr Thr Ser Thr Thr Thr Arg Ser Thr Ser Thr Ser Thr
        340                 345                 350

Thr Val Ser Thr Thr Lys Ser Thr Ser Thr Thr Thr Ser Ala Thr Lys
    355                 360                 365

Ser Thr Ser Thr Thr Thr Ser Thr Thr Ser Thr Gly Ser Thr Ala Thr
370                 375                 380

Ala Thr Ala Ser His Trp Ala Gln Cys Gly Gly Ile Gly Trp Thr Gly
385                 390                 395                 400

Ala Thr Thr Cys Ala Ser Pro Tyr Thr Cys Gln Val Gln Asn Ala Tyr
            405                 410                 415

Tyr Ser Gln Cys Leu
        420

<210> SEQ ID NO 11
<211> LENGTH: 29
<212> TYPE: DNA
<213> ORGANISM: Penicillium brasilianum
<220> FEATURE:
<221> NAME/KEY: misc_feature
<222> LOCATION: (21)..(21)
<223> OTHER INFORMATION: N= A,C,G,OR T
<220> FEATURE:
<221> NAME/KEY: misc_feature
<222> LOCATION: (24)..(24)
<223> OTHER INFORMATION: N= A,C,G,OR T
<220> FEATURE:
<221> NAME/KEY: misc_feature
<222> LOCATION: (27)..(27)
<223> OTHER INFORMATION: R= A OR G

<400> SEQUENCE: 11
ttcggtacct ctgagtctgg ngcngartt                                    29

<210> SEQ ID NO 12
<211> LENGTH: 35
```

```
<212> TYPE: DNA
<213> ORGANISM: Penicillium brasilianum
<220> FEATURE:
<221> NAME/KEY: misc_feature
<222> LOCATION: (24)..(24)
<223> OTHER INFORMATION: R=A OR G
<220> FEATURE:
<221> NAME/KEY: misc_feature
<222> LOCATION: (27)..(27)
<223> OTHER INFORMATION: N=A,C,G, OR T
<220> FEATURE:
<221> NAME/KEY: misc_feature
<222> LOCATION: (30)..(30)
<223> OTHER INFORMATION: R=A OR G
<220> FEATURE:
<221> NAME/KEY: misc_feature
<222> LOCATION: (33)..(33)
<223> OTHER INFORMATION: R=A OR G

<400> SEQUENCE: 12
tgatccatat cgtggtactc gttrttngtr tcraa                              35

<210> SEQ ID NO 13
<211> LENGTH: 29
<212> TYPE: DNA
<213> ORGANISM: Penicillium brasilianum
<220> FEATURE:
<221> NAME/KEY: misc_feature
<222> LOCATION: (18)..(18)
<223> OTHER INFORMATION: R=A OR G
<220> FEATURE:
<221> NAME/KEY: misc_feature
<222> LOCATION: (21)..(21)
<223> OTHER INFORMATION: R=A OR G
<220> FEATURE:
<221> NAME/KEY: misc_feature
<222> LOCATION: (24)..(24)
<223> OTHER INFORMATION: N=A,C,G, OR T
<220> FEATURE:
<221> NAME/KEY: misc_feature
<222> LOCATION: (27)..(27)
<223> OTHER INFORMATION: R=A OR G

<400> SEQUENCE: 13
ccgttgtagc gaccgtartt rtgnggrtc                                     29

<210> SEQ ID NO 14
<211> LENGTH: 39
<212> TYPE: DNA
<213> ORGANISM: Penicillium brasilianum

<400> SEQUENCE: 14
aattggatcc accatgaaat accctctact cctggcaac                          39

<210> SEQ ID NO 15
<211> LENGTH: 38
<212> TYPE: DNA
<213> ORGANISM: Penicillium brasilianum

<400> SEQUENCE: 15
ttaactcgag ttacagacac tgcgaataat acgcattc                           38
```